(12) United States Patent
Take et al.

(10) Patent No.: US 12,333,790 B2
(45) Date of Patent: Jun. 17, 2025

(54) DIAGNOSTIC ASSISTANCE APPARATUS AND MODEL GENERATION APPARATUS

(71) Applicant: Murata Manufacturing Co., Ltd., Kyoto (JP)

(72) Inventors: Kouji Take, Kyoto (JP); Kazuki Matsui, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 448 days.

(21) Appl. No.: 17/821,850

(22) Filed: Aug. 24, 2022

(65) Prior Publication Data

US 2023/0005251 A1    Jan. 5, 2023

Related U.S. Application Data

(63) Continuation of application No. PCT/JP2020/011839, filed on Mar. 17, 2020.

(51) Int. Cl.
*G06K 9/00* (2022.01)
*G06T 7/00* (2017.01)
*G06V 10/774* (2022.01)
*G16H 30/40* (2018.01)

(52) U.S. Cl.
CPC ........ *G06V 10/7747* (2022.01); *G06T 7/0014* (2013.01); *G16H 30/40* (2018.01); *G06T 2207/20081* (2013.01)

(58) Field of Classification Search
CPC ........... G06V 10/7747; G06V 2201/03; G06V 10/82; G06T 7/0014; G06T 2207/20081; G06T 2207/10116; G06T 2207/20084; G06T 2207/30061; G06T 7/0012; G16H 30/40; G16H 50/20; G16H 50/70; G16H 30/20; G06N 3/08; G06N 20/00
See application file for complete search history.

(56) References Cited

U.S. PATENT DOCUMENTS

| | | | |
|---|---|---|---|
| 2018/0137941 A1 | 5/2018 | Chen | |
| 2018/0144466 A1 | 5/2018 | Hsieh et al. | |
| 2019/0131012 A1 | 5/2019 | Osawa | |
| 2020/0035350 A1 | 1/2020 | Sullivan et al. | |

FOREIGN PATENT DOCUMENTS

| | | | | |
|---|---|---|---|---|
| CN | 108427951 A | * | 8/2018 | ........... G06K 9/3233 |
| CN | 108665457 A | * | 10/2018 | ............. G06F 18/24 |
| CN | 109074500 A | * | 12/2018 | ............. A61B 6/032 |
| JP | 2018-529134 A | | 10/2018 | |
| JP | 2019-082881 A | | 5/2019 | |
| JP | 2019-087181 A | | 6/2019 | |
| JP | 2020-500377 A | | 1/2020 | |
| WO | WO-2020263002 A1 | * | 12/2020 | |

OTHER PUBLICATIONS

International Search Report for PCT/JP2020/011839 dated Jul. 28, 2020.

* cited by examiner

*Primary Examiner* — Xin Jia
(74) *Attorney, Agent, or Firm* — McDonald Hopkins LLC

(57) ABSTRACT

A diagnostic assistance apparatus according to an aspect of the present disclosure determines whether a body part of a target examinee captured in a target medical image is normal, by using a trained first classification model generated by unsupervised learning using a plurality of first learning medical images of normal cases and a trained second classification model generated by supervised learning using a plurality of learning data sets including normal cases and abnormal cases.

20 Claims, 13 Drawing Sheets

DIAGNOSTIC ASSISTANCE APPARATUS AND MODEL GENERATION APPARATUS

CROSS REFERENCE TO RELATED APPLICATION

This is a continuation of International Application No. PCT/JP2020/011839 filed on Mar. 17, 2020. The content of this application is incorporated herein by reference in its entirety.

BACKGROUND OF THE DISCLOSURE

Field of the Disclosure

The present disclosure relates to a diagnostic assistance apparatus and a model generation apparatus.

Description of the Related Art

In recent years, technologies of assisting diagnoses based on medical images have been developed with the use of artificial intelligence. For example, Patent Document 1 describes supervised learning of a multilayer neural network, using images with correct labels indicating results of classifying findings of lesion areas. In this supervised learning, the multilayer neural network is trained to match an input image as training data to a correct label corresponding to a result acquired by classifying a lesion area in the input image. As the result of this supervised learning, the trained multilayer neural network can acquire a capability to classify lesion areas with given images.

Patent Document 1: Japanese Unexamined Patent Application Publication No. 2019-082881

BRIEF SUMMARY OF THE DISCLOSURE

Such a classification model trained by, for example, the supervised learning described in Patent Document 1 can carry out various classification tasks such as classifying the type of a lesion and specifying the location of a lesion area. The inventors of the present disclosure, however, have discovered that this method has the following problem.

Supervised learning is one of the machine learning methods. To put it briefly, supervised learning is a learning method in which a learning model learns the correspondence between training data and correct labels. To create a trained classification model that can carry out classification tasks on medical images, as described above, supervised learning uses learning data sets, each being a combination of a medical image as training data and a correct label indicating a finding on the medical image.

The number of learning data sets used in supervised learning is one of the factors that affect the accuracy of classification with the trained classification model created by supervised learning. Specifically, it can be expected that the more learning data set are used in supervised learning, the more accurate the classification by the trained classification model created by the supervised learning is. Especially when various kinds of training data are used in large amounts, the improvement of accuracy of classification by the trained classification model can be expected.

A large number of medical images can be easily collected with relatively low costs from, for example, regular health checkups. However, most of the people who undergo regular health checkups are healthy. For this reason, it is difficult to collect a large number of medical images capturing abnormal body parts of subjects, which can be used as training data of abnormal cases; furthermore, collecting such medical images is time-consuming and costly. It is, therefore, burdensome to prepare a large number of learning data sets containing both normal cases and abnormal cases in terms of time and cost. This makes it difficult to use supervised learning to create trained classification models with high classification accuracy.

In an aspect, the present disclosure has been made in consideration of the above circumstances, and a possible benefit thereof is to provide a technology for improving accuracy of classifying medical images with relatively low costs.

To address the problem described above, the present disclosure applies the following configurations.

A diagnostic assistance apparatus according to an aspect of the present disclosure includes a data acquisition unit, a first model computation unit having a first classification model, a second model computation unit having a second classification model, a determination unit, and an output unit. The data acquisition unit is configured to acquire a target medical image capturing a body part of a target examinee. The first classification model is trained, by unsupervised learning using a plurality of first learning medical images capturing normal body parts, to provide an evaluation of a degree of normality of a body part captured in a fed medical image by one-class classification. The first model computation unit is configured to, by feeding the acquired target medical image to the trained first classification model and performing an arithmetic operation of the trained first classification model, acquire as a first result a degree of normality evaluated by the one-class classification on the body part of the target examinee captured in the target medical image. The second classification model is trained, by supervised learning using a plurality of learning data sets, each learning data set being a combination of a second learning medical image and a correct label indicating whether a body part captured in the second learning medical image is normal, to provide an evaluation of a degree of normality of a body part captured in a fed medical image. The second learning medical images of the plurality of learning data sets include a normal medical image capturing a normal body part and an abnormal medical image capturing an abnormal body part. The second model computation unit is configured to, by feeding the acquired target medical image to the trained second classification model and performing an arithmetic operation of the trained second classification model, acquire as a second result a degree of normality evaluated on the body part of the target examinee captured in the target medical image. The determination unit is configured to, in accordance with the first result and the second result, provide a determination of whether the body part of the target examinee captured in the target medical image is normal. The output unit is configured to provide an output of a result of the determination.

As described above, learning medical images of normal cases can be easily collected with relatively low costs from, for example regular health checkups, whereas collecting learning data sets including learning medical images of non-normal (abnormal) cases is difficult and costly. In this regard, the diagnostic assistance apparatus according to this configuration uses two classification models of the trained first classification model generated by unsupervised learning and the trained second classification model generated by supervised learning, to classify whether a body part of a target examinee captured in a medical image is normal. With this configuration, the performance of the trained second classification model, which is trained by supervised learning using a relatively small number of learning data sets including training data of abnormal cases, can be supplemented by the trained first classification model, which is trained by unsupervised learning using learning medical images of normal cases easily collectable with relatively low costs. As a result, with this configuration, it is possible to improve accuracy of classifying medical images with relatively low costs. The target examinee may include a model representing a human body (for example, a phantom for X-ray imaging).

In the diagnostic assistance apparatus according to an aspect, the first result and the second result may be configured to indicate the degree of normality of the body part by a numerical value. The determination unit may include a connector having a first parameter determining a priority level of the first result and a second parameter determining a priority level of the second result. The determination by the determination unit may consist of: by feeding the acquired first and second results to the connector, individually weighting the first result and the second result with the first parameter and the second parameter; connecting the weighted first result and the weighted second result; and determining whether the body part of the target examinee is normal by comparing the numerical value (determination value) acquired by the connection operation to a threshold. With this configuration, improvements in the classification accuracy can be properly achieved by tuning parameters.

In the diagnostic assistance apparatus according to an aspect, the first parameter and the second parameter may be tuned to optimize accuracy of the determination on a plurality of third learning medical images, body parts captured in the plurality of third learning medical images being previously determined to be normal or non-normal. With this configuration, by the optimization of the parameters, further improvements in the classification accuracy can be expected.

In the diagnostic assistance apparatus according to an aspect, at least any one of the first parameter, the second parameter, and the threshold may be specified by an input by an operator. With this configuration, to improve the classification accuracy, the parameters can be easily tuned. The operator may include a medical doctor or user who directly or indirectly operates the diagnostic assistance apparatus. Indirectly operating the diagnostic assistance apparatus may include accessing the diagnostic assistance apparatus by using a terminal and receiving operation results from the diagnostic assistance apparatus by using the terminal.

In the diagnostic assistance apparatus according to an aspect, the first classification model may include an encoder configured to provide a conversion of a fed medical image into a feature and a decoder configured to decode the medical image from the feature. The unsupervised learning may include training the encoder and the decoder such that, when each first learning medical image is fed to the encoder, a decoded image responsively generated by the decoder matches the first learning medical image. With this configuration, it is possible to provide the first classification model that can evaluate the degree of normality of a body part captured in a medical image by one-class classification and reconstruct a medical image capturing a normal body part.

In the diagnostic assistance apparatus according to an aspect, the first classification model may further include a one-class classifier trained by the unsupervised learning to provide an evaluation by the one-class classification in accordance with a feature acquired by the encoder. The arithmetic operation of the first classification model may include, by feeding the target feature acquired by the conversion to the trained one-class classifier, acquiring the first result from the trained one-class classifier. With this configuration, it is possible to provide the first classification model that can properly evaluate the degree of normality of a body part captured in a medical image. The one-class classifier may be implemented by any model useable for machine learning. The one-class classifier may be implemented by, for example, a neural network.

In the diagnostic assistance apparatus according to an aspect, the arithmetic operation of the first classification model may include, when the body part of the target examinee is determined to be non-normal, by feeding the acquired target medical image to the trained encoder, providing a conversion of the target medical image into a target feature, by feeding the target feature acquired by the conversion to the trained decoder, generating a target decoded image from the target feature, calculating a difference between the target medical image and the target decoded image generated, and specifying in the target medical image a related area by which the body part of the target examinee is determined to be non-normal (that is, abnormal), in accordance with the calculated difference. The output of a result of the determination may include an output of information indicating the related area specified. With this configuration, as well as to classify whether a body part of a target examinee is normal, when the body part of the target examinee is determined to be non-normal, it is possible to extract a related area relating to the determination. It should be noted that the related area can be interpreted as a possible lesion area.

In the diagnostic assistance apparatus according to an aspect, each learning data set may further include learning attribute information. The second classification model may be trained, by the supervised learning additionally using the learning attribute information, to provide an evaluation of a degree of normality of a body part captured in a fed medical image with reference to fed attribute information. The data acquisition unit may be configured to additionally acquire target attribute information indicating an attribute of the target examinee. The second model computation unit may be configured to acquire the second result by additionally feeding the acquired target attribute information to the trained second classification model and performing the arithmetic operation of the trained second classification model. With this configuration, with additional reference to attribute information, improvements in the classification accuracy can be expected. The attribute may relate to any kinds of person's characteristics such as age, sex, height, weight, waist circumference, and chest measurement.

In the diagnostic assistance apparatus according to an aspect, the second classification model may be implemented by a convolutional neural network. With this configuration, it is possible to provide the second classification model that can properly classify whether a body part captured in a medical image is normal. The configuration of the second classification model is not necessarily limited to this example. The second classification model may be implemented by any model useable for machine learning.

In the diagnostic assistance apparatus according to an aspect, the output of a result of the determination may include associating result information indicating the result of the determination with the target medical image. With this configuration, the convenience of using the acquired target medical image can be increased. For example, in accordance with the associated result information, it is possible to extract only the target medical image capturing a body part determined to be non-normal. Accordingly, only the target medical image capturing a non-normal body part can be displayed on a display device. As a result, the display efficiency of the display device can be enhanced. The data format of the result information is not limited to a particular type, and any type of activation function may be selected as appropriate to the embodiment. The result information may be implemented by, for example, a Digital Imaging and Communications in Medicine (DICOM) tag.

In the diagnostic assistance apparatus according to an aspect, the output of a result of the determination may include combining information indicating the result of the determination with the target medical image. With this configuration, the convenience of using the acquired target medical image can be increased.

The present disclosure is not necessarily implemented as the diagnostic assistance apparatus. An aspect of the present disclosure may be a model generation apparatus for generating a trained first classification model and a trained second classification model usable by the diagnostic assistance apparatus. It should be noted that the model generation apparatus can be interpreted as a learning apparatus.

For example, a model generation apparatus according to an aspect of the present disclosure includes a first acquisition unit, a first learning unit, a second acquisition unit, a second learning unit, a third acquisition unit, a determination unit, and a tuning unit. The first acquisition unit is configured to acquire a plurality of first learning medical images capturing normal body parts. The first learning unit is configured to perform unsupervised learning of a first classification model by using the plurality of first learning medical images acquired. The first classification model is configured to accept an input of a medical image and provide an evaluation of a degree of normality of a body part captured in the input medical image by one-class classification. The unsupervised learning includes training the first classification model such that, when an input medical image belongs to a class of the plurality of first learning medical images, a body part captured in the input medical image is evaluated as normal; when the input medical image does not belong to the class of the plurality of first learning medical images, the body part captured in the input medical image is evaluated as non-normal. The second acquisition unit is configured to acquire a plurality of learning data sets, each learning data set being a combination of a second learning medical image and a correct label indicating whether a body part captured in the second learning medical image is normal. The second learning medical images of the plurality of learning data sets include a normal medical image capturing a normal body part and an abnormal medical image capturing an abnormal body part. The second learning unit is configured to perform supervised learning of a second classification model by using the plurality of learning data sets acquired. The second classification model is configured to accept an input of a medical image and provide an evaluation of a degree of normality of a body part captured in the input medical image. The supervised learning includes training the second classification model such that, with respect to each learning data set, in response to an input of the second learning medical image, when providing an evaluation of a degree of normality on a body part captured in the input second learning medical image, a result of the evaluation matches the correct label corresponding to the second learning medical image. The third acquisition unit is configured to acquire a plurality of third learning medical images, body parts captured in the plurality of third learning medical images being previously determined to be normal or non-normal. The determination unit is configured to, by using the trained first classification model and the trained second classification model, provide a determination of whether a body part captured in each third learning medical image acquired is normal. The determination unit is configured to, by feeding each third learning medical image to the trained first classification model, acquire as a first result a degree of normality evaluated on a body part captured in the third learning medical image by one-class classification. The determination unit is configured to, by feeding each third learning medical image to the trained second classification model, acquire as a second result a degree of normality evaluated on a body part captured in the third learning medical image. The first result and the second result are configured to indicate the degree of normality of the body part by a numerical value. The determination unit includes a connector having a first parameter determining a priority level of the first result and a second parameter determining a priority level of the second result. The determination unit is configured to, by feeding the acquired first result and the acquired second result to the connector, weight the first result and the second result by using the first parameter and the second parameter. The determination unit is configured to provide a connection between the weighted first result and the weighted second result. The determination unit is configured to compare a numerical value (determination value) acquired by the connection to a threshold and accordingly provide a determination of whether a body part captured in each third learning medical image is normal. The tuning unit is configured to tune the first parameter and the second parameter to optimize accuracy of the determination on each third learning medical image. With this configuration, trained machine learning models (the first classification model and the second classification model) with relatively high accuracy of classification on medical images can be generated with relatively low costs.

In the model generation apparatus according to an aspect, the plurality of third learning medical images may include one or a plurality of limit samples; and the tuning unit may be configured to tune the first parameter and the second parameter to avoid making the determination incorrect on all the one or plurality of limit samples. With this configuration, improvements in the accuracy of classification on the limit samples and similar examination targets can be expected. By determining serious cases as the limit samples, it is possible to reduce the probability of misclassification of the serious cases and similar cases.

The model generation apparatus according to an aspect may further include an enlargement processing unit configured to, by subjecting a primary medical image capturing a body part to enlargement processing, generate at least a portion of a collection of the plurality of first learning medical images and the second learning medical images of the plurality of learning data sets. With this configuration, it is possible to easily increase the number of the learning medical images with little cost, thereby improving the classification accuracy of the trained first classification model and the trained second classification model generated. The enlargement processing is generating a new medical image different from the primary medical image by an image processing operation such as parallel translation, while maintaining at least a portion of the feature captured in the primary medical image. For example, the enlargement processing is constituted by parallel translation, rotation, swiveling, flipping or flopping, cropping, contrast change, enlargement, or reduction, or a combination of any operations selected from parallel translation, rotation, swiveling, flipping or flopping, cropping, contrast change, enlargement, and reduction, performed on the primary medical image.

In the diagnostic assistance apparatus according to an aspect and the model generation apparatus according to an aspect, the first result by the first classification model and the second result by the second classification model are treated in parallel with other. The configuration of the apparatuses, however, is not necessarily limited to this example. For example, in the apparatuses, the first result by the first classification model may be inputted to the second classification model.

For example, a model generation apparatus according to an aspect of the present disclosure includes a first acquisition unit, a first learning unit, a second acquisition unit, and a second learning unit. The first acquisition unit is configured to acquire a plurality of first learning medical images capturing normal body parts. The first learning unit is configured to perform unsupervised learning of a first classification model by using the plurality of first learning medical images acquired. The first classification model is configured to accept an input of a medical image and provide an evaluation of a degree of normality of a body part captured in the input medical image by one-class classification. The unsupervised learning includes training the first classification model such that, when an input medical image belongs to a class of the plurality of first learning medical images, a body part captured in the input medical image is evaluated as normal; when the input medical image does not belong to the class of the plurality of first learning medical images, the body part captured in the input medical image is evaluated as non-normal. The second acquisition unit is configured to acquire a plurality of learning data sets, each learning data set being a combination of a second learning medical image and a correct label indicating whether a body part captured in the second learning medical image is normal. The second learning medical images of the plurality of learning data sets include a normal medical image capturing a normal body part and an abnormal medical image capturing an abnormal body part. The second learning unit is configured to perform supervised learning of a second classification model by using the plurality of learning data sets acquired and the trained first classification model. The second classification model is configured to accept an input of a medical image and an input of a result of the evaluation on the medical image by the first classification model and provide an evaluation of a degree of normality of a body part captured in the input medical image. The supervised learning includes training the second classification model such that, with respect to each learning data set, in response to an input of the second learning medical image and an input of a result of the evaluation on the second learning medical image by the first classification model, when providing an evaluation of a degree of normality on a body part captured in the input second learning medical image, a result of the evaluation matches the correct label corresponding to the second learning medical image. With this configuration, trained machine learning models (the first classification model and the second classification model) with relatively high accuracy of classification on medical images can be generated with relatively low costs.

In the model generation apparatus according to an aspect, the first classification model may include a generator configured to generate a pseudo-medical image and a discriminator configured to accept an input of a medical image and identify an origin of the input medical image. The training of the first classification model may include alternately repeating a first step of training the discriminator to identify whether the generator or the plurality of first learning medical images is an origin of an input medical image and a second step of training the generator to generate a pseudo-medical image that degrades discrimination performance of the discriminator. The result of the evaluation by the first classification model may be made based on a difference between an input medical image and a pseudo-medical image generated by the generator. With this configuration, it is possible to provide the trained machine learning models that can properly classify whether a body part captured in a medical image is normal.

In the model generation apparatus according to an aspect, the first classification model may further include an estimator configured to accept an input of a medical image and estimate an input value fed to the generator to generate the input medical image by the generator. The second learning unit may be configured to further train the estimator to, with respect to each learning data set, minimize a difference between the second learning medical image and a pseudo-medical image generated by the trained generator from an estimation value estimated by the estimator from the second learning medical image. With this configuration, it is possible to provide the trained machine learning models that can properly classify whether a body part captured in a medical image is normal.

A diagnostic assistance apparatus according to an aspect of the present disclosure includes a data acquisition unit configured to acquire a target medical image capturing a body part of a target examinee, a determination unit configured to provide a determination of whether the body part of the target examinee captured in the acquired target medical image is normal, by using the first classification model and the second classification model that are trained by the model generation apparatus according to any of the above aspects, and an output unit configured to provide an output of a result of the determination. With this configuration, it is possible to improve accuracy of classifying medical images with relatively low costs.

As another embodiment of the model generation apparatus according to the embodiments described above and also another embodiment of the diagnostic assistance apparatus according to the embodiment described above, an aspect of the present disclosure may be an information processing method for implementing all or part of the configurations described above; a program therefor; or a storage medium storing such a program, readable by a computer, a device, a machine, and the like. Here, the storage medium readable by a computer and the like is a medium configured to store information such as programs with the use of an electrical, magnetic, optical, mechanical, or chemical effect. Further, an aspect of the present disclosure may be a diagnostic assistance system including the model generation apparatus and diagnostic assistance apparatus according to any of the embodiments.

A diagnostic assistance method according to an aspect of the present disclosure is an information processing method implemented by a computer, including acquiring a target medical image capturing a body part of a target examinee; by feeding the acquired target medical image to a trained first classification model and performing an arithmetic operation of the trained first classification model, acquiring as a first result a degree of normality evaluated by one-class classification on the body part of the target examinee captured in the target medical image, the first classification model being trained, by unsupervised learning using a plurality of first learning medical images capturing normal body parts, to provide an evaluation of a degree of normality of a body part captured in a fed medical image by one-class classification; by feeding the acquired target medical image to a trained second classification model and performing an arithmetic operation of the trained second classification model, acquiring as a second result a degree of normality evaluated on the body part of the target examinee captured in the target medical image, the second classification model being trained, by supervised learning using a plurality of learning data sets, each learning data set being a combination of a second learning medical image and a correct label indicating whether a body part captured in the second learning medical image is normal, to provide an evaluation of a degree of normality of a body part captured in a fed medical image, the second learning medical images of the plurality of learning data sets including a normal medical image capturing a normal body part and an abnormal medical image capturing an abnormal body part; in accordance with the first result and the second result, providing a determination of whether the body part of the target examinee captured in the target medical image is normal; and providing an output of a result of the determination.

A model generation method according to an aspect of the present disclosure is an information processing method including acquiring a plurality of first learning medical images capturing normal body parts; performing unsupervised learning of a first classification model by using the plurality of first learning medical images acquired, the first classification model being configured to accept an input of a medical image and provide an evaluation of a degree of normality of a body part captured in the input medical image by one-class classification, the unsupervised learning including training the first classification model such that, when an input medical image belongs to a class of the plurality of first learning medical images, a body part captured in the input medical image is evaluated as normal; when the input medical image does not belong to the class of the plurality of first learning medical images, the body part captured in the input medical image is evaluated as non-normal; acquiring a plurality of learning data sets, each learning data set being a combination of a second learning medical image and a correct label indicating whether a body part captured in the second learning medical image is normal, the second learning medical images of the plurality of learning data sets including a normal medical image capturing a normal body part and an abnormal medical image capturing an abnormal body part; and performing supervised learning of a second classification model by using the plurality of learning data sets acquired and the trained first classification model, the second classification model being configured to accept an input of a medical image and an input of a result of the evaluation on the medical image by the first classification model and provide an evaluation of a degree of normality of a body part captured in the input medical image, the supervised learning including training the second classification model such that, with respect to each learning data set, in response to an input of the second learning medical image and an input of a result of the evaluation on the second learning medical image by the first classification model, when providing an evaluation of a degree of normality on a body part captured in the input second learning medical image, a result of the evaluation matches the correct label corresponding to the second learning medical image.

The present disclosure can improve accuracy of classifying medical images with relatively low costs.

DETAILED DESCRIPTION OF THE DISCLOSURE

Hereinafter, an embodiment (also referred to as "the present embodiment" in the following) according to an aspect of the present disclosure will be described with reference to the drawings. The present embodiment described below is mere an example of the present disclosure in all respects. As might be expected, various changes and modifications can be made without departing from the range of the present disclosure. This means that, to implement the present disclosure, specific configurations according to the embodiment can also be used when appropriate. It should be noted that data is explained by a natural language in the present embodiment; but more specifically, data is specified by, for example, pseudo-languages, commands, parameters, and machine languages that can be recognizable by computers.

§ 1 APPLICATION EXAMPLE

Figure 1:
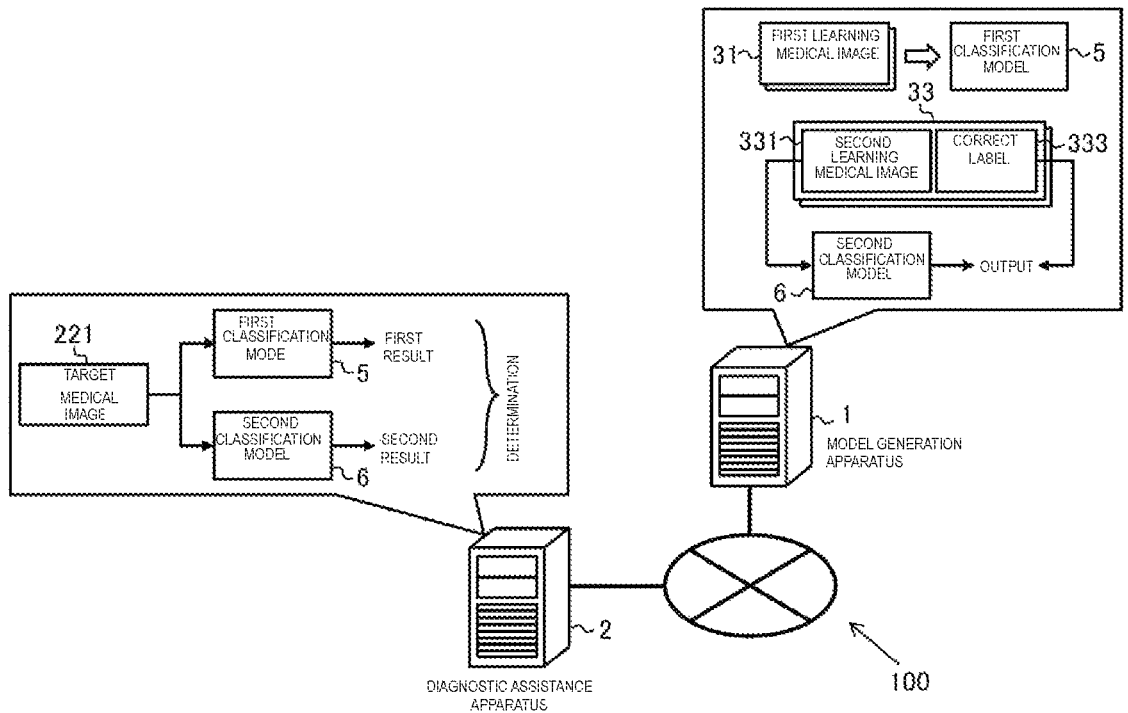
FIG. 1 schematically illustrates an example of a case using the present disclosure.

FIG. 1 schematically illustrates an example of a case using the present disclosure. A diagnostic assistance system 100 according to the present embodiment includes a model generation apparatus 1 and a diagnostic assistance apparatus 2.

The model generation apparatus 1 according to the present embodiment is a computer configured to generate a trained model by machine learning. Specifically, the model generation apparatus 1 acquires a plurality of first learning medical images 31 capturing normal body parts of subjects. The model generation apparatus 1 performs unsupervised learning, using the acquired first learning medical images 31, of a first classification model 5. The first classification model 5 is configured to evaluate by one-class classification the degree of normality of a body part captured in an accepted input medical image. One example of the evaluation of the degree of normality by one-class classification is to evaluate the distance to learning data mapped in a feature space from a linear or non-linear hyperplane. With this method, it is possible to determine whether a body part captured in a medical image is normal, for example, such that when the evaluation value of a fed medical image is relatively large, the body part captured in the medical image is determined to be abnormal; when the evaluation value is relatively small, the body part is determined to be normal. The unsupervised learning includes training the first classification model 5 in the following manner: when an input medical image belongs to the class of the first learning medical images 31, the body part captured in the input medical image is evaluated as normal; when the input medical image does not belong to the class of the first learning medical images 31, the body part captured in the input medical image is evaluated as non-normal. As the result of this training, the first classification model 5 acquires a capability to evaluate the degree of normality of a body part captured in a fed medical image by one-class classification.

The model generation apparatus 1 acquires a plurality of learning data sets 33, each being a combination of a second learning medical image 331 and a correct label 333 indicating whether a body part of the corresponding second learning medical image 331 is normal. The second learning medical images 331 of the learning data sets 33 include normal medical images capturing normal body parts and abnormal medical images capturing abnormal body parts. The model generation apparatus 1 performs supervised learning of a second classification model 6 with the acquired learning data sets 33. The second classification model 6 is configured to accept an input of a medical image and evaluate the degree of normality of a body part captured in the input medical image. The supervised learning includes training the second classification model 6 such that, with respect to each learning data set 33, in response to an input of the second learning medical image 331, when evaluating the degree of normality of a body part captured in the inputted second learning medical image 331, the evaluation result matches the correct label 333 corresponding to the second learning medical image 331. As the result of this training, the second classification model 6 acquires a capability to evaluate the degree of normality of a body part captured in a fed medical image.

As the result of performing the machine learning tasks, the model generation apparatus 1 generates the trained first classification model 5 and the trained second classification model 6.

The diagnostic assistance apparatus 2 according to the present embodiment is a computer configured to classify whether a body part of a target examinee is normal by using the trained first classification model 5 and the trained second classification model 6. Specifically, the diagnostic assistance apparatus 2 acquires a target medical image 221 capturing a body part of a target examinee. The diagnostic assistance apparatus 2 feeds the acquired target medical image 221 to the trained first classification model 5 and then performs an arithmetic operation of the trained first classification model 5. As a result, the diagnostic assistance apparatus 2 acquires as a first result the degree of normality of the body part of the target examinee captured in the target medical image 221 by evaluating the degree of normality by one-class classification. The diagnostic assistance apparatus 2 feeds the acquired target medical image 221 to the trained second classification model 6 and then performs an arithmetic operation of the trained second classification model 6. As a result, the diagnostic assistance apparatus 2 acquires as a second result the degree of normality evaluated on the body part of the target examinee captured in the target medical image 221. In accordance with the first and second results, the diagnostic assistance apparatus 2 determines whether the body part of the target examinee captured in the target medical image 221 is normal. The diagnostic assistance apparatus 2 accordingly outputs the determination result.

As described above, in the present embodiment, the model generation apparatus 1 generates the first classification model 5 trained by unsupervised learning using the first learning medical images 31 of normal cases; the model generation apparatus 1 also generates the second classification model 6 trained by supervised learning using the learning data sets 33 including normal cases and abnormal cases. By using the two generated classification models, namely the trained first classification model 5 and the trained second classification model 6, the diagnostic assistance apparatus 2 infers whether the body part of the target examinee captured in the target medical image 221 is normal. Collecting a large number of the learning data sets 33 including the second learning medical images 331 of abnormal cases is difficult and costly, whereas collecting the first learning medical images 31 of normal cases is relatively inexpensive and not very difficult. As a result, because the number of the learning data sets 33 is relatively small, the classification accuracy of the trained second classification model 6 may be relatively low. The classification capability can, however, be supplemented by the first classification model 5 trained with a large number of the first learning medical images 31 easily collected with relatively low costs. As such, the present embodiment can improve with relatively low costs the accuracy of classifying whether a body part of a target examinee captured in a medical image is normal.

It should be noted that medical images are not limited to a particular type when the medical images can be used to assist diagnoses; any type of medical images may be selected as appropriate to the embodiment. Medical images may be, for example, X-ray photographs, computed tomography (CT) images, magnetic resonance imaging (MRI) images, or ultrasound images. A body part may be all or a portion of a part covering a body region, such as the head, the chest, or the abdomen. A body part may also be all or a portion of an organ (internal organ) or tissue at a part covering a body region.

The expression "a body part is normal" may denote, for example, the case in which a person or machine reaches a diagnosis indicating that there is no lesion area or that the probability of the non-existence of a lesion area is relatively high; this means that the expression may include the case in which there is actually a lesion area. The expression "a body part is abnormal" may denote, for example, the case in which a person or machine reaches a diagnosis indicating that there is a lesion area or that the probability of the existence of a lesion area is relatively high; this means that the expression may include the case in which there is actually no lesion area.

Unsupervised learning is a machine learning method basically using learning data without correct labels. Unsupervised learning may include self-supervised learning and adversarial learning. By contrast, supervised learning is a machine learning method using learning data with correct labels (the learning data sets 33 described above).

The first result and the second result may be acquired directly or indirectly from the first classification model 5 and the second classification model 6. This means that the first classification model 5 and the second classification model 6 are respectively configured to directly output the output values respectively corresponding to the first result and the second result; alternatively, the first result and the second result may be acquired by performing a predetermined arithmetic operation (for example, threshold determination or summation of multiple numerical values) on the respective output values from the first classification model 5 and the second classification model 6.

In the example in FIG. 1, the model generation apparatus 1 and the diagnostic assistance apparatus 2 are connected to each other through a network. The type of the network may be selected as appropriate from, for example, the Internet, a wireless communication network, a mobile communication network, a telephone network, and a dedicated network. The method for exchanging data between the model generation apparatus 1 and the diagnostic assistance apparatus 2 is not necessarily limited to this example, and any method may be selected as appropriate to the embodiment. For example, a storage medium may be used to exchange data between the model generation apparatus 1 and the diagnostic assistance apparatus 2.

In the example in FIG. 1, the model generation apparatus 1 and the diagnostic assistance apparatus 2 are implemented by discrete computers. The configuration of the diagnostic assistance system 100 according to the present embodiment, however, is not necessarily limited to this example, and the configuration can be determined as appropriate to the embodiment. For example, the model generation apparatus 1 and the diagnostic assistance apparatus 2 may be integrated into a single computer. Alternatively, for example, at least one of the model generation apparatus 1 and the diagnostic assistance apparatus 2 may be implemented by a plurality of computers.

§ 2 CONFIGURATION EXAMPLE

[Hardware Configuration]
<Model Generation Apparatus>

Figure 2:
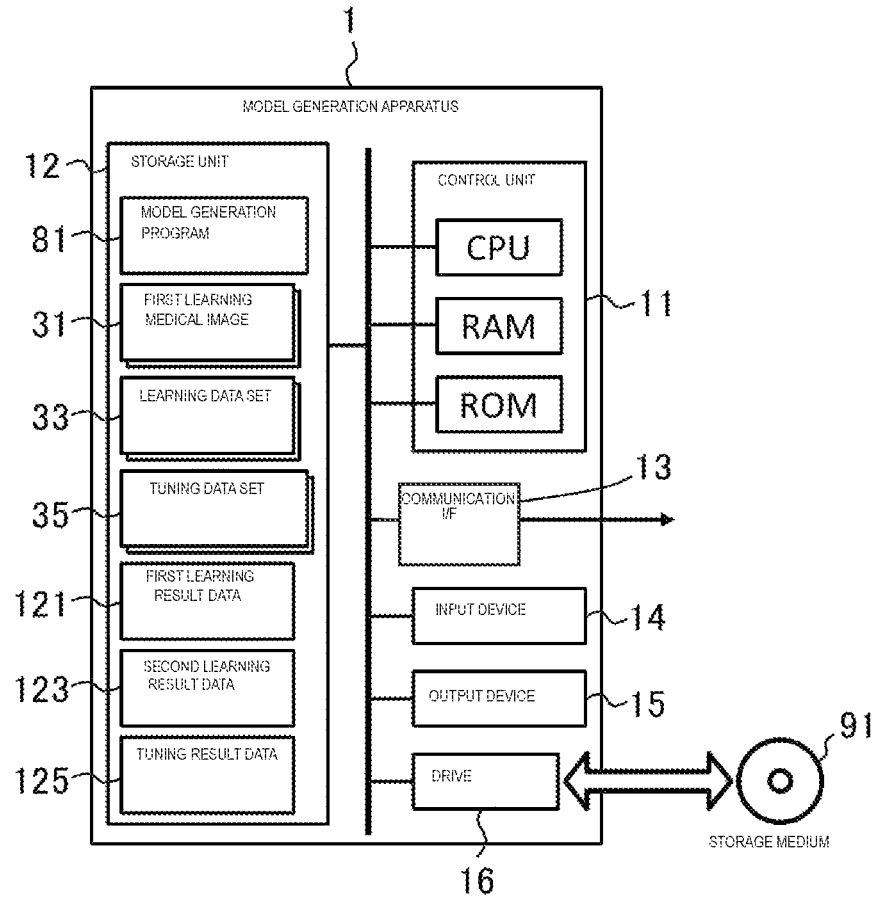
FIG. 2 schematically illustrates an example of a hardware configuration of a model generation apparatus according to an embodiment.

FIG. 2 schematically illustrates an example of a hardware configuration of the model generation apparatus 1 according to the present embodiment. As illustrated in FIG. 2, the model generation apparatus 1 according to the present embodiment is a computer including a control unit 11, a storage unit 12, a communication interface 13, an input device 14, an output device 15, and a drive 16 that are electrically connected. In FIG. 2, the communication interface is referred to as "communication I/F". The same reference holds for FIG. 3 described later.

The control unit 11 includes, for example, a central processing unit (CPU), a random-access memory (RAM), and a read-only memory (ROM) as hardware processors. The control unit 11 is configured to perform information processing tasks based on programs and various kinds of data. The CPU is an example of processor resources. The storage unit 12 is an example of memory resources. The storage unit 12 may be implemented by, for example, a hard disk drive or a solid state drive. In the present embodiment, the storage unit 12 stores various kinds of information including a model generation program 81, the first learning medical images 31, the learning data sets 33, tuning data sets 35, first learning result data 121, second learning result data 123, and tuning result data 125.

The model generation program 81 is configured to cause the model generation apparatus 1 to perform information processing operations described later (FIGS. 7 to 10), regarding machine learning of the classification models (5, 6). The model generation program 81 contains a series of instructions for the information processing operation. The first learning medical images 31 are used for machine learning of the first classification model 5. The learning data sets 33 are used for machine learning of the second classification model 6. The plurality of tuning data sets 35 are used to tune the value of a first parameter, which determines the priority level of the first result, and the value of a second parameter, which determines the priority level of the second result. The first learning result data 121 indicates information about a result of machine learning of the first classification model 5. The second learning result data 123 indicates information about a result of machine learning of the second classification model 6. The tuning result data 125 indicates information about a result of tuning values of the parameter. In the present embodiment, the first learning result data 121, the second learning result data 123, and the tuning result data 125 are generated by running the model generation program 81.

The communication interface 13, which is, for example, a wired local area network (LAN) module or wireless LAN module, is an interface for wired or wireless communications using a network. By using the communication interface 13, the model generation apparatus 1 may perform data communication with another information processing apparatus through a network.

The input device 14 is a device for input operation, such as a mouse and a keyboard. The output device 15 is a device for output operation, such as a display (display device) and a speaker. The input device 14 and the output device 15 may be implemented by a single device such as a touch panel display. An operator such as the user can operate the model generation apparatus 1 by using the input device 14 and the output device 15.

The drive 16, which may be, for example, a compact disc (CD) drive or a digital versatile disc (DVD) drive, is a drive device for reading various kinds of information, such as programs, stored in a storage medium 91. The storage medium 91 is a medium configured to store various kinds of information such as programs with the use of an electrical, magnetic, optical, mechanical, or chemical effect in such a manner that a computer, a device, a machine, and the like can read the information such as programs. The storage medium 91 may store at least any of the model generation program 81, the first learning medical images 31, the learning data sets 33, and the tuning data sets 35. In this case, the model generation apparatus 1 may acquire at least any of these from the storage medium 91. In FIG. 2, a disc storage medium, such as a CD or DVD, is illustrated as an example of the storage medium 91. The type of the storage medium 91, however, is not necessarily limited to disc, and may be any types other than disc. Examples of types of storage medium other than disc include semiconductor memories, such as a flash memory. Any type of drive may be selected as the drive 16 in accordance with the type of the storage medium 91.

Regarding the model generation apparatus 1, constituent elements may be excluded, replaced, or added as appropriate to the embodiment. For example, processor resources may include a plurality of hardware processors. The hardware processors may be, for example, a microprocessor, a field-programmable gate array (FPGA), and a graphics processing unit (GPU). The storage unit 12 may be implemented by the RAM and ROM included in the control unit 11. At least any of the communication interface 13, the input device 14, the output device 15, and the drive 16 is not necessarily provided. The model generation apparatus 1 may be implemented by a plurality of computers. In this case, the computers may be identical to or different from each other with respect to hardware configuration. The model generation apparatus 1 may be an information processing apparatus designed especially for a service provided, or may be a general-purpose server device or a personal computer (PC).

<Diagnostic Assistance Apparatus>

Figure 3:
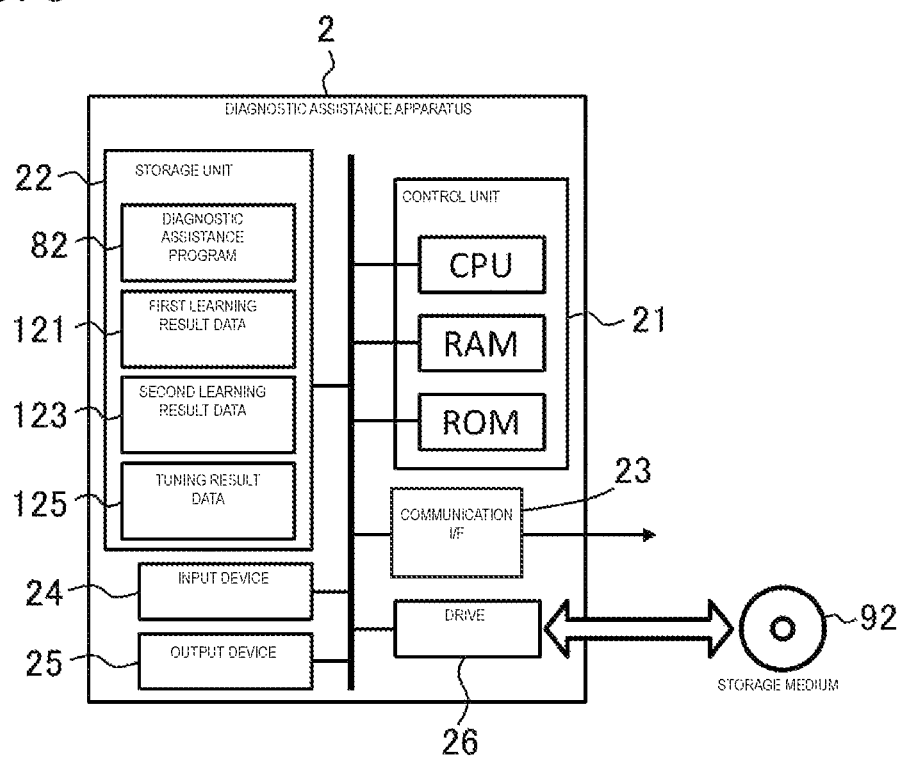
FIG. 3 schematically illustrates an example of a hardware configuration of a diagnostic assistance apparatus according to the embodiment.

FIG. 3 schematically illustrates an example of a hardware configuration of the diagnostic assistance apparatus 2 according to the present embodiment. As illustrated in FIG. 3, the diagnostic assistance apparatus 2 according to the present embodiment is a computer including a control unit 21, a storage unit 22, a communication interface 23, an input device 24, an output device 25, and a drive 26 that are electrically connected.

The control unit 21 to the drive 26 of the diagnostic assistance apparatus 2 and a storage medium 92 may be respectively configured in the same manner as the control unit 11 to the drive 16 of the model generation apparatus 1 and the storage medium 91. The control unit 21 includes, for example, a CPU, a RAM, and a ROM as hardware processors. The control unit 21 is configured to perform various information processing tasks based on programs and data. The storage unit 22 may be implemented by, for example, a hard disk drive or a solid state drive. The storage unit 22 stores various kinds of information including a diagnostic assistance program 82, the first learning result data 121, the second learning result data 123, and the tuning result data 125.

Figure 11:
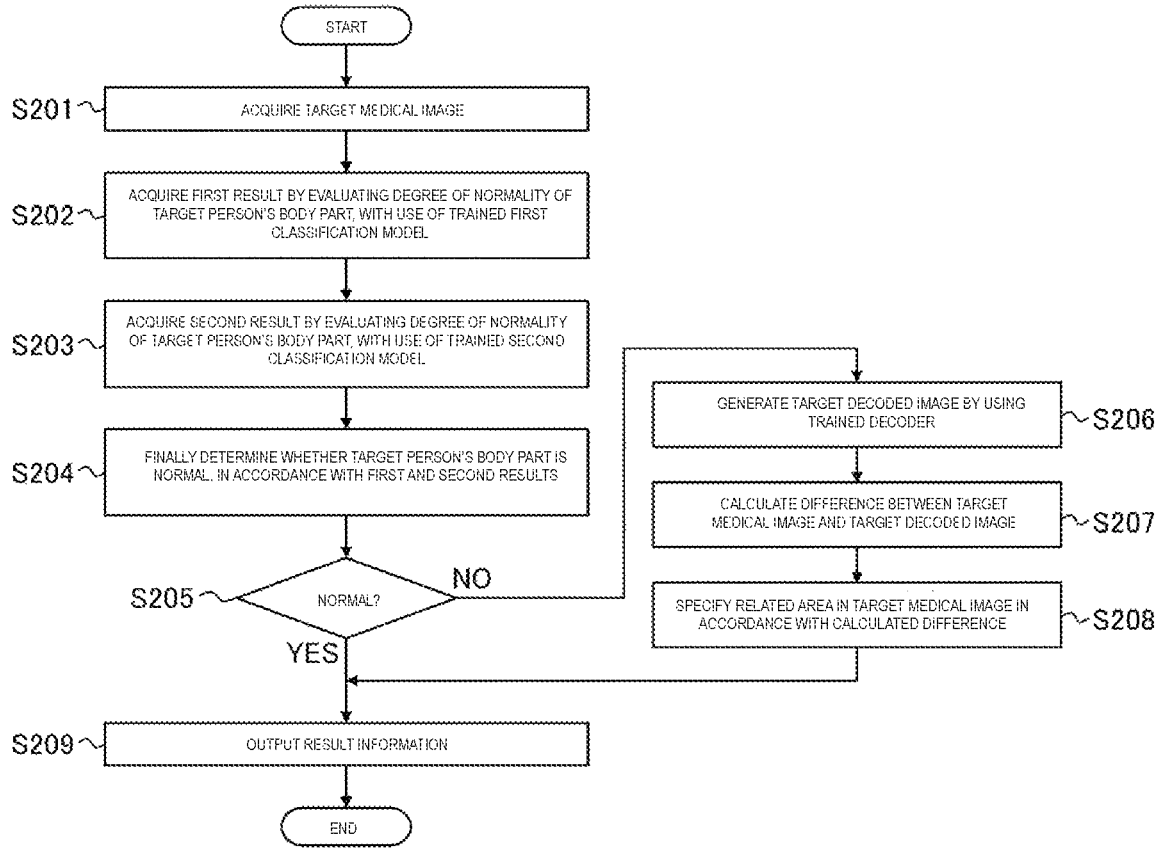
FIG. 11 is a flowchart illustrating an example of a procedure of the diagnostic assistance apparatus according to the embodiment.

The diagnostic assistance program 82 is configured to cause the diagnostic assistance apparatus 2 to perform an information processing operation for classifying whether a body part of a target examinee is normal by using the trained first classification model 5 and the trained second classification model 6, which will be described later (FIG. 11). The diagnostic assistance program 82 contains a series of instructions for the information processing operation. The storage medium 92 may store at least any of the diagnostic assistance program 82, the first learning result data 121, the second learning result data 123, and the tuning result data 125. The diagnostic assistance apparatus 2 may accordingly acquire at least any of these from the storage medium 92.

Regarding the specific hardware configuration of the diagnostic assistance apparatus 2, constituent elements may be excluded, replaced, or added as appropriate to the embodiment. For example, processor resources of the diagnostic assistance apparatus 2 may include a plurality of hardware processors. The hardware processors may be, for example, a microprocessor, an FPGA, and a GPU. The storage unit 22 may be implemented by the RAM and ROM included in the control unit 21. At least any of the communication interface 23, the input device 24, the output device 25, and the drive 26 is not necessarily provided. The diagnostic assistance apparatus 2 may be implemented by a plurality of computers. In this case, the computers may be identical to or different from each other with respect to hardware configuration. The diagnostic assistance apparatus 2 may be an information processing apparatus designed especially for a service provided, or may be a general-purpose server device or a general-purpose PC.

[Software Configuration]

<Model Generation Apparatus>

Figure 4:
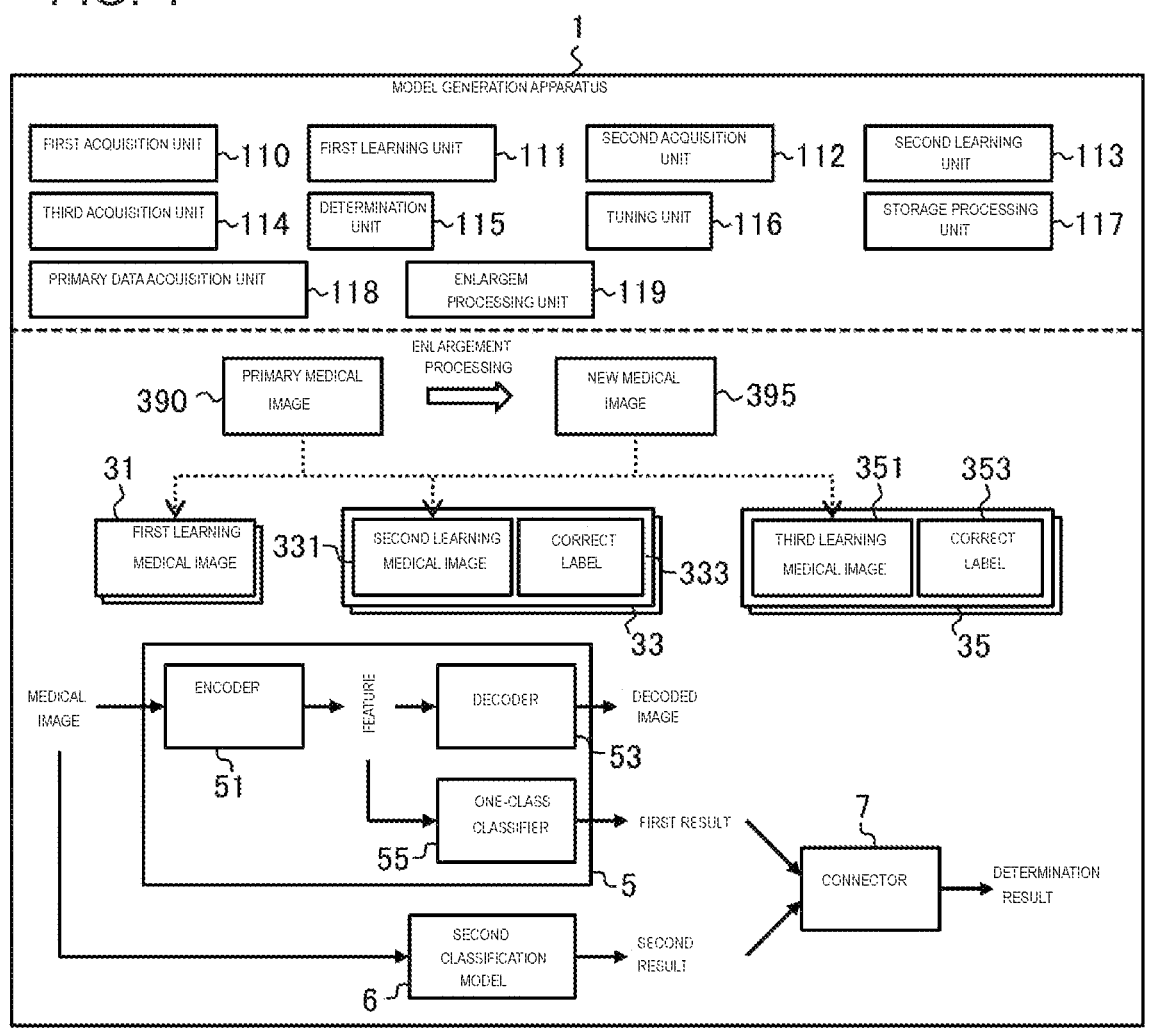
FIG. 4 schematically illustrates an example of a software configuration of the model generation apparatus according to the embodiment.
Figure 5A:
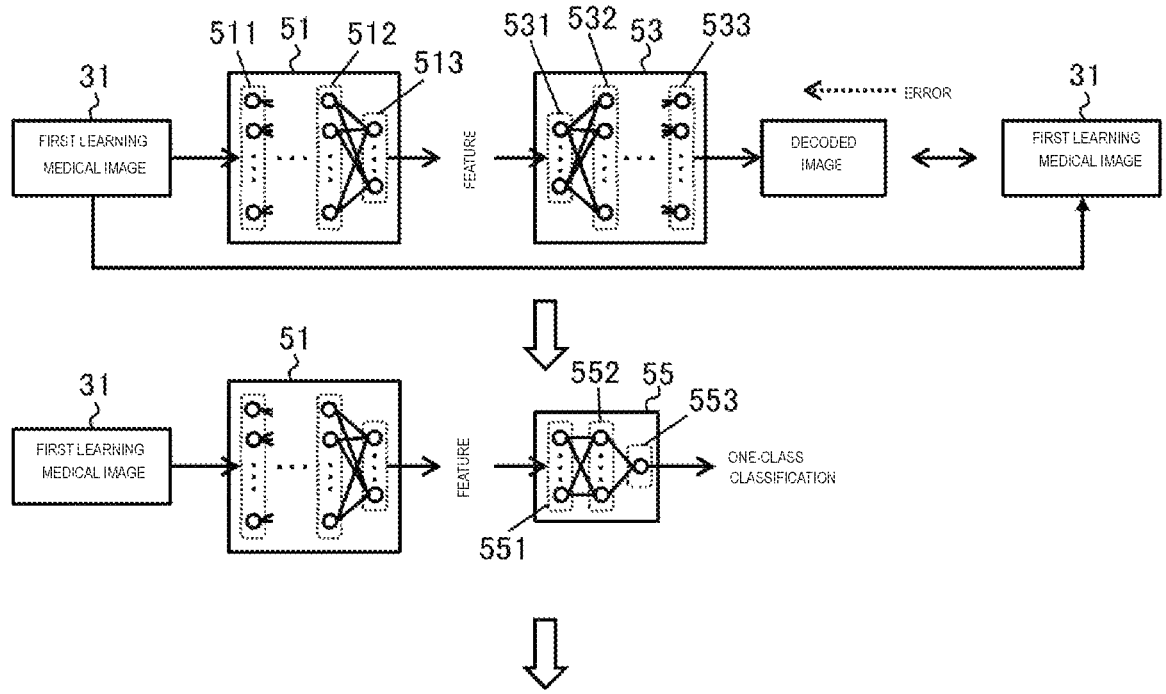
FIG. 5A schematically illustrates an example of an unsupervised learning process of a first classification model by the model generation apparatus according to the embodiment.
Figure 5B:
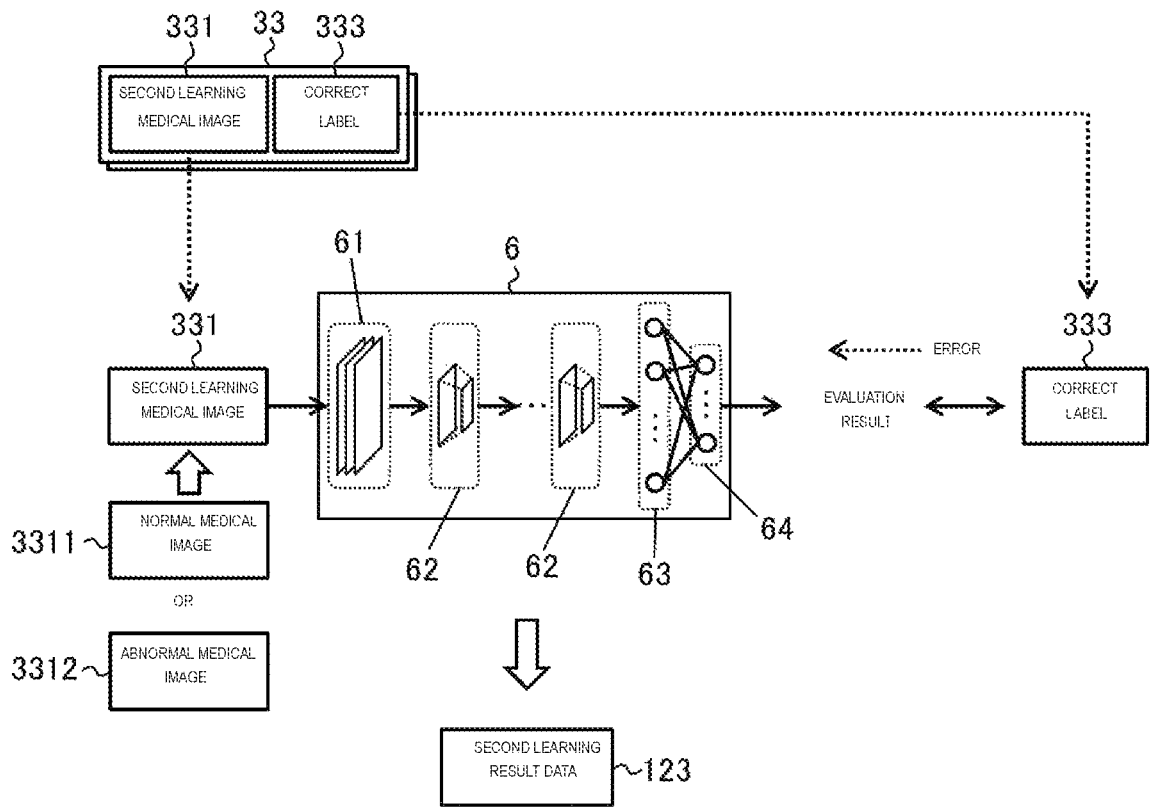
FIG. 5B schematically illustrates an example of a supervised learning process of a second classification model by the model generation apparatus according to the embodiment.
Figure 5C:
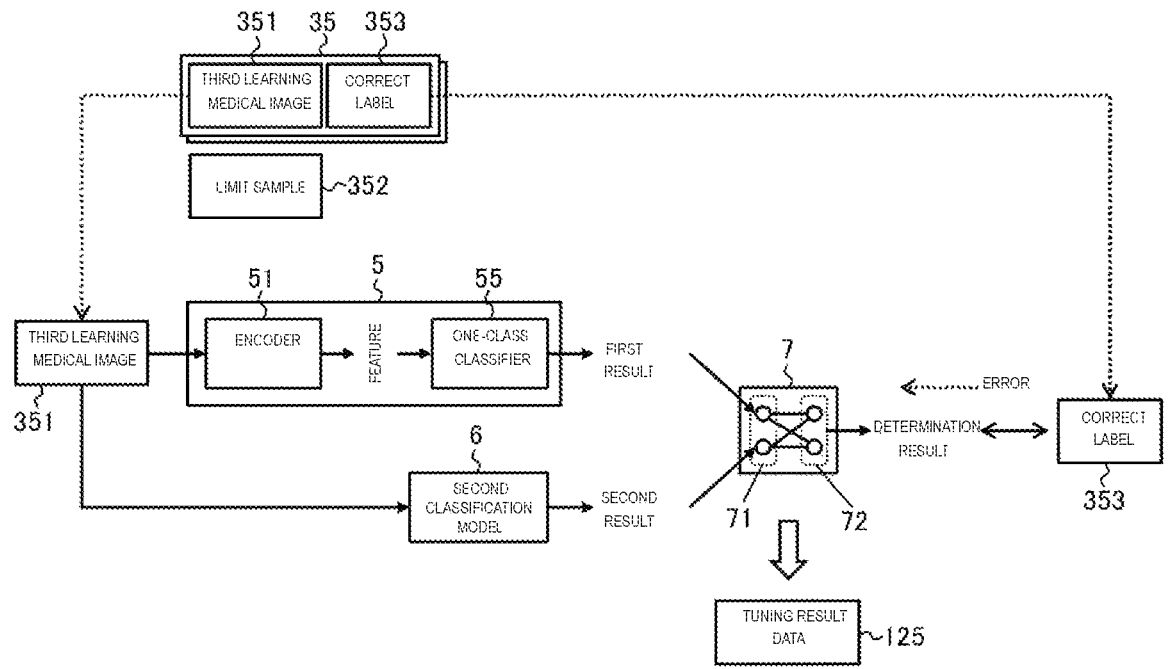
FIG. 5C schematically illustrates an example of a parameter tuning process by the model generation apparatus according to the embodiment.

FIG. 4 schematically illustrates an example of a software configuration of the model generation apparatus 1 according to the present embodiment. FIG. 5A schematically illustrates an example of an unsupervised learning process of the first classification model 5. FIG. 5B schematically illustrates an example of a supervised learning process of the second classification model 6. FIG. 5C schematically illustrates an example of a process of tuning the value of the first parameter and the value of the second parameter.

The control unit 11 of the model generation apparatus 1 loads into the RAM the model generation program 81 stored in the storage unit 12. The control unit 11 controls individual units by using the CPU understanding and executing the instructions contained in the model generation program 81 loaded in the RAM. Accordingly, as illustrated in FIG. 4, the model generation apparatus 1 according to the present embodiment operates as a computer including software modules of a first acquisition unit 110, a first learning unit 111, a second acquisition unit 112, a second learning unit 113, a third acquisition unit 114, a determination unit 115, a tuning unit 116, a storage processing unit 117, a primary data acquisition unit 118, and an enlargement processing unit 119. This means that in the present embodiment the control unit 11 (CPU) implements the software modules.

The first acquisition unit 110 acquires the first learning medical images 31 capturing normal body parts of subjects. By using the acquired first learning medical images 31, the first learning unit 111 performs unsupervised learning of the first classification model 5. The first classification model 5 is configured to accept an input of a medical image and output an output value corresponding to a result of classifying by one-class classification whether a body part captured in the input medical image is normal. The unsupervised learning includes training the first classification model 5 in the following manner: when an input medical image belongs to the class of the first learning medical images 31, the body part captured in the input medical image is classified as normal; when the input medical image does not belong to the class of the first learning medical images 31, the body part captured in the input medical image is classified as non-normal. The configuration of the first classification model 5 and the method of unsupervised learning are not limited when the first classification model 5 can be trained in this manner, and any configuration and method may be selected as appropriate to the embodiment.

As illustrated in FIG. 4, in the present embodiment, the first classification model 5 includes an encoder 51 and a decoder 53. The encoder 51 is configured to convert a fed medical image into features (extract features from a medical image). In other words, the encoder 51 is configured to accept an input of a medical image and output an output value corresponding to a result of converting the input medical image into features. The decoder 53 is configured to acquire by decoding a medical image from features acquired by the encoder 51. In other words, the decoder 53 is configured to accept input features and output a result (a decoded image) of acquiring an original medical image from the input features. The unsupervised learning includes training the encoder 51 and the decoder 53 such that, when each first learning medical image 31 is fed to the encoder 51, a decoded image responsively generated by the decoder 53 matches the first learning medical image 31. This means that in the unsupervised learning the encoder 51 and the decoder 53 are trained to minimize reconstruction errors between the first learning medical images 31 and the corresponding decoded images.

In the present embodiment, the first classification model 5 further includes a one-class classifier 55. The one-class classifier 55 is configured to accept input features acquired by the encoder 51 and output an output value corresponding to a result of evaluating the degree of normality of a body part captured in the medical image by one-class classification in accordance with the input features. The unsupervised learning further includes training the one-class classifier 55 to provide evaluation by one-class classification in accordance with features acquired by the encoder 51. In other words, the unsupervised learning includes training the one-class classifier 55 in the following manner: when input features belong to the class of features learned by the trained encoder 51 from the input first learning medical images 31, a body part captured in the fed medical image is evaluated as normal; when input features do not belong to the class of the learned features, a body part captured in the fed medical image is evaluated as non-normal.

The second acquisition unit 112 acquires the plurality of learning data sets 33, each being a combination of the second learning medical image 331 and the correct label 333 indicating whether a body part of the corresponding second learning medical image 331 is normal. The data format of the correct label 333 may be determined as appropriate to the embodiment. For example, the correct label 333 may be configured to use two values to indicate whether it is normal or not, or use two or more values to indicate abnormal categories (including normal case). As illustrated in FIG. 5B, the second learning medical images 331 of the learning data sets 33 include normal medical images 3311 capturing normal body parts of subjects and abnormal medical images 3312 capturing abnormal body parts of subjects. The second classification model 6 is configured to accept an input of a medical image and output an output value corresponding to a result of evaluating the degree of normality of a body part captured in the input medical image. The second learning unit 113 performs supervised learning of the second classification model 6 with the acquired learning data sets 33. The supervised learning includes training the second classification model 6 such that, with respect to each learning data set 33, in response to an input of the second learning medical image 331, when evaluating the degree of normality of a body part captured in the inputted second learning medical image 331, the evaluation result matches the correct label 333 corresponding to the second learning medical image 331.

The third acquisition unit 114 acquires a plurality of third learning medical images 351 capturing body parts having been determined to be normal or non-normal. The method of determining whether a body part captured in the third learning medical image 351 is normal may be determined as appropriate to the embodiment. In the present embodiment, similarly to the second learning medical image 331, the third learning medical image 351 is labelled with a correct label 353. The correct label 353 is configured to indicate whether a body part captured in the corresponding third learning medical image 351 is normal. Specifically, the third acquisition unit 114 acquires the plurality of tuning data sets 35, each being a combination of the third learning medical image 351 and the correct label 353.

The determination unit 115 determines, with the trained first classification model 5 and the trained second classification model 6, whether a body part captured in each third learning medical image 351 acquired is normal. Specifically, by feeding the third learning medical images 351 to the trained first classification model 5, the determination unit 115 acquires as the first result the degree of normality of a body part captured in each third learning medical image 351 by evaluating the degree of normality by one-class classification. By feeding the third learning medical images 351 to the trained second classification model 6, the determination unit 115 acquires as the second result the degree of normality of a body part captured in each third learning medical image 351 by evaluating the degree of normality. In the present embodiment, the first result and the second result are configured to indicate the degree of normality of a body part by a numerical value. Indicating the degree of normality with a numerical value may be implemented by at least either directly indicating the degree of normality or indirectly indicating the degree of normality by indicating the degree of abnormality. This means that the first result and the second result may be indicated by at least either a numerical value indicating the degree of normality or a numerical value indicating the degree of abnormality. The degree may be represented by, for example, probability or index. The determination unit 115 includes a connector 7 having the first parameter, which determines the priority level of the first result, and the second parameter, which determines the priority level of the second result. The determination unit 115 feeds the acquired first result and the acquired second result to the connector 7 and weight the first result and the second result with the first parameter and the second parameter. The determination unit 115 connects the weighted first result and the weighted second result. The determination unit 115 compares the numerical value acquired by the connection (determination value) to a threshold to determine whether a body part captured in each third learning medical image 351 is normal. The tuning unit 116 tunes the first parameter and the second parameter to optimize the accuracy of determination by the determination unit 115 on the third learning medical images 351. As illustrated in FIG. 5C, the third learning medical images 351 may include one or a plurality of limit samples (may also referred to as "limit medical images") 352. All the third learning medical images 351 may be the limit samples 352. In this case, the tuning unit 116 may tune the first parameter and the second parameter to avoid incorrect determination by the determination unit 115 about all the one or plurality of limit samples 352.

As illustrated in FIGS. 5A to 5C, the storage processing unit 117 generates information about results of the machine learning tasks and parameter tuning. The storage processing unit 117 generates information about the trained first classification model 5 as the first learning result data 121. The storage processing unit 117 generates information about the trained second classification model 6 as the second learning result data 123. The storage processing unit 117 generates information about the tuned connector 7 as the tuning result data 125. The storage processing unit 117 stores the generated first learning result data 121, the generated second learning result data 123, and the generated tuning result data 125 in a predetermined storage area.

The primary data acquisition unit 118 acquires one or a plurality of primary medical images 390 capturing body parts of subjects. The enlargement processing unit 119 performs enlargement processing on the primary medical image 390 to generate a new medical image 395. The enlargement processing is generating the new medical image 395 different from the primary medical image 390 by an image processing operation such as parallel translation, while maintaining at least a portion of the collection of features captured in the primary medical image 390.

At least a portion of the collection of the learning medical images (31, 331, 351) may be constituted by at least either the primary medical images 390 or the new medical images 395. Medical images other than the primary medical image 390 and the new medical image 395, acquired individually, may be used as the learning medical images (31, 331, 351). The primary medical image 390 and the learning medical images (31, 331, 351) are medical images formed by capturing an image of a subject's body part by using an imaging device, such as an X-ray imaging device, a computed tomographic imaging device, or a magnetic resonance tomographic imaging device. The number of subjects for collection of each kind of images may be determined in any manner. The subject may include a model representing a human body (for example, a phantom for X-ray imaging).

(Example of First Classification Model Configuration)

The encoder 51, the decoder 53, and the one-class classifier 55 are implemented by machine learning models having operational parameters. The machine learning model for each purpose is not limited to a particular type when the machine learning model can carry out the corresponding arithmetic operation; any type of machine learning model may be selected as appropriate to the embodiment.

As illustrated in FIG. 5A, in the present embodiment, fully connected neural networks are used as the encoder 51, the decoder 53, and the one-class classifier 55. Each of the encoder 51, the decoder 53, and the one-class classifier 55 has an input layer (511, 531, 551), intermediate (hidden) layers (512, 532, 552), and an output layer (513, 533, 553). The number of intermediate layers (512, 532, 552) may be determined as appropriate to the embodiment. The architecture of each network is not limited to this example, and may be determined as appropriate to the embodiment. For example, the intermediate layers (512, 532, 552) may be excluded. For example, each network may include another kind of layer such as a convolutional layer.

Each layer (511 to 513, 531 to 533, 551 to 553) contains one or a plurality of neurons (nodes). The number of neurons included in each layer may be determined as appropriate to the embodiment. For example, the number of neurons included in the input layer (511, 531, 551) and the number of neurons included in the output layer (513, 533, 553) may be determined depending on the dimensions of input and output data. Specifically, for example, the number of neurons included in the input layer 511 of the encoder 51 and the number of neurons included in the output layer 533 of the decoder 53 may be determined depending on the number of picture elements of the medical image. The number of neurons included in the input layers (531, 551) of the decoder 53 and the one-class classifier 55 may be determined depending on the number of neurons included in the output layer 513 of the encoder 51. The number of neurons included in the output layer 553 of the one-class classifier 55 may be determined to be a particular number (for example, one), depending on the type of the result of one-class classification.

Neurons in adjacent layers are connected to each other as appropriate. In the example in FIG. 5A, all neurons are connected to each other between adjacent layers. The connection of neurons, however, is not limited to this example, and the connection can be set as appropriate to the embodiment. A weight (connection weight) is assigned to each connection. A threshold is set for each neuron. The output of a neuron is basically determined by whether the sum of products of each input and a corresponding weight exceeds a threshold. The threshold may be expressed by an activation function. In this case, the output of each neuron is determined by inputting the sum of products of each input and a corresponding weight to the activation function and calculating the activation function. The activation function is not limited to a particular type, and any type of activation function may be selected as appropriate to the embodiment. The weight of connection between neurons in different layers and the threshold of each neuron are examples of operational parameters used in corresponding arithmetic operations.

The operational parameters of the elements of the first classification model 5 are tuned in the process of unsupervised learning to achieve a desired capability. Firstly, the first learning unit 111 inputs each first learning medical image 31 to the input layer 511 of the encoder 51 and performs an arithmetic operation of forward propagation of the encoder 51 and the decoder 53. The arithmetic operation of forward propagation is determining whether each neuron included in each layer is fired, consecutively from the input side. As the result of the arithmetic operation of forward propagation of the encoder 51, features (corresponding output values) extracted from the first learning medical image 31 can be acquired from the output layer 513 of the encoder 51. Subsequently, as the result of the arithmetic operation of forward propagation of the decoder 53, a decoded image (corresponding output values) generated based on the features in response to the first learning medical image 31 can be acquired from the output layer 533 of the decoder 53. The first learning unit 111 tunes the operational parameters of the encoder 51 and the decoder 53 to reduce errors (reconstruction errors) between the first learning medical images 31 and the corresponding decoded images. Consequently, the trained encoder 51 and the trained decoder 53 are generated.

Secondly, the first learning unit 111 inputs each first learning medical image 31 to the input layer 511 of the trained encoder 51 and performs the arithmetic operation of forward propagation of the encoder 51 and the one-class classifier 55. As the result of the arithmetic operation of forward propagation of the one-class classifier 55, an output value corresponding to a result of evaluating the degree of normality of a body part captured in each first learning medical image 31 can be acquired from the output layer 553 of the one-class classifier 55. For example, the output value represents a distance from the origin of a feature space. The first learning unit 111 tunes the operational parameters of the one-class classifier 55 to maximize the distance from the origin. Consequently, the trained one-class classifier 55 with a maximized margin of classification boundary is generated.

The storage processing unit 117 generates as the first learning result data 121 information indicating the architecture and operational parameters of each element of the trained first classification model 5 generated by the unsupervised learning described above. The architecture may be specified by, for example, the number of layers from the input layer to the output layer in a neural network, the type of each layer, the number of neurons included in each layer, and the connection between neurons in adjacent layers. When the same model architecture is used in the system, the information about architecture may be excluded from the first learning result data 121. The storage processing unit 117 stores the generated first learning result data 121 in a predetermined storage area.

(Example of Second Classification Model Configuration)

Similarly to the first classification model 5, the second classification model 6 is implemented by a machine learning model having operational parameters. The machine learning model for the second classification model 6 is not limited to a particular type when the machine learning model can carry out the arithmetic operation of evaluating the degree of normality of a body part captured in a medical image; any type of machine learning model may be selected as appropriate to the embodiment.

As illustrated in FIG. 5B, in the present embodiment, a convolutional neural network is used for the second classification model 6. The second classification model 6 has a convolutional layer 61, pooling layers 62, and fully connected layers (63, 64). The convolutional layer 61 is configured to perform convolution operation on fed data. Convolution operation corresponds to an operation of calculating a correlation between fed data and a given filter. For example, by performing convolution operation on an image, a grayscale pattern similar to the grayscale pattern of a particular filter can be detected in the image. The convolutional layer 61 has a neuron (node) corresponding to this convolution operation; the neuron (node) is connected to the input or an area of the output of a layer before (on the input side with respect to) the convolutional layer 61. The pooling layers 62 are configured to perform pooling. Pooling eliminates part of information about positions relatively strongly activated in fed data by a filter to achieve translation invariance regardless of minor changes in the position of features in the data. In pooling, for example, the maximum value in a filter may be extracted, while other values are deleted. The fully connected layers (63, 64) are configured in the same manner as the layers (511 to 513, 531 to 533, 551 to 553) in the fully connected neural networks described above.

The number of the layers 61 to 64 included in the second classification model 6 may be determined as appropriate to the embodiment. The arrangement of the convolutional layer 61 and the pooling layers 62 may be determined as appropriate to the embodiment. In the example in FIG. 5B, the convolutional layer 61 is arranged on the side closest to input (left side in the diagram); the fully connected layers (63, 64) are arranged on the side closest to output (right side in the diagram); and the pooling layers 62 is arranged before the fully connected layer 63. As a result, the convolutional layer 61 on the side closest to input forms the input layer, and the fully connected layer 64 forms the output layer. The convolutional layer 61 and the pooling layer 62 may be arranged in an alternating manner. The architecture of the second classification model 6, however, is not necessarily limited to this example. For example, a plurality of convolutional layers 61 are consecutively arranged, followed by one or a plurality of pooling layers 62. The types of layers included in the second classification model 6 are not necessarily limited to the layer types described above. The second classification model 6 may include other kinds of layers such as normalization layer and dropout layer.

The number of neurons included in the fully connected layers (63, 64) may be determined as appropriate to the embodiment. For example, the number of neurons included in the fully connected layer 64 forming the output layer may be determined depending on the type of evaluation by the second classification model 6. The evaluation by the second classification model 6 may include, for example, classifying whether it is normal and distinguishing abnormal categories (that is, types). For example, when the fully connected layer 64 directly outputs an output value representing the degree of normality of a body part, the number of neurons included in the fully connected layer 64 may be one. Alternatively, when the fully connected layer 64 outputs output values representing the degree of normality and the degree of abnormality, the number of neurons included in the fully connected layer 64 may be two. Alternatively, when the fully connected layer 64 outputs output values representing the degree of abnormal categories (including normal case), the number of neurons included in the fully connected layer 64 may be determined depending on the categories. In this case, the degree of abnormality may be given by summing output values of the abnormal categories.

Similarly to the first classification model 5, a weight (connection weight) is assigned to each connection in the convolutional layer 61 and the fully connected layers (63, 64). The threshold (or activation function) of each neuron can be given as appropriate. The weight of connection between neurons in the convolutional layer 61 and the fully connected layers (63, 64) and the threshold of each neuron are examples of operational parameters used for the arithmetic operation of the second classification model 6.

The operational parameters of the elements of the second classification model 6 are tuned in the process of supervised learning to achieve a desired capability. The second learning unit 113 inputs the second learning medical image 331 of each learning data set 33 to the input layer (the convolutional layer 61 on the side closest to input) of the second classification model 6 and performs the arithmetic operation of forward propagation of the second classification model 6. As the result of this arithmetic operation, an output value corresponding to a result of evaluating the degree of normality of a body part captured in each second learning medical image 331 can be acquired from the output layer (the fully connected layer 64). The second learning unit 113 calculates errors between the evaluation result acquired from the output layer and the correct result indicated by the correct label 333 with respect to the individual learning data set 33. The second learning unit 113 accordingly tunes the operational parameters of the second classification model 6 to reduce the calculated errors. Consequently, the trained second classification model 6 is generated.

The storage processing unit 117 generates as the second learning result data 123 information indicating the architecture and operational parameters of the trained second classification model 6 generated by the supervised learning described above. Similarly to the first learning result data 121, when the same model architecture is used in the system, the information about architecture of the second classification model 6 may be excluded from the second learning result data 123. The storage processing unit 117 stores the generated second learning result data 123 in a predetermined storage area.

(Connector)

The configuration of the connector 7 is not limited to a particular configuration when the connector 7 can perform the arithmetic operation of weighting and connecting the first result and the second result to acquire a final determination result indicating whether a body part captured in a medical image is normal; the configuration of the connector 7 may be determined as appropriate to the embodiment.

As illustrated in FIG. 5C, a two-layer fully connected neural network is used as the connector 7. The connector 7 has an input layer 71 and an output layer 72. The architecture of the connector 7 is not limited to this example, and may be determined as appropriate to the embodiment. For example, the connector 7 may be implemented by a fully connected neural network having three or more layers.

Each layer (71, 72) contains one or a plurality of neurons (nodes). The number of neurons included in the layers (71, 72) may be determined as appropriate to the embodiment. For example, the number of neurons included in the input layer 71 may be determined depending on the dimensions of data of the results. For example, the number of neurons included in the output layer 72 may be determined depending on the dimensions of data of the final determination result. The output method of the output layer 72 may be determined as appropriate to the embodiment. For example, the output layer 72 may be configured to output a determination value (that is, a result of connecting the weighted first result and the weighted second result) for deriving a determination result by comparing the determination value to a threshold, or output an output value directly representing the determination result. When the output value of the output layer 72 indicates a determination value, the arithmetic operation of forward propagation of the connector 7 can be construed as including both an operation corresponding to individually weighting the first result and the second result and an operation corresponding to connecting the weighted first result and the weighted second result. When the output value of the output layer 72 directly represents a determination result, the arithmetic operation of forward propagation of the connector 7 can be construed as including an operation corresponding to individually weighting the first result and the second result, an operation corresponding to connecting the weighted first result and the weighted second result, and an operation corresponding to comparing the determination value acquired by the connection operation to a threshold.

The connections between neurons may be set as appropriate to the embodiment. Similarly to the first classification model 5, a weight (connection weight) is assigned to each connection between the layers (71, 72). The threshold (or activation function) of each neuron can be given as appropriate. The weight of connection between neurons and the threshold of each neuron that relate to the operation of the first result are examples of the first parameter. The weight of connection between neurons and the threshold of each neuron that relate to the operation of the second result are examples of the second parameter.

In the present embodiment, the parameters are tuned by machine learning using the plurality of tuning data sets 35. Specifically, the determination unit 115 inputs the third learning medical image 351 of each tuning data set 35 to the encoder 51 of the trained first classification model 5 and performs the arithmetic operation of forward propagation of the encoder 51 and the one-class classifier 55 of the trained first classification model 5. By performing this arithmetic operation, the determination unit 115 acquires the first result of each third learning medical image 351 from the one-class classifier 55. The determination unit 115 also inputs the third learning medical image 351 of each tuning data set 35 to the trained second classification model 6 and performs the arithmetic operation of forward propagation of the second classification model 6. By performing this arithmetic operation, the determination unit 115 acquires the second result of each third learning medical image 351 from the second classification model 6. The determination unit 115 subsequently inputs the acquired first and second results to the input layer 71 of the connector 7 and performs the arithmetic operation of forward propagation of the connector 7. By performing this arithmetic operation, a determination value or an output value corresponding to a determination result can be acquired from the output layer 72 of the connector 7. The tuning unit 116 calculates errors between a determination result derived from a determination value or represented by an output value and a correct result indicated by the correct label 353 with respect to the individual tuning data sets 35. The tuning unit 116 accordingly tunes the parameters of the connector 7 to reduce the calculated errors. When the third learning medical images 351 include one or a plurality of limit samples 352, the tuning unit 116 tunes the operational parameters of the connector 7 to eliminate errors of determination results of the limit samples 352. Consequently, the tuned connector 7 is generated.

The storage processing unit 117 generates as the tuning result data 125 information indicating the architecture and parameters of the tuned connector 7 generated by the machine learning described above. Similarly to, for example, the first learning result data 121, when the same model architecture is used in the system, the information about architecture of the connector 7 may be excluded from the tuning result data 125. The storage processing unit 117 stores the generated tuning result data 125 in a predetermined storage area.

<Diagnostic Assistance Apparatus>

Figure 6:
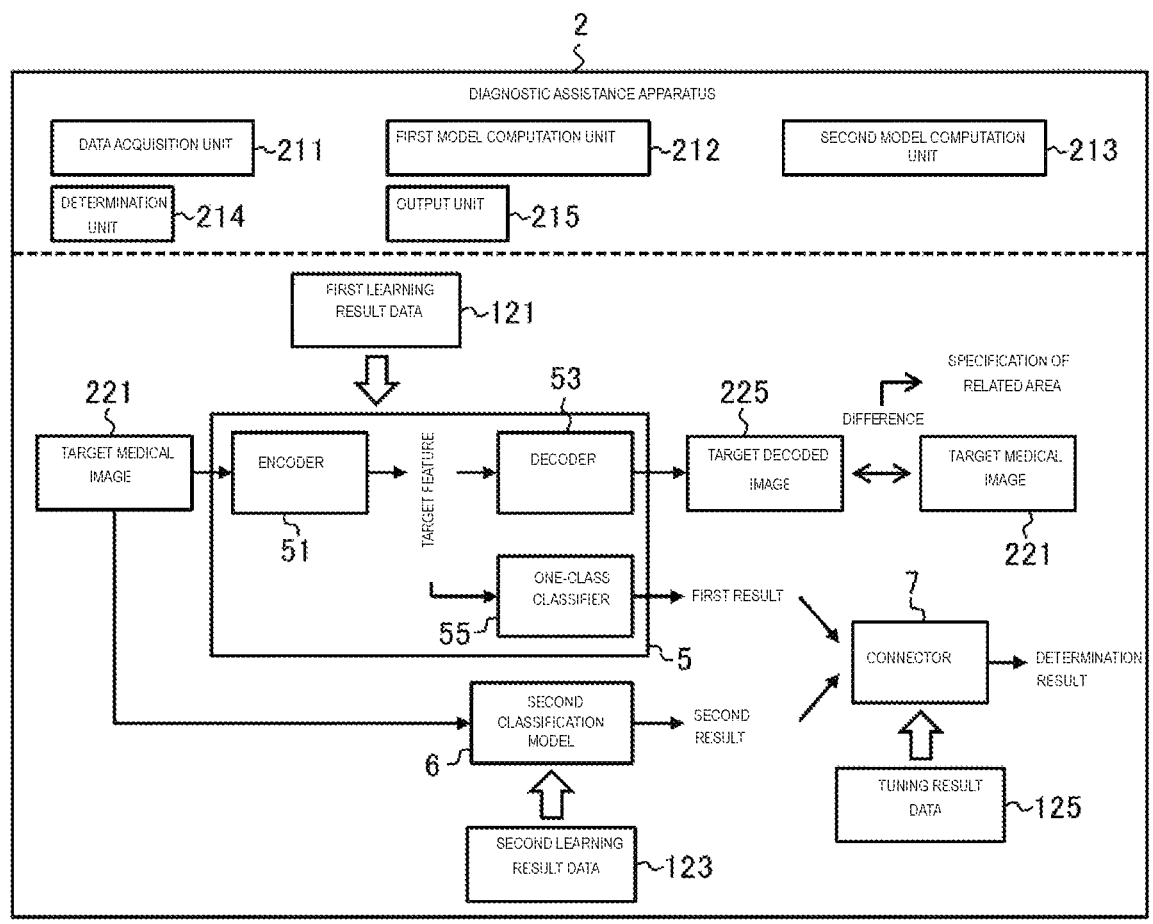
FIG. 6 schematically illustrates an example of a software configuration of the diagnostic assistance apparatus according to the embodiment.

FIG. 6 schematically illustrates an example of a software configuration of the diagnostic assistance apparatus 2 according to the present embodiment. The control unit 21 of the diagnostic assistance apparatus 2 loads into the RAM the diagnostic assistance program 82 stored in the storage unit 22. The control unit 21 controls individual units by using the CPU understanding and executing the instructions contained in the diagnostic assistance program 82 loaded in the RAM. Accordingly, as illustrated in FIG. 6, the diagnostic assistance apparatus 2 according to the present embodiment operates as a computer including software modules of a data acquisition unit 211, a first model computation unit 212, a second model computation unit 213, a determination unit 214, and an output unit 215. This means that in the present embodiment the control unit (CPU) implements the software modules of the diagnostic assistance apparatus 2, similarly to the model generation apparatus 1.

The data acquisition unit 211 acquires the target medical image 221 capturing a body part of a target examinee. The target medical image 221 is a medical image acquired by capturing an image of a body part of a target examinee with the use of an imaging device. the target examinee may include a model representing a human body, similarly to the subject described above.

The first model computation unit 212 obtains the first learning result data 121, thereby having the trained first classification model 5. The first model computation unit 212 feeds the acquired target medical image 221 to the trained first classification model 5 and then performs an arithmetic operation of the trained first classification model 5. In the present embodiment, the arithmetic operation of the first classification model 5 includes converting the acquired target medical image 221 into target features by the encoder 51 fed with the target medical image 221; the arithmetic operation of the first classification model 5 also includes acquiring from the trained one-class classifier 55 an output value corresponding to the first result of the body part of the target examinee captured in the target medical image 221 by feeding the target features acquired by the conversion operation to the trained one-class classifier 55. Specifically, the first model computation unit 212 inputs the acquired target medical image 221 to the trained encoder 51 and performs the arithmetic operation of forward propagation of the trained encoder 51 and the one-class classifier 55. As a result, the first model computation unit 212 acquires an output value corresponding to the first result from the trained first classification model 5.

The second model computation unit 213 obtains the second learning result data 123, thereby having the trained second classification model 6. The second model computation unit 213 feeds the acquired target medical image 221 to the trained second classification model 6 and then performs an arithmetic operation of the trained second classification model 6. In the present embodiment, the second model computation unit 213 inputs the acquired target medical image 221 to the input layer of the trained second classification model 6 and then performs the arithmetic operation of forward propagation of the trained second classification model 6. Consequently, the second model computation unit 213 acquires an output value corresponding to the second result of the body part of the target examinee captured in the target medical image 221 from the output layer of the trained second classification model 6.

In accordance with the first and second results, the determination unit 214 determines whether the body part of the target examinee captured in the target medical image 221 is normal. In the present embodiment, the first result and the second result are configured to indicate the degree of normality of a body part by a numerical value. The determination unit 214 obtains the tuning result data 125, thereby having the connector 7 with the parameters tuned to optimize the determination accuracy of the third learning medical images 351. The determination operation based on the first result and the second result consists of: by feeding the acquired first and second results to the connector 7, individually weighting the first result and the second result with the parameters; connecting the weighted first result and the weighted second result; and determining whether the body part of the target examinee is normal by comparing the determination value acquired by the connection operation to a threshold. Specifically, the determination unit 214 inputs values of the results to the input layer 71 of the connector 7 and performs the arithmetic operation of forward propagation of the connector 7. As a result, the determination unit 214 acquires a determination value or an output value corresponding to a determination result from the output layer 72. When the connector 7 is configured to output a determination value, the determination unit 214 derives a determination result by comparing the acquired determination value to a threshold. The output unit 215 outputs the determination result by the determination unit 214.

In the present embodiment, the arithmetic operation of the first classification model 5 may include, when a body part of a target examinee is determined to be non-normal, feeding the acquired target medical image 221 to the trained encoder 51 and converting the target medical image 221 into target features; feeding the target features acquired by the conversion operation to the trained decoder 53 and generating a target decoded image 225 from the target features; calculating the difference between the target medical image 221 and the target decoded image 225 generated; and, in accordance with the calculated difference, specifying in the target medical image 221 a related area by which the body part of the target examinee is determined to be non-normal. In this case, outputting the determination result may include outputting information indicating the specified related area.

Specifically, the first model computation unit 212 may acquire output values corresponding to target features from the trained encoder 51 by inputting the target medical image 221 to the trained encoder 51 and performing the arithmetic operation of forward propagation of the trained encoder 51. This arithmetic operation may be the same as the operation for acquiring the first result described above. Subsequently, the first model computation unit 212 may acquire an output corresponding to the target decoded image 225 from the trained decoder 53 by inputting the acquired target features to the trained decoder 53 and performing the arithmetic operation of forward propagation of the trained decoder 53. The first model computation unit 212 may then calculate the difference between the target medical image 221 and the target decoded image 225 generated and specify the related area in the target medical image 221 in accordance with the calculated difference. The output unit 215 may output information indicating the specified related area as a determination result.

The trained encoder 51 and decoder 53 can reconstruct with high accuracy the first learning medical image 31, which is used for machine learning, and similar medical images, but the accuracy of reconstruction of other kinds of medical images may be relatively low. Because a medical image capturing a normal body part is used as the first learning medical image 31, the accuracy of reconstruction of medical images capturing abnormal body parts by the trained encoder 51 and decoder 53 can be relatively low. This means that the trained encoder 51 and decoder 53 are likely to fail to reconstruct portions capturing abnormal body parts with high accuracy. Thus, in the arithmetic operation described above, an area with high probability of lesion (possible lesion area) can be extracted as the related area, based on the difference (reconstruction error) between the target medical image 221 and the target decoded image 225. This operation of specifying (extracting) the related area can be performed when a body part of a target examinee is determined to be normal. This means that the operation of specifying the related area may be performed regardless of whether the body part of the target examinee is normal.

OTHERS

The software modules of the model generation apparatus 1 and the software modules of the diagnostic assistance apparatus 2 will be described in detail with an operation example explained later. The present embodiment describes the example in which the software modules of the model generation apparatus 1 and the software modules of the diagnostic assistance apparatus 2 are implemented by general-purpose CPUs. However, part or all of the collection of the software modules may be implemented by one or a plurality of dedicated processors. Additionally, regarding the software configuration of the model generation apparatus 1 and the software configuration of the diagnostic assistance apparatus 2, particular software modules may be excluded, replaced, or added as appropriate to the embodiment.

§ 3 OPERATION EXAMPLE

Figure 7:
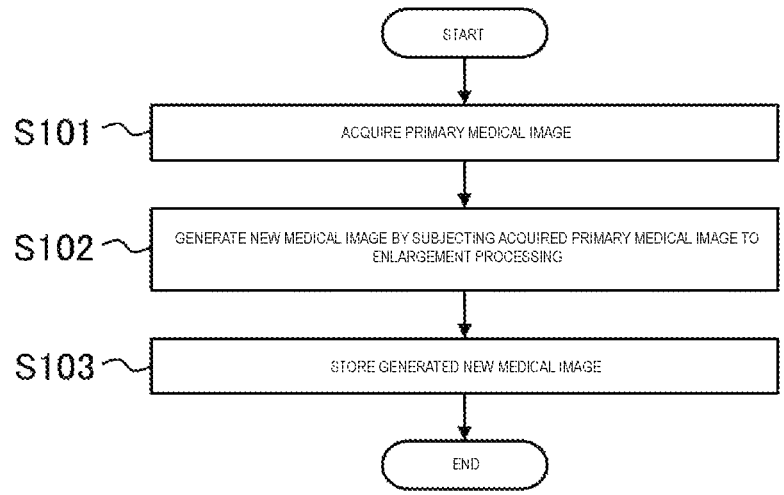
FIG. 7 is a flowchart illustrating an example of a procedure of data enlargement processing by the model generation apparatus according to the embodiment.

[Model Generation Apparatus]
<Enlargement Processing>
FIG. 7 is a flowchart illustrating an example of a procedure of data enlargement processing by the model generation apparatus 1 according to the present embodiment. The following data enlargement procedure is a mere example, and individual steps may be changed when possible. Furthermore, in the following data enlargement procedure, for example, a particular step may be excluded, replaced, or added as appropriate to the embodiment.
(Step S101)
In step S101, the control unit 11 operates as the primary data acquisition unit 118 and acquires one or a plurality of primary medical images 390 capturing body parts of subjects.

The primary medical image 390 may be generated as appropriate. For example, the primary medical image 390 can be generated by capturing an image of a normal or abnormal body part of a subject by an imaging device. The generated primary medical image 390 may be a raw medical image acquired by image capturing or a medical image having been processed by some kind of image processing. Alternatively, the primary medical image 390 may be a new medical image generated by performing enlargement processing in step S102 described later on another primary medical image. A correct label indicating whether a body part captured in the primary medical image 390 is normal may be associated with the generated primary medical image 390. The inference of whether a body part is normal can be made manually by a person such as a medical doctor or mechanically by a machine such as a trained machine learning model.

The primary medical image 390 may be generated automatically by an operation of a computer or manually by being at least partially operated by the operator. The primary medical image 390 may be generated by the model generation apparatus 1 or a computer other than the model generation apparatus 1. When the model generation apparatus 1 generates the primary medical image 390, the control unit 11 performs the series of operations of the generation operation described above automatically or manually with the help of the operator operating with the input device 14, so that one or a plurality of primary medical images 390 can be acquired. When another computer generates the primary medical image 390, the control unit 11 may acquire one or a plurality of primary medical images 390 generated by the computer, for example, through a network or via the storage medium 91. When a plurality of the primary medical images 390 are acquired, a portion of the collection of the primary medical images 390 may be generated by the model generation apparatus 1, whereas the remainder of the collection of the primary medical images 390 may be generated by one or a plurality of computers other than the model generation apparatus 1.

The number of the primary medical images 390 to be acquired may be determined as appropriate to the embodiment. After the primary medical image 390 is acquired, the control unit 11 causes the process to proceed to the following step S102.
(Step S102)
In step S102, the control unit 11 operates as the enlargement processing unit 119 and subjects the acquired primary medical image 390 to enlargement processing and accordingly generate one or a plurality of new medical images 395. The enlargement processing may be constituted by parallel translation, rotation, swiveling, flipping or flopping, cropping, contrast change, enlargement, or reduction, or a combination thereof performed on the primary medical image 390. Rotation is image processing of turning an image around a given point determined as the center. Swiveling is image processing of turning an image around a fixed side to top, bottom, left, or right. The amount of each image processing task may be determined as appropriate in accordance with, for example, a specification by the operator or a configuration value in the program. The number of the new medical images 395 generated based on one primary medical image 390 is not limited to a particular number, and may be determined as appropriate to the embodiment.

When a correct label is associated with the primary medical image 390, a correct label may be associated with the new medical image 395. When it is unnecessary to change the indication of correct label after the enlargement processing, the correct label associated with the primary medical image 390 may be associated with the new medical image 395. Conversely, when it is necessary to change the indication of correct label after the enlargement processing, the correct label associated with the primary medical image 390 may be altered, or a new correct label may be generated; and the altered or generated correct label may be associated with the new medical image 395. The alteration or generation of correct label may be manually or mechanically carried out. When the alteration of correct label is mechanically carried out, the indication of correct label after alteration may be estimated based on the enlargement processing. After generating the new medical image 395, the control unit 11 causes the process to proceed to the following step S103.
(Step S103)
In step S103, the control unit 11 stores in a predetermined storage area the generated one or plurality of new medical images 395. The predetermined storage area may be a memory such as the RAM in the control unit 11, the storage unit 12, an external storage device, or a storage medium, or a combination thereof. The storage medium may be, for example, a CD or DVD, and the control unit 11 may use the drive 16 to store the new medical image 395 in the storage medium. The external storage device may be, for example, a data server such as a network attached storage (NAS). In this case, the control unit 11 may use the communication interface 13 to store the new medical image 395 in the data server through a network. The external storage device may be, for example, a storage device externally connected to the model generation apparatus 1. After the storage operation of the generated new medical image 395 is completed, the control unit 11 ends the procedure of data enlargement according to this operation example.

<Machine Learning of First Classification Model>

Figure 8:
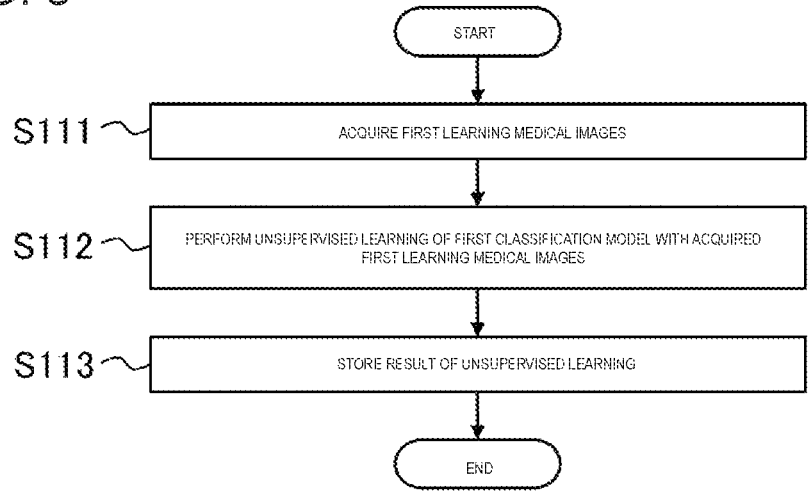
FIG. 8 is a flowchart illustrating an example of a procedure of unsupervised learning of the first classification model by the model generation apparatus according to the embodiment.

FIG. 8 is a flowchart illustrating an example of a procedure of unsupervised learning of the first classification model 5 by the model generation apparatus 1 according to the present embodiment. The following procedure of unsupervised learning of the first classification model 5 is a mere example, and individual steps may be changed when possible. Furthermore, in the following procedure of unsupervised learning of the first classification model 5, for example, a particular step may be excluded, replaced, or added as appropriate to the embodiment.

(Step S111)

In step S111, the control unit 11 operates as the first acquisition unit 110 and acquires the first learning medical images 31 capturing normal body parts of subjects.

At least a portion of the collection of the first learning medical images 31 may be at least either the primary medical image 390 or the new medical image 395. When correct labels are associated with the primary medical image 390 and the new medical image 395, the control unit 11 may extract at least either the primary medical image 390 or the new medical image 395 to be used as the first learning medical image 31 from a database of the primary medical image 390 and the new medical image 395 in accordance with the correct labels. At least a portion of the collection of the first learning medical images 31 may be acquired as a medical image other than the primary medical image 390 and the new medical image 395. In this case, the first learning medical image 31 may be generated in the same manner as the primary medical image 390. It is preferable that all the first learning medical images 31 be medical images capturing normal body parts of subjects. However, a portion of the collection of the first learning medical images 31 may be medical images capturing abnormal body parts of subjects.

The number of the first learning medical images 31 to be acquired may be determined as appropriate to the embodiment. After the first learning medical images 31 are acquired, the control unit 11 causes the process to proceed to the following step S112.

(Step S112)

In step S112, the control unit 11 operates as the first learning unit 111 and performs unsupervised learning of the first classification model 5 with the acquired first learning medical images 31.

In the present embodiment, the first classification model 5 includes the encoder 51, the decoder 53, and the one-class classifier 55. The control unit 11 trains the encoder 51 and the decoder 53 such that, when each first learning medical image 31 is fed to the encoder 51, a decoded image responsively generated by the decoder 53 matches the first learning medical image 31 (in other words, reconstruction errors between the first learning medical images 31 and the corresponding decoded images are minimized). Subsequently, the control unit 11 trains the one-class classifier 55 by using the first learning medical images 31 to evaluate the degree of normality of a body part captured in a fed medical image by one-class classification in accordance with features acquired by the trained encoder 51. Each training process may be carried out by using, for example, batch gradient descent, stochastic gradient descent, or mini-batch gradient descent.

The neural networks implementing the encoder 51, the decoder 53, and the one-class classifier 55 targeted for machine learning may be prepared as appropriate. The architecture (for example, the number of layers, the number of neurons included in each layer, and the connection between neurons in adjacent layers), initial value of weight on each connection between neurons, and initial value of threshold of each neuron of each neural network may be provided by a template or inputted by the operator. When performing relearning, the control unit 11 may use learning result data acquired by the previous machine learning tasks to prepare the encoder 51, the decoder 53, and the one-class classifier 55.

As an example of the training process of the encoder 51 and the decoder 53, firstly, the control unit 11 inputs each first learning medical image 31 to the input layer 511 of the encoder 51 and performs the arithmetic operation of forward propagation of the encoder 51 and the decoder 53. By performing this arithmetic operation, the control unit 11 extracts features from each first learning medical image 31 and acquires from the output layer 533 of the decoder 53 an output value corresponding to a decoded image generated based on the extracted features.

The control unit 11 calculates an error (reconstruction error) between each first learning medical image 31 and the corresponding decoded image acquired from the decoder 53. Loss function may be used to calculate errors. Loss function is a function for evaluating a difference (that is, the degree of difference) between an output of a machine learning model and a correct result; the greater the difference between an output value and a correct result (desired value) is, the greater the error value given by a loss function is. The loss function used to calculate errors is not limited to a particular type, and any type of loss function may be selected as appropriate to the embodiment. A known loss function, such as root-mean-square error or cross entropy error may be used.

With the use of the gradients of the calculated errors, the control unit 11 calculates by back propagation an error of each of the operational parameters (for example, the weight on the connection between neurons and the threshold of each neuron) of the decoder 53 and the encoder 51. The control unit 11 updates the operational parameters of the encoder 51 and the decoder 53 in accordance with the calculated errors. How much the operational parameters are updated may be controlled based on a learning rate. The learning rate may be specified by the operator or given as a configuration value in the program.

By performing the series of operations of the update operation described above, the control unit 11 tunes the operational parameters of the encoder 51 and the decoder 53 to decrease the sum of calculated errors. For example, the control unit 11 may repeat tuning of the operational parameters by performing the series of operations until a predetermined condition is satisfied; the predetermined condition may be, for example, the condition in which the series of operations are performed a predetermined number of times or the condition in which the sum of errors calculated reaches or falls below a threshold. In this manner, the control unit 11 can train the encoder 51 and the decoder 53 such that, when each first learning medical image 31 is fed to the encoder 51, a decoded image responsively generated by the decoder 53 matches the first learning medical image 31.

In the training process of the encoder 51 and the decoder 53, in addition to the update operation described above, the control unit 11 may calculate errors between the features acquired from the encoder 51 and the values acquired from a predetermined probability distribution (for example, Gaussian distribution) and accordingly further tune the operational parameters of the encoder 51 to reduce the sum of errors. In this manner, the control unit 11 may normalize the output value (features) from the encoder 51.

Next, as an example of the training process of the one-class classifier 55, the control unit 11 inputs each first learning medical image 31 to the input layer 511 of the trained encoder 51 and performs the arithmetic operation of forward propagation of the encoder 51 and the one-class classifier 55. By performing this arithmetic operation, the control unit 11 can acquire from the output layer 553 of the one-class classifier 55 an output value corresponding to a result of evaluating by one-class classification the degree of normality of a body part captured in each first learning medical image 31.

The output value acquired from the one-class classifier 55 corresponds to a result of mapping a normal body part in a feature space. The control unit 11 calculates as an error the distance between a point corresponding to the acquired output value and the origin in the feature space. With the use of the gradients of the calculated errors, the control unit 11 calculates errors of the respective operational parameters of the one-class classifier 55 by backpropagation. The control unit 11 updates the operational parameters of the one-class classifier 55 in accordance with the calculated errors. How much the operational parameters of the one-class classifier 55 are updated may be controlled based on the learning rate.

By performing the series of operations of the update operation described above, the control unit 11 tunes the operational parameters of the one-class classifier 55 to decrease the calculated errors. Similarly to the encoder 51 and the decoder 53, the control unit 11 may repeat tuning of the operational parameters of the one-class classifier 55 by performing the series of operations until the predetermined condition is satisfied. In this manner, the control unit 11 can train the one-class classifier 55 in the following manner: based on the features acquired from the trained encoder 51, when a fed medical image belongs to the class of the first learning medical images 31, the body part captured in the medical image is evaluated as normal; when the fed medical image does not belong to the class of the first learning medical images 31, the body part captured in the medical image is evaluated as non-normal.

As the result of the unsupervised learning, the encoder 51 and the one-class classifier 55 of the first classification model 5 learn the distribution of medical images capturing normal body parts from the first learning medical images 31, so that the encoder 51 and the one-class classifier 55 of the first classification model 5 acquire a capability to evaluate by one-class classification the degree of normality of a body part captured in a fed medical image. Additionally, the decoder 53 acquires a capability to properly decode fed medical images belonging to the distribution of the first learning medical images 31 from the features acquired from the encoder 51. After the training process of the first classification model 5 is completed, the control unit 11 causes the process to proceed to the following step S113.
(Step S113)

In step S113, the control unit 11 operates as the storage processing unit 117 and generates information about the result of unsupervised learning in step S112 as the first learning result data 121. In the present embodiment, the control unit 11 generates as the first learning result data 121 information indicating the architecture and operational parameters of the trained encoder 51, the trained decoder 53, and the trained one-class classifier 55 that are created by the unsupervised learning described above. The control unit 11 then stores the generated first learning result data 121 in a predetermined storage area.

The predetermined storage area may be a memory such as the RAM in the control unit 11, the storage unit 12, an external storage device, or a storage medium, or a combination thereof. The storage medium may be, for example, a CD or DVD, and the control unit 11 may use the drive 16 to store the first learning result data 121 in the storage medium. The external storage device may be, for example, a data server such as a network attached storage (NAS). In this case, the control unit 11 may use the communication interface 13 to store the first learning result data 121 in the data server through a network. The external storage device may be, for example, a storage device externally connected to the model generation apparatus 1. After the storage operation of the first learning result data 121 is completed, the control unit 11 ends the procedure of unsupervised learning of the first classification model 5 according to this operation example.

The generated first learning result data 121 may be provided for the diagnostic assistance apparatus 2 at a given timing. For example, the control unit 11 may transfer the first learning result data 121 to the diagnostic assistance apparatus 2 as the operation in step S113 or separately from the operation in step S113. The diagnostic assistance apparatus 2 may receive this transferred data to acquire the first learning result data 121. The diagnostic assistance apparatus 2 may access the model generation apparatus 1 or the data server through a network by using the communication interface 23 to acquire the first learning result data 121. Alternatively, for example, the diagnostic assistance apparatus 2 may acquire the first learning result data 121 via the storage medium 92. Alternatively, for example, the first learning result data 121 may be previously included in the diagnostic assistance apparatus 2.

Furthermore, the control unit 11 may update or newly generate the first learning result data 121 by regularly or irregularly repeating the operations in steps S111 to S113. While the operations are repeated, at least a portion of the collection of the first learning medical images 31 may be, for example, changed, corrected, added, or deleted as appropriate. Subsequently, the control unit 11 may update the first learning result data 121 stored in the diagnostic assistance apparatus 2 by providing the updated or newly generated first learning result data 121 for the diagnostic assistance apparatus 2 in a given manner.

<Machine Learning of Second Classification Model>

Figure 9:
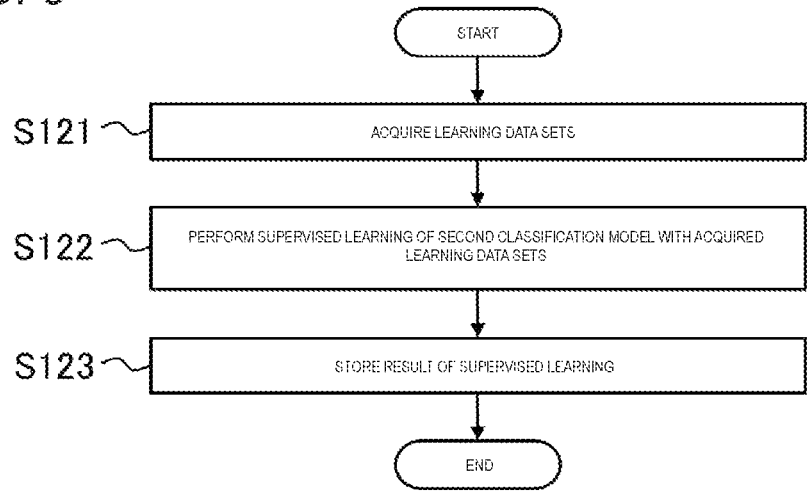
FIG. 9 is a flowchart illustrating an example of a procedure of supervised learning of the second classification model by the model generation apparatus according to the embodiment.

FIG. 9 is a flowchart illustrating an example of a procedure of supervised learning of the second classification model 6 by the model generation apparatus 1 according to the present embodiment. The following procedure of supervised learning of the second classification model 6 is a mere example, and individual steps may be changed when possible. Furthermore, in the following procedure of supervised learning of the second classification model 6, for example, a particular step may be excluded, replaced, or added as appropriate to the embodiment.
(Step S121)

In step S121, the control unit 11 operates as the second acquisition unit 112 and acquires the learning data sets 33.

At least a portion of the collection of the second learning medical images 331 of the learning data sets 33 may be at least either the primary medical image 390 or the new medical image 395. In this case, the control unit 11 may extract at least either the primary medical image 390 or the new medical image 395 to be used as the second learning medical image 331 from the database of the primary medical image 390 and the new medical image 395 to include the normal medical image 3311 and the abnormal medical image 3312 as appropriate. At least a portion of the collection of the second learning medical images 331 of the learning data sets 33 may be acquired as a medical image other than the primary medical image 390 and the new medical image 395. In this case, the learning data set 33 may be generated in the same manner as the primary medical image 390. Additionally, a portion of the collection of the second learning medical images 331 of the learning data sets 33 may be the same as the first learning medical images 31.

The number of the learning data sets 33 to be acquired may be determined as appropriate to the embodiment. After the learning data sets 33 are acquired, the control unit 11 causes the process to proceed to the following step S122.

(Step S122)

In step S122, the control unit 11 operates as the second learning unit 113 and performs supervised learning of the second classification model 6 with the acquired learning data sets 33. The control unit 11 trains the second classification model 6 such that, with respect to each learning data set 33, in response to an input of the second learning medical image 331, when evaluating the degree of normality of a body part captured in the inputted second learning medical image 331, the evaluation result matches the correct label 333 corresponding to the second learning medical image 331. Specifically, the control unit 11 uses the second learning medical image 331 as training data, and the correct label 333 as teaching signal to perform supervised learning of the second classification model 6. Similarly to step S121 described above, this training process may be carried out by using, for example, batch gradient descent, stochastic gradient descent, or mini-batch gradient descent.

Similarly to the first classification model 5 described above, the convolutional neural networks implementing the second classification model 6 targeted for machine learning may be prepared as appropriate. The architecture, initial value of weight on each connection between neurons, and initial value of threshold of each neuron of the second classification model 6 may be provided by a template or inputted by the operator. When performing relearning, the control unit 11 may use learning result data acquired by the previous machine learning tasks to prepare the second classification model 6.

An example of the training process of the second classification model 6, firstly, the control unit 11 inputs the second learning medical image 331 of each learning data set 33 to the input layer of the second classification model 6 and performs the arithmetic operation of forward propagation of the second classification model 6. By performing this arithmetic operation, the control unit 11 acquires from the output layer an output value corresponding to a result of evaluating the degree of normality of a body part captured in each second learning medical image 331. The control unit 11 calculates an error between the output value acquired from the output layer by the arithmetic operation and the correct label 333, with respect to each learning data set 33. Similarly to step S121 described above, loss function may be used as appropriate to calculate errors.

With the use of the gradients of the calculated errors, the control unit 11 calculates errors of the respective operational parameters of the second classification model 6 by back-propagation. The control unit 11 updates the operational parameters of the second classification model 6 in accordance with the calculated errors. How much the operational parameters of the second classification model 6 are updated may be controlled based on the learning rate.

By performing the series of operations of the update operation described above, the control unit 11 tunes the operational parameters of the second classification model 6 to decrease the sum of calculated errors. Similarly to step S121, the control unit 11 may repeat tuning of the operational parameters of the second classification model 6 by performing the series of operations until the predetermined condition is satisfied. In this manner, the control unit 11 can train the second classification model 6 such that, with respect to each learning data set 33, in response to an input of the second learning medical image 331, when evaluating the degree of normality of a body part captured in the inputted second learning medical image 331, the evaluation result matches the correct label 333 corresponding to the second learning medical image 331.

As the result of the supervised learning, the second classification model 6 acquires a capability of properly evaluating the degree of normality of a body part captured in a fed medical image when this case is related to a case included in the learning data sets 33. After the training process of the second classification model 6 is completed, the control unit 11 causes the process to proceed to the following step S123.

(Step S123)

In step S123, the control unit 11 operates as the storage processing unit 117 and generates information about the result of supervised learning in step S122 as the second learning result data 123. In the present embodiment, the control unit 11 generates as the second learning result data 123 information indicating the architecture and operational parameters of the trained second classification model 6 created by the supervised learning described above. The control unit 11 then stores the generated second learning result data 123 in a predetermined storage area. The predetermined storage area may be a memory such as the RAM in the control unit 11, the storage unit 12, an external storage device, or a storage medium, or a combination thereof. The memory for the second learning result data 123 may be identical to or different from the memory for the first learning result data 121.

After the storage operation of the second learning result data 123 is completed, the control unit 11 ends the procedure of supervised learning of the second classification model 6 according to this operation example. Similarly to the first learning result data 121, the second learning result data 123 may be provided for the diagnostic assistance apparatus 2 at a given timing. The operations in steps S121 to S123 may be regularly or irregularly repeated. While the operations are repeated, at least a portion of the collection of the learning data sets 33 may be, for example, changed, corrected, added, or deleted as appropriate. Subsequently, by providing the updated or newly generated second learning result data 123 for the diagnostic assistance apparatus 2 in a given manner, the second learning result data 123 stored in the diagnostic assistance apparatus 2 may be updated.

<Connector Parameter Tuning>

Figure 10:
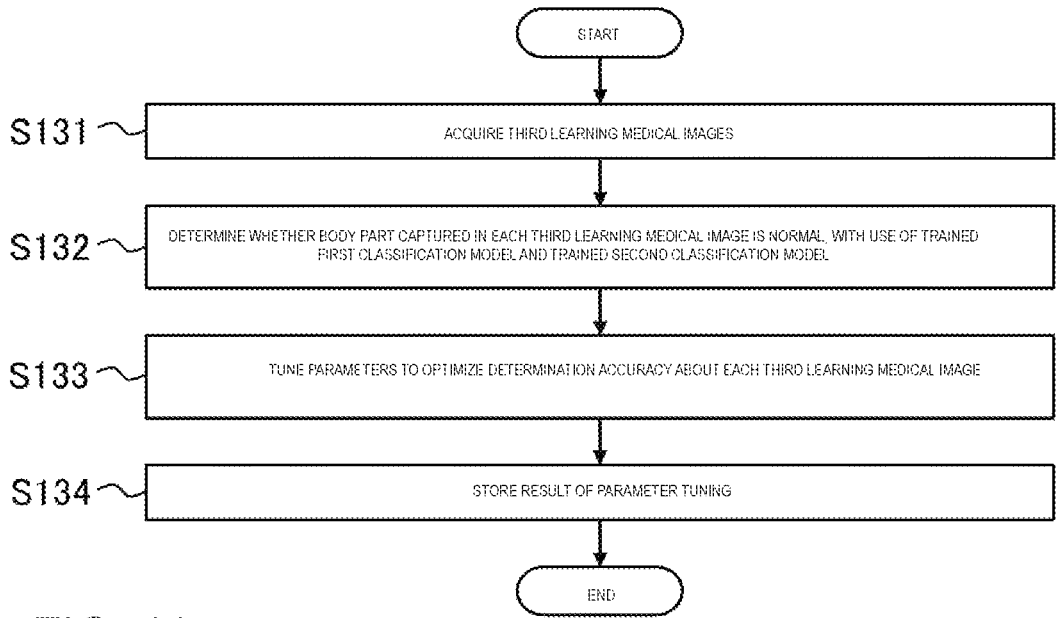
FIG. 10 is a flowchart illustrating an example of a procedure of parameter tuning (optimization) by the model generation apparatus according to the embodiment.

FIG. 10 is a flowchart illustrating an example of a procedure of parameter tuning by the model generation apparatus 1 according to the present embodiment. The information processing method of the model generation apparatus 1 including the procedure of data enlargement processing, the procedure of unsupervised learning of the first classification model 5, the procedure of supervised learning of the second classification model 6, and the following procedure of parameter tuning is an example of a "model generation method". The following procedure regarding parameter tuning is a mere example, and individual steps may be changed when possible. Furthermore, in the following procedure regarding parameter tuning, for example, a particular step may be excluded, replaced, or added as appropriate to the embodiment.

(Step S131)

In step S131, the control unit 11 operates as the third acquisition unit 114 and acquires the tuning data sets 35.

At least a portion of the collection of the third learning medical images 351 of the tuning data sets 35 may be at least either the primary medical image 390 or the new medical image 395. At least a portion of the collection of the third learning medical images 351 of the tuning data sets 35 may be acquired as a medical image other than the primary medical image 390 and the new medical image 395. In this case, the tuning data set 35 may be generated in the same manner as the primary medical image 390. Additionally, a portion of the collection of the third learning medical images 351 of the tuning data sets 35 may be the same as the first learning medical images 31 or the second learning medical images 331. The third learning medical images 351 of the tuning data sets 35 may include one or a plurality of limit samples 352. The limit samples 352 may be selected as appropriate. The limit samples 352 may be selected, for example, manually by the operator.

The number of the tuning data sets 35 to be acquired may be determined as appropriate to the embodiment. After the tuning data sets 35 are acquired, the control unit 11 causes the process to proceed to the following step S132.

(Steps S132 and S133)

In step S132, the control unit 11 operates as the determination unit 115 and determines whether a body part captured in the third learning medical image 351 of each tuning data set 35 is normal, by using the trained first classification model 5 and the trained second classification model 6. In step S133, the control unit 11 operates as the tuning unit 116 and tunes the parameters of the connector 7 to optimize the accuracy of determination by the determination unit 115 about each third learning medical image 351.

In the present embodiment, the control unit 11 performs in step S132 and step S133 supervised learning of the connector 7 using the tuning data sets 35. Similarly to step S121 described above, the training process of the connector 7 may be carried out by using, for example, batch gradient descent, stochastic gradient descent, or mini-batch gradient descent. Similarly to the above cases such as the first classification model 5, the neural network implementing the connector 7 targeted for machine learning may be prepared as appropriate. The architecture, initial value of weight on each connection between neurons, and initial value of threshold of each neuron of the connector 7 may be provided by a template or inputted by the operator. When performing relearning, the control unit 11 may use learning result data acquired by the previous machine learning tasks to prepare the connector 7.

Specifically, in step S132, the control unit 11 inputs the third learning medical image 351 of each tuning data set 35 to the encoder 51 of the trained first classification model 5 and performs the arithmetic operation of forward propagation of the encoder 51 and the one-class classifier 55 of the trained first classification model 5. By performing this arithmetic operation, the control unit 11 acquires the first result of each third learning medical image 351 from the trained one-class classifier 55. The control unit 11 also inputs the third learning medical image 351 of each tuning data set 35 to the trained second classification model 6 and performs the arithmetic operation of forward propagation of the second classification model 6. By performing this arithmetic operation, the control unit 11 acquires the second result of each third learning medical image 351 from the trained second classification model 6. The control unit 11 subsequently inputs the acquired first and second results to the input layer 71 of the connector 7 and performs the arithmetic operation of forward propagation of the connector 7. By performing this arithmetic operation, the control unit 11 acquires from the output layer 72 a determination value for deriving a determination result by comparing the determination value to a threshold or an output value directly representing the determination result, with respect to each third learning medical image 351. The threshold may be given as appropriate.

Subsequently, in step S133, the control unit 11 calculates an error between a determination result derived from a determination value or represented by an output value and a correct result indicated by the correct label 353 with respect to each tuning data set 35. Similarly to the steps including step S121 described above, loss function may be used as appropriate to calculate errors. With the use of the gradients of the calculated errors, the control unit 11 calculates errors of the respective operational parameters of the connector 7 by backpropagation. The control unit 11 updates the operational parameters of the connector 7 in accordance with the calculated errors. How much the parameters of the connector 7 are updated may be controlled based on a learning rate.

By performing the series of operations of the update operation described above, the control unit 11 tunes the parameters of the connector 7 to decrease the sum of calculated errors. Similarly to the steps including step S121, the control unit 11 may repeat tuning of the parameters of the connector 7 by performing the series of operations in steps S132 and S133 until the predetermined condition is satisfied. Additionally, when the third learning medical images 351 include one or a plurality of limit samples 352, the control unit 11 may repeat tuning of the operational parameters of the connector 7 until errors of determination results of the limit samples 352 are eliminated. As a result, the control unit 11 can tune the parameters of the connector 7 to optimize the accuracy of determination about the third learning medical images 351. After the tuning of the parameters of the connector 7 is completed, the control unit 11 causes the process to proceed to the following step S134.

(Step S134)

In step S134, the control unit 11 operates as the storage processing unit 117 and generates information about the result of tuning parameters in step S133 as the tuning result data 125. In the present embodiment, the control unit 11 generates as the tuning result data 125 information indicating the architecture and parameters of the trained connector 7 created by the supervised learning described above. The control unit 11 then stores the generated tuning result data 125 in a predetermined storage area. The predetermined storage area may be a memory such as the RAM in the control unit 11, the storage unit 12, an external storage device, or a storage medium, or a combination thereof. The memory for the tuning result data 125 may be identical to at least one of the first learning result data 121 and the second learning result data 123, or different from both the first learning result data 121 and the second learning result data 123.

After the storage operation of the tuning result data 125 is completed, the control unit 11 ends the procedure regarding parameter tuning of the connector 7 according to this operation example. Similarly to the cases including the first learning result data 121, the tuning result data 125 may be provided for the diagnostic assistance apparatus 2 at a given timing. The operations in steps S131 to S134 may be regularly or irregularly repeated. While the operations are repeated, at least a portion of the collection of the tuning data sets 35 may be, for example, changed, corrected, added, or deleted as appropriate. Additionally, at least a portion of the collection of the one or plurality of limit samples 352 may be, for example, changed, corrected, added, or deleted as appropriate. Subsequently, by providing the updated or newly generated tuning result data 125 for the diagnostic assistance apparatus 2 in a given manner, the tuning result data 125 stored in the diagnostic assistance apparatus 2 may be updated.

[Diagnostic Assistance Apparatus]

FIG. 11 is a flowchart illustrating an example of a procedure of the diagnostic assistance apparatus 2 according to the present embodiment. The following procedure of the diagnostic assistance apparatus 2 is an example of a "diagnostic assistance method". The following procedure of the diagnostic assistance apparatus 2 is a mere example, and individual steps may be changed when possible. Furthermore, in the following procedure of the diagnostic assistance apparatus 2, for example, a particular step may be excluded, replaced, or added as appropriate to the embodiment.

(Step S201)

In step S201, the control unit 21 operates as the data acquisition unit 211 and acquires the target medical image 221 capturing a body part of a target examinee. The method for acquiring the target medical image 221 may be selected as appropriate to the embodiment. For example, the control unit 21 may acquire the target medical image 221 directly from an imaging device. Alternatively, for example, the control unit 21 may acquire the target medical image 221 from another computer. The number of the target medical images 221 to be acquired may be determined as appropriate to the embodiment. After the target medical image 221 is acquired, the control unit 21 causes the process to proceed to the following step S202. When a plurality of the target medical images 221 are acquired, the control unit 21 performs the operation in step S202 and the subsequent steps on each target medical image 221.

(Step S202)

In step S202, the control unit 21 operates as the first model computation unit 212 and acquires the first result of the body part of the target person captured in the acquired target medical image 221 by using the trained first classification model 5. Specifically, the control unit 21 feeds the acquired target medical image 221 to the trained first classification model 5 and performs the arithmetic operation of the trained first classification model 5, so that the control unit 21 acquires an output value corresponding to the first result from the trained first classification model 5.

In the present embodiment, the control unit 21 refers to the first learning result data 121 and accordingly configures the trained encoder 51 and the trained one-class classifier 55. The control unit 21 inputs the target medical image 221 to the input layer 511 of the trained encoder 51 and performs the arithmetic operation of forward propagation of the trained encoder 51. By performing this arithmetic operation, the control unit 21 acquires output values corresponding to target features from the output layer 513. Subsequently, the control unit 21 inputs the acquired target features to the input layer 551 of the trained one-class classifier 55 and performs the arithmetic operation of forward propagation of the trained one-class classifier 55. By performing this arithmetic operation, the control unit 21 acquires an output value corresponding to the first result from the output layer 553. After the first result is acquired, the control unit 21 causes the process to proceed to the following step S203.

(Step S203)

In step S203, the control unit 21 operates as the second model computation unit 213 and acquires the second result of the body part of the target person captured in the acquired target medical image 221 by using the trained second classification model 6. Specifically, the control unit 21 feeds the acquired target medical image 221 to the trained second classification model 6 and performs the arithmetic operation of the trained second classification model 6, so that the control unit 21 acquires an output value corresponding to the second result from the trained second classification model 6.

In the present embodiment, the control unit 21 refers to the second learning result data 123 and accordingly configures the trained second classification model 6. The control unit 21 inputs the target medical image 221 to the input layer of the trained second classification model 6 and performs the arithmetic operation of forward propagation of the trained second classification model 6. By performing this arithmetic operation, the control unit 21 acquires an output value corresponding to the second result from the output layer. After the second result is acquired, the control unit 21 causes the process to proceed to the following step S204.

It should be noted that the timing of performing the operation in step S203 is not limited to this example, and the timing may be changed as appropriate to the embodiment. The operation in step S203 may be performed, for example, before step S202 or in parallel with step S202.

(Step S204)

In step S204, the control unit 21 operates as the determination unit 214 and, in accordance with the first and second results, finally determines whether the body part of the target examinee captured in the target medical image 221 is normal.

In the present embodiment, the control unit 21 refers to the tuning result data 125 and accordingly configures the trained connector 7. The control unit 21 inputs the acquired first and second results to the input layer 71 of the trained connector 7 and performs the arithmetic operation of forward propagation of the trained connector 7. By performing this arithmetic operation, the control unit 21 acquires a determination value or an output value corresponding to a determination result from the output layer 72. When the output layer 72 is configured to output a determination value, the control unit 21 derives a determination result by comparing the acquired determination value to a threshold. The threshold may be given as appropriate. After the determination result is acquired, the control unit 21 causes the process to proceed to the following step S205.

(Step S205)

In step S205, the control unit 21 determines which step the process proceeds to in accordance with the determination result in step S204. When in step S204 the body part of the target examinee is determined to be non-normal, the control unit 21 causes the process to proceed to step S206. Conversely, when the body part of the target examinee is determined to be normal, the control unit 21 omits the operations in steps S206 to S208 and causes the process to proceed to step S209.

(Step S206)

In step S206, the control unit 21 operates as the first model computation unit 212 and generates the target decoded image 225 from the target features by using the trained decoder 53.

In the present embodiment, the control unit 21 refers to the first learning result data 121 and accordingly configures the trained encoder 51 and the trained decoder 53. The control unit 21 inputs the target medical image 221 to the input layer 511 of the trained encoder 51 and performs the arithmetic operation of forward propagation of the trained encoder 51. By performing this arithmetic operation, the control unit 21 acquires output values corresponding to target features from the output layer 513. Subsequently, the control unit 21 inputs the acquired target features to the input layer 531 of the trained decoder 53 and performs the arithmetic operation of forward propagation of the trained decoder 53. By performing this arithmetic operation, the control unit 21 acquires output values corresponding to the target decoded image 225 from the output layer 533. When the operation result in step S202 is used, the control unit 21 may omit the operation regarding the encoder 51 in step S206. After the target decoded image 225 is acquired, the control unit 21 causes the process to proceed to the following step S207.

(Steps S207 and S208)

In step S207, the control unit 21 operates as the first model computation unit 212 and calculates the difference between the target medical image 221 and the target decoded image 225 generated. In the subsequent step S208, the control unit 21 operates as the first model computation unit 212 and, in accordance with the calculated difference, specifies in the target medical image 221 a related area by which the body part of the target examinee is determined to be non-normal.

As described above, a portion with high probability of abnormality is not accurately reconstructed in the target decoded image 225, and thus, the portion is greatly different from a corresponding portion in the target medical image 221. For this reason, the control unit 21 calculates differences of the corresponding picture elements between the target medical image 221 and the target decoded image 225 and compares a difference value of each picture element to a threshold. The threshold may be given as appropriate. By performing this operation, the control unit 21 can extract as the related area a portion of a picture element having a difference value equal to or greater than the threshold (or exceeding the threshold). After the related area is specified, the control unit 21 causes the process to proceed to the following step S209.

It should be noted that the operations in steps S206 to S209 may also be performed when the body part of the target examinee is determined to be normal. In this case, the operation in step S205 may be omitted. At least a portion (especially step S206) of the collection of the operations in steps S206 to S208 may be performed in step S202. In this case, the result of specifying the related area may be disregarded or treated in the same manner as when the body part of the target examinee is determined to be non-normal.

(Step S209)

In step S209, the control unit 21 operates as the output unit 215 and outputs information about the result of determining whether the body part of the target examinee is normal.

The output destination and details of the output information may be determined as appropriate to the embodiment. The output destination may be, for example, the output device 25, an output device of another computer, the RAM, the storage unit 22, a data server, an external storage device, or a storage device of another computer. Concerning the details of the output information, the control unit 21 may output, for example, result information directly indicating the determination result. Alternatively, for example, the control unit 21 may perform a predetermined information processing operation in accordance with the determination result; and the control unit 21 may output information indicating a result of performing the predetermined information processing operation as result information. For example, the control unit 21 may output a particular message (for example, an alert for indicating a high probability that the body part is non-normal) in accordance with the determination result. The result information may be outputted solely or together with the target medical image 221. In step S201, when a plurality of the target medical images 221 are acquired, the control unit 21 may display the target medical images 221 to appear at a glance on a display device. In this case, the control unit 21 may display the target medical image 221 determined to be non-normal in a prioritized or separate manner.

Outputting the determination result may include associating result information indicating the determination result with the target medical image 221. The data format of the result information may be selected as appropriate to the embodiment. For example, the result information may be implemented by a Digital Imaging and Communications in Medicine (DICOM) tag. Additionally, outputting the determination result may include outputting information indicating the related area specified in step S208. In this case, the related area may be outputted solely or together with the target medical image 221.

Figure 12A:
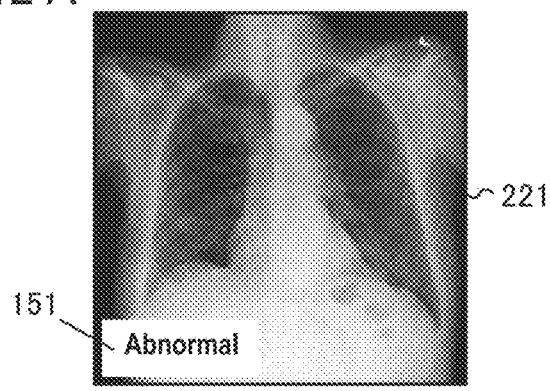
FIG. 12A schematically illustrates an example of display presentation of result information according to the embodiment.
Figure 12B:
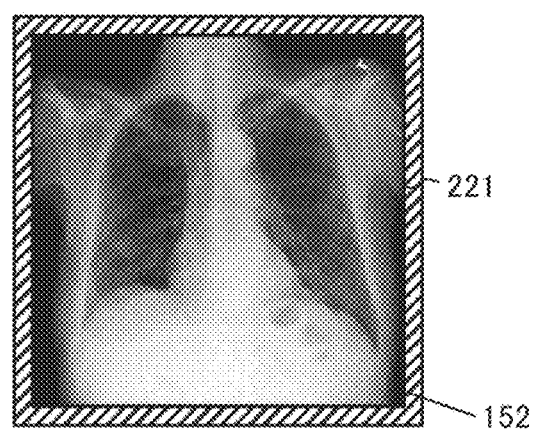
FIG. 12B schematically illustrates an example of display presentation of result information according to the embodiment.

FIGS. 12A and 12B schematically illustrate format examples for outputting information indicating a determination result together with the target medical image 221. In the example in FIG. 12A, the control unit 21 combines a text indication 251 indicating a determination result with the target medical image 221 and outputs the combined image to, for example, the output device 25. The contents and position of the text indication 251 may be determined as appropriate to the embodiment. When the related area is specified, the text indication 251 may be arranged in an area other than the related area. As indicated by this example, outputting the determination result may include combining information indicating the determination result with the target medical image 221. In this case, information indicating the determination result is not necessarily limited to the example of the text indication 251. In addition to text, for example, a symbol, mark, or diagram may be used as information indicating the determination result.

In the example in FIG. 12B, when outputting the target medical image 221 to, for example, the output device 25, the control unit 21 changes the color tone (hue, brightness, saturation) of an outer frame 252 of the target medical image 221 in accordance with the determination result. This means that the control unit 21 may output the target medical image 221 determined to be normal and the target medical image 221 determined to be non-normal in the manner in which both images are different from each other with respect to the color tone of the outer frame 252. The color tone of the outer frame 252 is an example of visual effect. As represented by this example, the control unit 21 may indicate the determination result by using a visual effect with the target medical image 221. The visual effect is not necessarily limited to the example of the color tone of the outer frame 252. In addition to the color tone of the outer frame 252, for example, a texture or pattern may be used as the visual effect.

Figure 13A:
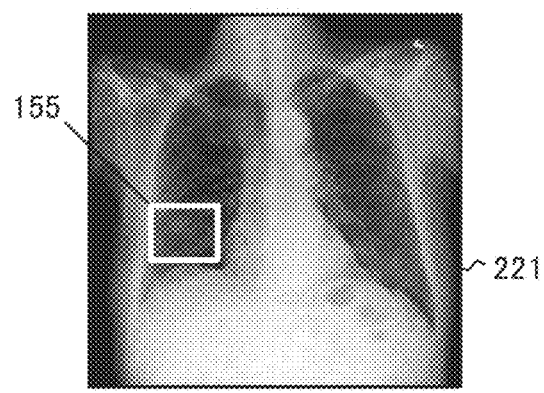
FIG. 13A schematically illustrates an example of display presentation of a related area according to the embodiment.
Figure 13B:
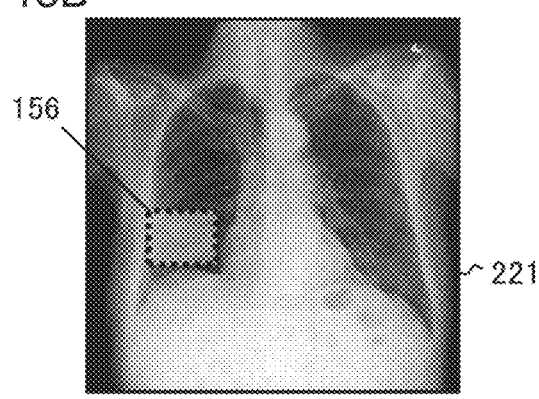
FIG. 13B schematically illustrates an example of display presentation of a related area according to the embodiment.
Figure 13C:
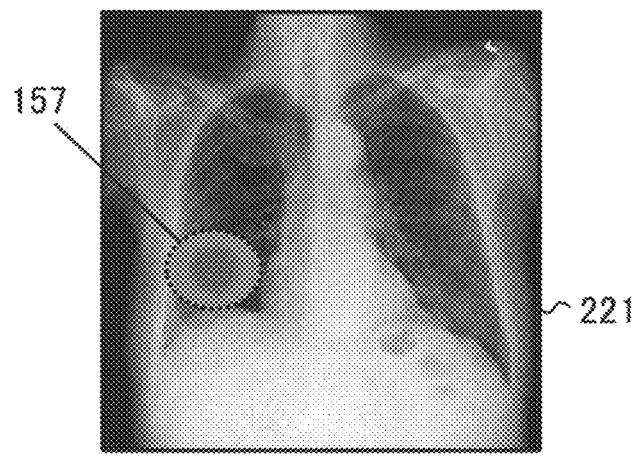
FIG. 13C schematically illustrates an example of display presentation of a related area according to the embodiment.

FIGS. 13A to 13C schematically illustrate format examples for outputting information indicating a related area together with the target medical image 221. In the example in FIG. 13A, the control unit 21 displays a box 255 to indicate a related area on the target medical image 221. The box 255 is an example of information indicating a related area. The shape of the box 255 may be the same as the shape of the specified related area. Alternatively, a predetermined shape that can include a related area may be used as the shape of the box 255. The predetermined shape may be, for example, a rectangle, circle, or oval. The visual effect of the box 255 may be determined as appropriate to the embodiment.

In the example in FIG. 13B, the control unit 21 displays an emphasized area 256 to indicate a related area on the target medical image 221. The emphasized area 256 is an example of information indicating a related area. The emphasized area 256 is formed with a visual effect different from the other area (the area except the emphasized area 256). The visual effect may be specified by, for example, a color tone. Similarly to the box 255, the shape of the emphasized area 256 may be the same as the shape of the specified related area; alternatively, the predetermined shape may be used as the shape of the emphasized area 256.

In the example in FIG. 13C, the control unit 21 displays a heat map 257 to indicate a related area on the target medical image 221. The heat map 257 is an example of information indicating a related area. In the heat map 257, the greater difference between the target medical image 221 and the target decoded image 225 exists at a picture element, the greater value (for example, darker color) indicates the picture element. The heat map 257 may be generated as appropriate in accordance with the difference value of each picture element.

For ease of description, FIGS. 12A, 12B, and 13A to 13C use a chest X-ray image as an example of the target medical image 221. This X-ray image is published in Xiaosong Wang, Yifan Peng, Le Lu, Zhiyong Lu, Mohammadhadi Bagheri, Ronald Summers, ChestX-ray8: Hospital-scale Chest X-ray Database and Benchmarks on Weakly-Supervised Classification and Localization of Common Thorax Diseases, IEEE CVPR, pp. 3462-3471, 2017 (Reference URL: https://nihcc.app.box.com/v/ChestXray-NIHCC). The target medical image 221, however, is not limited to the example of the drawings. After outputting information about a determination result is completed, the control unit 21 ends the procedure of the diagnostic assistance apparatus 2 according to this operation example.

[Characteristics]

As described above, in the present embodiment, by performing the operations in steps S111 and S112 described above, the model generation apparatus 1 generates the first classification model 5 trained by unsupervised learning using the first learning medical images 31 of normal cases. Along with this, by performing the operations in steps S121 and S122 described above, the model generation apparatus 1 generates the second classification model 6 trained by supervised learning using the learning data sets 33 including normal cases and abnormal cases. Collecting a large number of the learning data sets 33 including the second learning medical images 331 of abnormal cases is difficult and costly, whereas collecting the first learning medical images 31 of normal cases is relatively inexpensive and not very difficult. For this reason, a relatively small number of the learning data sets 33 are used in step S122, and as a result, the classification accuracy of the trained second classification model 6 may be relatively low. By contrast, a large number of the first learning medical images 31, which are easily collected with relatively low costs, are used in step S112, and as a result, the classification accuracy of the trained first classification model 5 can be made high. The trained first classification model 5 can supplement the classification accuracy of the trained second classification model 6. As such, the present embodiment can improve with relatively low costs the accuracy of classifying whether a body part of a target examinee captured in a medical image is normal. By using in steps S201 to S204 described above the two generated classification models, namely the trained first classification model 5 and the trained second classification model 6, it is expected that the diagnostic assistance apparatus 2 can highly accurately determine whether a body part of a target examinee captured in the target medical image 221 is normal.

Furthermore, in the present embodiment, the diagnostic assistance apparatus 2 includes the connector 7 configured to connect the first result acquired by the trained first classification model 5 and the second result acquired by the trained second classification model 6. By performing the operations in steps S131 to S133, the parameters of the connector 7 are tuned to optimize the accuracy of determination on the third learning medical images 351. This can further improve the accuracy of classifying whether a body part of a target examinee captured in the target medical image 221 is normal. In the present embodiment, the third learning medical images 351 may include the limit samples 352. With this configuration, improvements in the accuracy of classification on the limit samples 352 and similar examination targets can be expected. By determining serious cases as the limit samples 352, it is possible to reduce the probability of misclassification of the serious cases and similar cases.

Further, in the present embodiment, result information indicating a determination result can be added as an annotation to the target medical image 221 in step S209. This configuration can increase the convenience of using the target medical image 221. Visually displaying the determination result together with the target medical image 221, as in, for example, FIGS. 12A and 12B, can reduce the likelihood that medical doctors fail to discover abnormalities in image interpretation and also enhance the efficiency of image interpretation. Additionally, for example, in accordance with the associated result information, it is possible to extract only the target medical image 221 capturing a body part determined to be non-normal. With this configuration, the target medical image 221 capturing a non-normal body part can be displayed with priority on a display device (for example, the output device 25), and as a result, loads on medical doctors for image interpretation can be lightened.

Moreover, in the present embodiment, an abnormal area or an area with high probability of abnormality can be extracted as a related area by using the trained encoder 51 and the trained decoder 53 generated by the model generation apparatus 1. The diagnostic assistance apparatus 2 can add information indicating the related area as an annotation to the target medical image 221 in step S209. This configuration can increase the convenience of using the target medical image 221. Clarifying the related area on the target medical image 221, as in, for example, FIGS. 13A to 13C, can enhance the efficiency of image interpretation by medical doctors.

To cause a machine learning model to acquire by supervised learning a capability to specify a portion to be annotated, learning data sets need to include labels indicating portions to be annotated in learning medical images. General image interpretation as in health checkups usually includes only visual check of medical images and less likely includes inputting a portion to be annotated. Hence, in this case, costs for collecting learning data sets is further increased by an amount equivalent to the additional task of inputting a label indicating a portion to be annotated. This task additionally requires specialist knowledge, and thus, collecting a large number of learning data sets is significantly difficult. To avoid this problem, instead of using labels indicating portions to be annotated, the present embodiment uses a large number of the first learning medical images 31, so that the first classification model 5 can acquire a capability to specify a related area with relatively high accuracy. As such, the present embodiment can cause the machine learning model to acquire a capability to specify a related area in a medical image with relatively low costs.

Furthermore, in the present embodiment, by performing the operations in steps S101 and S102, one or a plurality of new medical images 395 can be generated from the primary medical image 390. The generated new medical image 395 can be used as each learning medical image (31, 331, 351). As a result, the present embodiment can easily increase the number of the learning medical images (31, 331, 351) with little cost, thereby improving the classification accuracy of the trained first classification model 5 and the trained second classification model 6 generated.

Further, in the present embodiment, the first classification model 5 includes the one-class classifier 55. The one-class classifier 55 is implemented by a neural network. The second classification model 6 is implemented by a convolutional neural network. With these configurations, it is possible to provide the first classification model 5 and the second classification model 6 that can properly classify whether a body part of a target examinee is normal.

§ 4 MODIFICATIONS

The above has described the embodiment of the present disclosure in detail, but the foregoing description is a mere example of the present disclosure in all respects. As might be expected, various changes and modifications can be made without departing from the range of the present disclosure. For example, the following changes can be made. It should be noted that in the following description the same reference characters are assigned to the same constituent elements as the embodiment, and descriptions of the same points as the embodiment are not repeated. The following modifications can be combined as appropriate.

4.1

In the embodiment, fully connected neural networks are used as the encoder 51, the decoder 53, the one-class classifier 55, and the connector 7. A convolutional neural network is used as the second classification model 6. However, the type of neural network used as each element is not limited to these examples, and the type of neural network can be selected as appropriate to the embodiment. For example, a convolutional neural network may be used as the encoder 51. As another example, a fully connected neural network may be used as the second classification model 6.

As the first classification model 5 and the second classification model 6, machine learning models other than neural networks may be used. For example, the encoder 51 and the decoder 53 may be implemented by orthogonal projection matrixes using characteristic vectors derived from principal component analysis. In this case, unsupervised learning may include principal component analysis. Further, the one-class classifier 55 may be implemented by, for example, a one-class support vector machine. For example, when a medical image radically different from the first learning medical images 31, such as a medical image capturing an abnormal body part, is fed to the trained encoder 51, the values of features acquired from this medical image are basically separated from the values of features acquired from the first learning medical images 31. Hence, the one-class classifier 55 may be constituted by information indicating the distribution and classification boundary (for example, threshold) of features of the first learning medical images 31 acquired by the trained encoder 51. In this case, the one-class classifier 55 may determine whether the features of the fed medical image are outliers in accordance with the distances between the features of the fed medical image and the features of the first learning medical images 31, thereby evaluating the degree of normality of the body part captured in the fed medical image. In a similar manner, the first classification model 5 may be constituted by information indicating a data group including the first learning medical images 31 and the classification boundary. In this case, the first classification model 5 may determine whether the fed medical image is an outlier in accordance with the distances between the fed medical image and the first learning medical images 31, thereby evaluating the degree of normality of the body part captured in the fed medical image. Furthermore, the second classification model 6 may be implemented by, for example, a regression model or support vector machine. The method of each machine learning task may be selected as appropriate in accordance with the configuration of each model.

4.2

In the embodiment, the input and output contents of the first classification model 5 and the second classification model 6 are not necessarily limited to the example described above, and the input and output contents may be changed as appropriate to the embodiment. For example, the classification by the second classification model 6 may include estimation of related area in the target medical image 221. This means that the output value of the second classification model 6 may include information indicating a related area. In this case, the correct label 333 may include information indicating a related area in the second learning medical image 331. Further, for example, at least one of the first classification model 5 and the second classification model 6 may be configured to further accept an input of attribute information indicating attributes of a person.

Figure 14A:
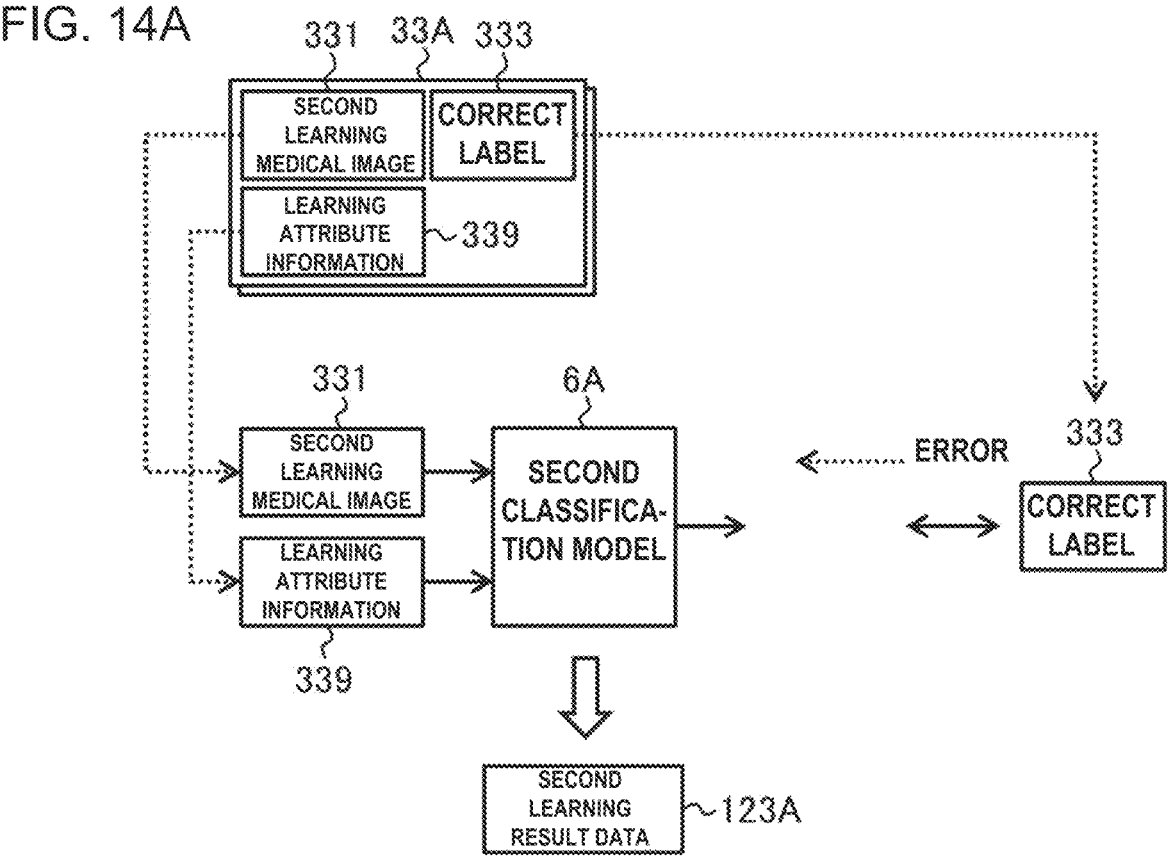
FIG. 14A schematically illustrates an example of a supervised learning process of a second classification model according to a modification.
Figure 14B:
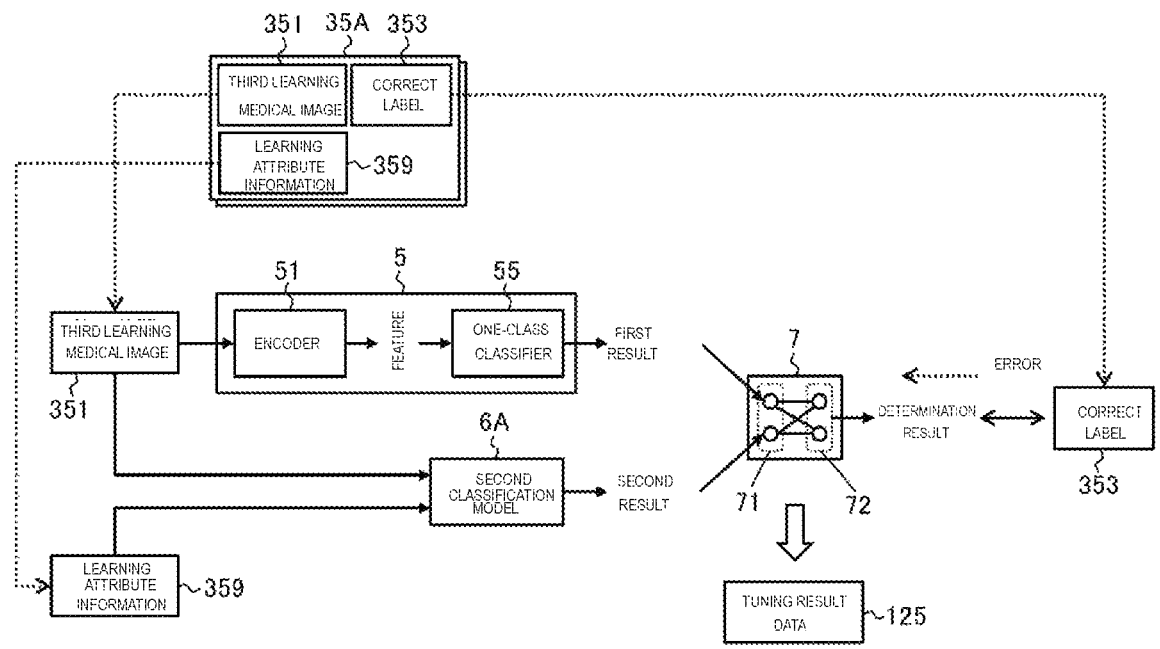
FIG. 14B schematically illustrates an example of a parameter tuning process according to the modification.
Figure 14C:
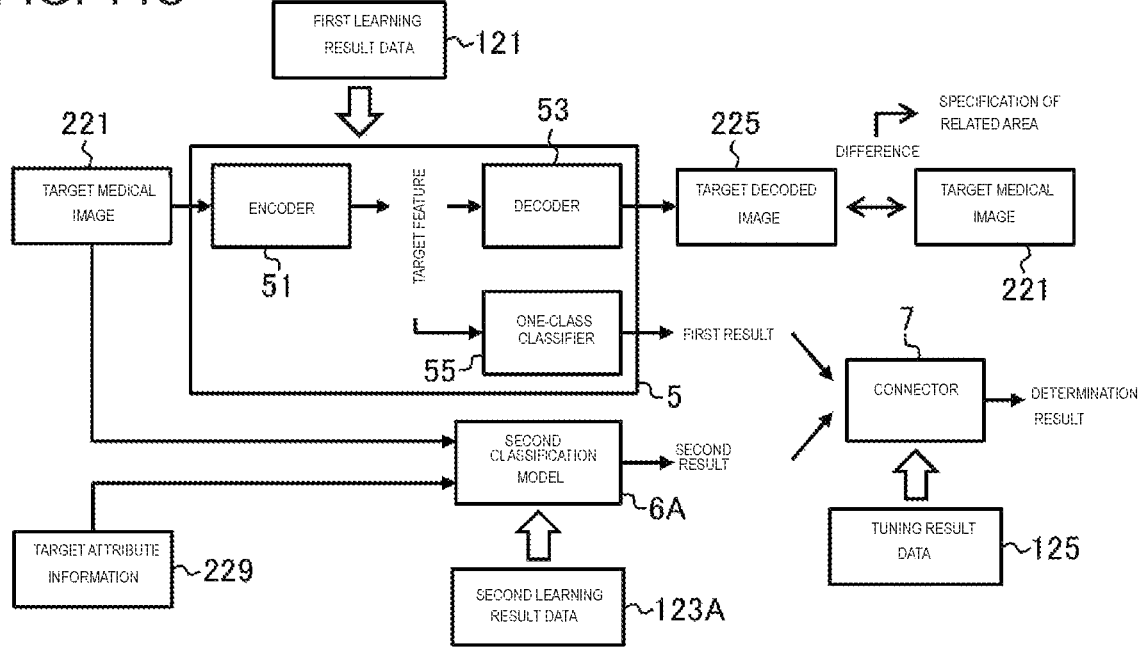
FIG. 14C schematically illustrates an example of a process of a diagnostic assistance apparatus according to the modification.

FIG. 14A schematically illustrates an example of a supervised learning process of the second classification model 6 configured to further accept an input of attribute information according to this modification. FIG. 14B schematically illustrates an example of a parameter tuning process of the connector 7 according to this modification. FIG. 14C schematically illustrates an example of a process of the diagnostic assistance apparatus 2 according to this modification.

As illustrated in FIG. 14A, when a second classification model 6A is configured to further accept an input of attribute information, learning data sets 33A each further includes learning attribute information 339 indicating attributes of a subject. The learning attribute information 339 is attribute information used as training data for supervised learning. Except for this point, each learning data set 33A may be configured in the same manner as the learning data set 33 described above. In step S121 described above, the control unit 11 acquires the plurality of learning data sets 33A, each being a combination of the second learning medical image 331, the correct label 333, and the learning attribute information 339.

Except for the configuration in which the second classification model 6A further accepts an input of attribute information, the second classification model 6A may be configured in the same manner as the second classification model 6. The configuration for accepting an input of attribute information may be determined as appropriate to the embodiment. For example, the second classification model 6A may be configured such that attribute information is inputted to the fully connected layer 63. As another example, the second classification model 6A may further include one or more layers arranged in parallel with the convolutional layer 61 and the pooling layers 62. In this case, the second classification model 6A may be configured such that attribute information is inputted to a layer on the side closest to input, and the output value of a layer on the side closest to output is inputted to the fully connected layer 63.

In step S122 described above, the second classification model 6A is trained by supervised learning additionally using the learning attribute information 339 such that the second classification model 6A evaluates the degree of normality of a body part captured in a fed medical image with reference to the fed attribute information. This means that the control unit 11 trains the second classification model 6A such that, with respect to each learning data set 33, in response to inputs of the second learning medical image 331 and the learning attribute information 339, when evaluating the degree of normality of a body part captured in the inputted second learning medical image 331, the evaluation result matches the correct label 333 corresponding to the second learning medical image 331. The training method may be the same as the embodiment. In step S123, the control unit 11 generates information about the trained second classification model 6A as second learning result data 123A. The second learning result data 123A may be the same as the second learning result data 123. Similarly to the embodiment, the generated second learning result data 123A may be provided for the diagnostic assistance apparatus 2 in a given method.

Additionally, similarly to the learning data sets 33A, tuning data sets 35A each further include learning attribute information 359 indicating attributes of a subject, as illustrated in FIG. 14B. The learning attribute information 359 is the same as the learning attribute information 339. Except for this point, each tuning data set 35A may be the same as the tuning data set 35. In step S131 described above, the control unit 11 acquires the plurality of tuning data sets 35A, each being a combination of the third learning medical image 351, the correct label 353, and the learning attribute information 359.

In step S132, similarly to the embodiment, the control unit 11 feeds the third learning medical image 351 of each tuning data set 35A to the trained first classification model 5 and performs the arithmetic operation of the trained first classification model 5. As a result, the control unit 11 acquires the first result of each third learning medical image 351 from the trained first classification model 5. The control unit 11 also feeds the third learning medical image 351 and the learning attribute information 359 of each tuning data set 35A to the trained second classification model 6A and performs the arithmetic operation of the trained second classification model 6A. As a result, the control unit 11 acquires the second result of each third learning medical image 351 from the trained second classification model 6A. The control unit 11 subsequently feeds the acquired first and second results to the connector 7 and performs the arithmetic operation of the connector 7. As a result, the control unit 11 acquires from the connector 7 a determination value or an output value indicating a determination result of each third learning medical image 351. In step S133, similarly to the embodiment, the control unit 11 tunes the parameters of the connector 7 to reduce errors between a determination result derived from a determination value or represented by an output value and a correct result indicated by the correct label 353, calculated on the respective tuning data sets 35A. As a result, the control unit 11 can tune the parameters of the connector 7 to optimize the accuracy of determination about the third learning medical images 351 of the tuning data sets 35A.

As illustrated in FIG. 14C, the diagnostic assistance apparatus 2 (the second model computation unit 213) according to this modification obtains the second learning result data 123A, thereby having the trained second classification model 6A. By the time when the operation in step S203 described above is performed, the control unit 21 operates as the data acquisition unit 211 and acquires target attribute information 229 indicating attributes of a target examinee. This means that in this modification the data acquisition unit 211 is configured to further acquire the target attribute information 229. The target attribute information 229 is attribute information used for the operation of diagnostic assistance. In step S203 described above, the control unit 21 further feeds the acquired target attribute information 229 to the trained second classification model 6A (specifically, input the target medical image 221 and the target attribute information 229 to the trained second classification model 6A) and performs an arithmetic operation of the trained second classification model 6A. By performing this arithmetic operation, the control unit 21 acquires an output value corresponding to the second result from the trained second classification model 6A. Except for these points, the diagnostic assistance apparatus 2 according to this modification performs the same process as the embodiment, so that the diagnostic assistance apparatus 2 according to this modification can determine whether a body part captured in the target medical image 221 is normal and output the determination result.

With this modification, the determination of whether a body part is normal can be made with additional reference to person's attributes. Thus, further improvement of the determination accuracy can be expected. The attributes relate to some kinds of person's characteristics such as age, sex, height, weight, waist circumference, and chest measurement. The attribute information (learning attribute information, target attribute information) may be acquired as appropriate; for example, the attribute information may be inputted by the operator with the input device. The first classification model 5 may also be configured to further accept an input of the attribute information. For example, the trained first classification model 5 may be generated for individual classes based on attributes indicated by the attribute information. In this case, the attribute classification may be carried out by, for example, designating each class by the operator or clustering.

4.3

In the embodiment, the operations in steps S205 to S208 may be omitted. When the trained decoder 53 is not used in the diagnostic assistance apparatus 2, information about the trained decoder 53 may be excluded from the first learning result data 121.

Furthermore, in the embodiment, the one-class classifier 55 may be excluded from the configuration of the first classification model 5. As described above, a portion with high probability of abnormality is not accurately reconstructed in the target decoded image 225, and thus, the portion is greatly different from a corresponding portion in the target medical image 221. For this reason, in the above case, the trained first classification model 5 may use a difference value between the target medical image 221 and the target decoded image 225 (for example, the sum of values of differences between corresponding picture elements) to evaluate the degree of normality of a body part of a target examinee.

In the embodiment, the first classification model 5 includes the encoder 51, the decoder 53, and the one-class classifier 55. The configuration of the first classification model 5 is, however, not limited to this example when the first classification model 5 can acquire by unsupervised learning a capability to evaluate the degree of normality of a body part captured in a medical image, and the configuration of the first classification model 5 may be determined as appropriate to the embodiment.

Figure 15:
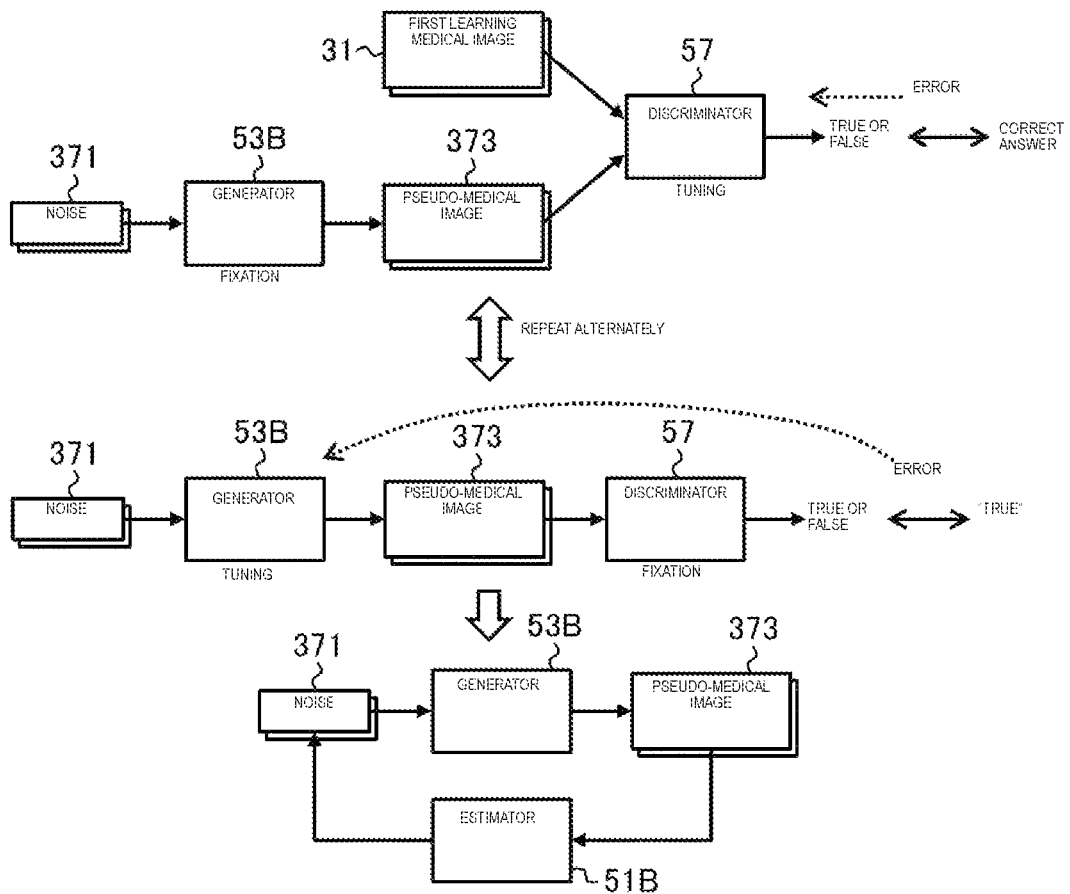
FIG. 15 schematically illustrates an example of an unsupervised learning process of a first classification model according to a modification.

FIG. 15 schematically illustrates an example of an unsupervised learning process of a first classification model according to this modification. The first classification model according to this modification includes an estimator 51B, a generator 53B, and a discriminator 57. The generator 53B is configured to accept an input of noises (latent variables) and output a pseudo-image generated based on the inputted noises. The discriminator 57 is configured to accept an input of an image and identify the origin of the input image, in other words, discriminate whether the input image is an image of learning data or a pseudo-image generated by the generator 53B. The estimator 51B is configured to accept an input of a medical image and estimate input values (noises) to be fed to the generator 53B so that the generator 53B can generate the input medical image; in other words, the estimator 51B is configured to estimate inputs (noises) in accordance with an output (a pseudo-image) of the generator 53B. The estimator 51B corresponds to the encoder 51, and the generator 53B corresponds to the decoder 53. The estimator 51B, the generator 53B, and the discriminator 57 each have a plurality of operational parameters. The generator 53B and the discriminator 57 may be implemented by neural networks, similarly to, for example, the encoder 51. The estimator 51B may be implemented by a neural network or a function expression such as regression model.

In this modification, unsupervised learning of the first classification model is adversarial learning of the generator 53B and the discriminator 57. Specifically, in step S112, the control unit 11 acquires a plurality of noises 371 from a predetermined probability distribution (for example, a Gaussian distribution). The control unit 11 inputs each acquired noise 371 to the generator 53B and performs an arithmetic operation of the generator 53B. As a result, the control unit 11 acquires a pseudo-medical image 373 generated based on the noise 371 from the generator 53B. The control unit 11 inputs each pseudo-medical image 373 to the discriminator 57 and performs an arithmetic operation of the discriminator 57, and as a result, the control unit 11 acquires an output value corresponding to the discrimination result of the pseudo-medical image 373 from the discriminator 57. In this case, the correct result is identifying the origin of the medical image as the generator 53B (corresponding to "false" in the drawing). The control unit 11 calculates an error between the output value acquired from the discriminator 57 and this correct result. In the same manner, the control unit 11 inputs each first learning medical image 31 to the discriminator 57 and performs an arithmetic operation of the discriminator 57, and as a result, the control unit 11 acquires an output value corresponding to the discrimination result of the first learning medical image 31 from the discriminator 57. In this case, the correct result is identifying the origin of the medical image as the first learning medical images 31 (corresponding to "true" in the drawing). The control unit 11 calculates an error between the output value acquired from the discriminator 57 and this correct result. While the operational parameters of the generator 53B are fixed, the control unit 11 tunes the operational parameters of the discriminator 57 by, for example, backpropagation to reduce the sum of errors calculated. As such, the control unit 11 trains the discriminator 57 to discriminate whether the generator 53B or the first learning medical images 31 is the origin of an input medical image (in other words, whether the input medical image is the pseudo-medical image 373 or the first learning medical image 31).

The control unit 11 also trains the generator 53B to generate the pseudo-medical image 373 in the manner in which the pseudo-medical image 373 degrades the discrimination performance of the discriminator 57. Specifically, the control unit 11 inputs each pseudo-medical image 373 to the discriminator 57 and performs an arithmetic operation of the discriminator 57, and as a result, the control unit 11 acquires an output value corresponding to the discrimination result of the pseudo-medical image 373 from the discriminator 57. In the case of training the generator 53B, the correct result is wrongly identifying the origin of the medical image as the first learning medical images 31 (corresponding to "true" in the drawing). The control unit 11 calculates an error between the output value acquired from the discriminator 57 and this correct result. While the operational parameters of the discriminator 57 are fixed, the control unit 11 tunes the operational parameters of the generator 53B by, for example, backpropagation to reduce the sum of errors calculated. In this manner, the control unit 11 can train the generator 53B to generate the pseudo-medical image 373 in the manner in which the pseudo-medical image 373 degrades the discrimination performance of the discriminator 57.

The control unit 11 alternately repeats the training of the discriminator 57 and the training of the generator 53B. How many times the trainings are repeated may be determined as appropriate to the embodiment. As such, the trained generator 53B and the trained discriminator 57 can be generated. The training of the discriminator 57 can impart to the discriminator 57 a capability to identify the origin of an input medical image, depending on the performance of the generator 53B. The training of the generator 53B can impart to the generator 53B a capability to generate the pseudo-medical image 373 that causes the discriminator 57 to misidentify the first learning medical image 31, depending on the discrimination performance of the discriminator 57. As a result, by alternately repeating the training of the discriminator 57 and the training of the generator 53B, the generator 53B can acquire a capability to generate the pseudo-medical image 373 similar to the first learning medical images 31 (in other words, capturing a normal body part), along with improvements of the discrimination performance of the discriminator 57.

Next, the control unit 11 generates the estimator 51B configured to estimate an input from an output of the trained generator 53B. The method for generating the estimator 51B may be selected as appropriate to the embodiment. For example, the control unit 11 acquires the plurality of noises 371 from the predetermined probability distribution. The control unit 11 generates the pseudo-medical image 373 from each noise 371 by using the trained generator 53B. As a result, the control unit 11 generates a plurality of data sets each being a combination of the noise 371 and the pseudo-medical image 373. The control unit 11 may derive as the estimator 51B a function expression for inversely calculating the noise 371 from the pseudo-medical image 373 by using a given method.

As another example, when the estimator 51B is implemented by a machine learning model such as a neural network, the control unit 11 may train the estimator 51B such that, with respect to each data set, when the estimator 51B acquires an estimation result in response to inputting the pseudo-medical image 373, the estimation result matches the corresponding noise 371. In this manner, it is possible to generate the trained estimator 51B capable of properly estimating an input from an output of the trained generator 53B.

As still another example, the control unit 11 may generate the trained estimator 51B with the use of at least one (hereinafter simply referred to as a "learning medical image") of the first learning medical image 31 and the second learning medical image 331. Specifically, the control unit 11 inputs a learning medical image to the estimator 51B and performs an arithmetic operation of the estimator 51B. By performing this arithmetic operation, the control unit 11 acquires from the estimator 51B an output value corresponding to the result of estimating a noise corresponding to the learning medical image. The control unit 11 subsequently inputs the noise estimated by the estimator 51B to the trained generator 53B and performs the arithmetic operation of the trained generator 53B. By performing this arithmetic operation, the control unit 11 acquires from the trained generator 53B a pseudo-medical image generated from the estimated noise. The control unit 11 then calculates errors (reconstruction errors) between the generated pseudo-medical image and the learning medical image. At this time, the control unit 11 may input the learning medical image to the trained discriminator 57 and perform the arithmetic operation of the trained discriminator 57; and the control unit 11 may further calculate an error of the discrimination result acquired from the trained discriminator 57. The control unit 11 tunes the operational parameters of the estimator 51B by, for example, backpropagation to decrease the sum of errors calculated. As a result, the control unit 11 trains the estimator 51B to minimize the difference between a learning medical image and a pseudo-medical image generated by the trained generator 53B from an estimation value estimated by the estimator 51B on the learning medical image and also minimize the error of the discrimination result acquired by the trained discriminator 57 on the learning medical image. As the result of this training process, it is possible to generate the trained estimator 51B capable of properly estimating an input from an output of the trained generator 53B.

In the manner described above, the trained first classification model can be generated. In this modification, the diagnostic assistance apparatus 2 uses the trained estimator 51B, the trained generator 53B, and the trained discriminator 57 to evaluate the degree of normality of a body part of a target examinee captured in the target medical image 221. Specifically, in step S202, the control unit 21 inputs the target medical image 221 to the trained estimator 51B and performs the arithmetic operation of the trained estimator 51B. By performing this arithmetic operation, the control unit 21 acquires from the trained estimator 51B the result of estimating a noise corresponding to the target medical image 221. The control unit 21 subsequently inputs the estimated noise to the trained generator 53B and performs the arithmetic operation of the trained generator 53B. By performing this arithmetic operation, the control unit 21 acquires from the trained generator 53B the result of generating a pseudo-medical image corresponding to the target medical image 221. The control unit 21 also inputs the target medical image 221 to the trained discriminator 57 and performs the arithmetic operation of the trained discriminator 57. By performing this arithmetic operation, the control unit 21 acquires a discrimination result on the target medical image 221.

Because unsupervised learning of the first classification model uses the first learning medical images 31 capturing normal body parts, the higher the possibility in which the body part of the target examinee captured in the target medical image 221 is normal is, the more similar to the target medical image 221 the pseudo-medical image generated by the trained generator 53B is; in other words, the smaller the difference value between the pseudo-medical image and the target medical image 221 is. Furthermore, the higher the possibility in which the body part of the target examinee captured in the target medical image 221 is normal is, the higher the possibility in which the trained discriminator 57 identifies the first learning medical image 31 as the origin of the target medical image 221 is. As a result, the control unit 21 can evaluate the degree of normality of the body part of the target examinee captured in the target medical image 221 in accordance with the difference value between the pseudo-medical image and the target medical image 221 and the output value (discrimination result) of the trained discriminator 57. With this modification, similarly to the embodiment, it is possible to provide the first classification model that can evaluate the degree of normality of a body part captured in a fed medical image by one-class classification.

It should be noted that this modification can perform the classification operation with the use of only either one of the two indicators described above. Thus, either one of the two indicators may be omitted. When the discrimination result by the trained discriminator 57 is omitted, the trained first classification model may be constituted by the trained estimator 51B and the generator 53B. This means that the discriminator 57 may be used only to train the generator 53B and may be excluded from the configuration of the first classification model. When the difference value between the pseudo-medical image and the target medical image 221 is omitted, the trained first classification model may be constituted by only the trained discriminator 57. This means that the trained discriminator 57 may be used as a one-class classifier.

4.4

In the embodiment, the connector 7 is implemented by a neural network. The configuration of the connector 7, however, is not necessarily limited to this example. The connector 7 may be implemented by, for example, a simple function expression including the first parameter and the second parameter. Connecting the weighted first result and the weighted second result may be simply summing or averaging the weighted first result and the weighted second result. In the embodiment, when tuning the first parameter and the second parameter, the control unit 11 may tune the thresholds as appropriate.

In the embodiment, the parameters of the connector 7 are tuned by machine learning. The method for tuning the parameters of the connector 7, however, is not necessarily limited to this example. For example, the first parameter and the second parameter may be optimized by a known optimization method such as differential evolution or Bayesian optimization. As another example, the model generation apparatus 1 may assign suitable candidate values to the first parameter and the second parameter and perform the determination operation on the third learning medical images 351. The model generation apparatus 1 may accordingly accept particular candidate values with the highest determination accuracy on the third learning medical images 351 as the parameters. In this case, the candidate values to be assigned may be predetermined. Alternatively, the candidate values to be assigned may be determined mechanically in, for example, a random manner. As another example, at least one of the first parameter, the second parameter, and the thresholds may be specified by inputs by the operator. The operator may be, for example, a medical doctor or user who operates the model generation apparatus 1 or the diagnostic assistance apparatus 2 directly or indirectly via a user terminal. The operator may tune the first parameter, the second parameter, and the thresholds as appropriate while checking the determination result of the third learning medical images 351. In the case of this example, the first parameter, the second parameter, and the thresholds can be easily tuned.

Further, in the embodiment, the diagnostic assistance apparatus 2 may tune the parameters of the connector 7. In this case, the third acquisition unit 114, the determination unit 115, and the tuning unit 116 may be excluded from the software configuration of the model generation apparatus 1. The software configuration of the diagnostic assistance apparatus 2 may further include the third acquisition unit 114 and the tuning unit 116. The first model computation unit 212, the second model computation unit 213, and the determination unit 214 may be configured to perform the same operations as the determination unit 115. As such, the diagnostic assistance apparatus 2 may be configured to perform the operations in steps S131 to S134.

Moreover, in the embodiment, the connector 7 may be excluded. In this case, the third acquisition unit 114, the determination unit 115, and the tuning unit 116 may be excluded from the software configuration of the model generation apparatus 1. Steps S131 to S134 may be excluded from the procedure of the model generation apparatus 1. In step S204, the control unit 21 may determine whether a body part of a target examinee is normal, as appropriate in accordance with the first and second results. For example, when at least one of the first result and the second result is evaluated as abnormal in view of avoiding unnoticed abnormalities, the control unit 21 may determine that the body part of the target examinee is non-normal. As another example, only when both the first result and the second result are evaluated as abnormal, the control unit 21 may determine that the body part of the target examinee is non-normal. As still another example, the control unit 21 may connect the first result and the second result without weighting and compare the acquired determination value to a threshold to determine whether the body part of the target examinee is normal.

4.5

In the embodiment, the first classification model 5 and the second classification model 6 are arranged in parallel. The configuration of the first classification model 5 and the second classification model 6, however, is not necessarily limited to this example. For example, the second classification model 6 may be configured to accept inputs of a medical image and a result of evaluating the medical image by the first classification model 5 and evaluate the degree of normality of a body part captured in the input medical image. In this case, in step S122 described above, the control unit 11 may perform supervised learning of the second classification model 6 by using the acquired learning data sets 33 and the trained first classification model 5. The supervised learning may include training the second classification model such that, with respect to each learning data set 33, in response to an input of the second learning medical image 331 and an input of the result of evaluating the second learning medical image 331 by the first classification model 5, when evaluating the degree of normality of a body part captured in the inputted second learning medical image 331, the evaluation result matches the correct label 333 corresponding to the second learning medical image 331. The connector 7 may be excluded. In this case, instead of steps S202 to S204, the control unit 21 of the diagnostic assistance apparatus 2 may operate as the determination unit 214 and determine whether a body part of a target examinee captured in the acquired target medical image 221 is normal, by using the trained first classification model 5 and the trained second classification model 6. The determination unit 214 may include the first model computation unit 212 and the second model computation unit 213. Specifically, the control unit 21 inputs the target medical image 221 to the trained first classification model 5 and performs the arithmetic operation of the trained first classification model 5. By performing this arithmetic operation, the control unit 21 acquires an evaluation result of the target medical image 221 by the trained first classification model 5. The control unit 21 inputs the target medical image 221 and the evaluation result by the first classification model 5 to the trained second classification model 6 and performs the arithmetic operation of the trained second classification model 6. By performing this arithmetic operation, the control unit 21 can acquire from the trained second classification model 6 a result of evaluating the degree of normality of a body part of a target examinee captured in the target medical image 221 (in this case, determining whether the body part is normal).

Figure 16A:
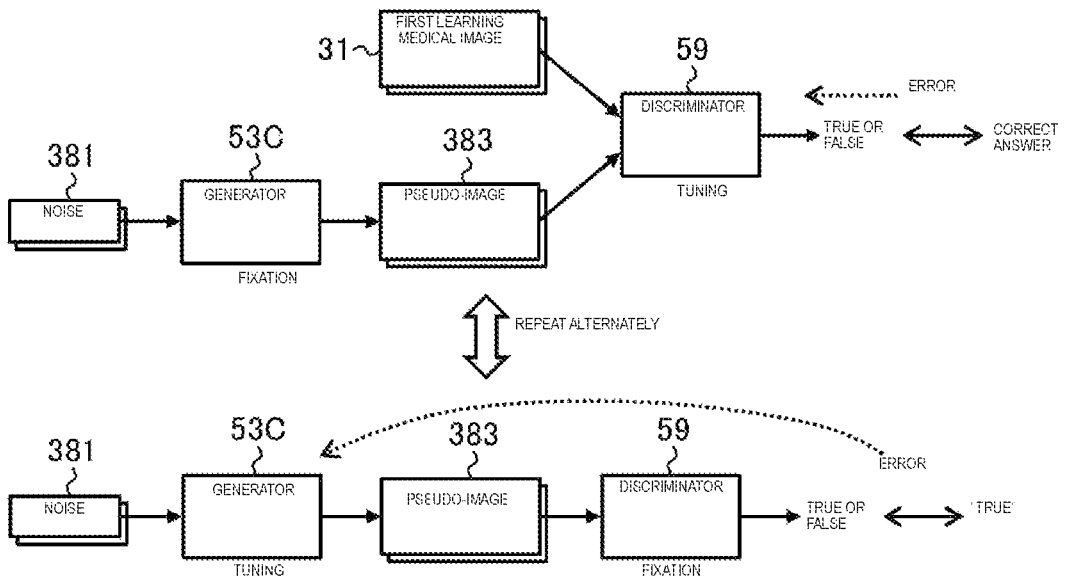
FIG. 16A schematically illustrates an example of an unsupervised learning process of a first classification model according to a modification.
Figure 16B:
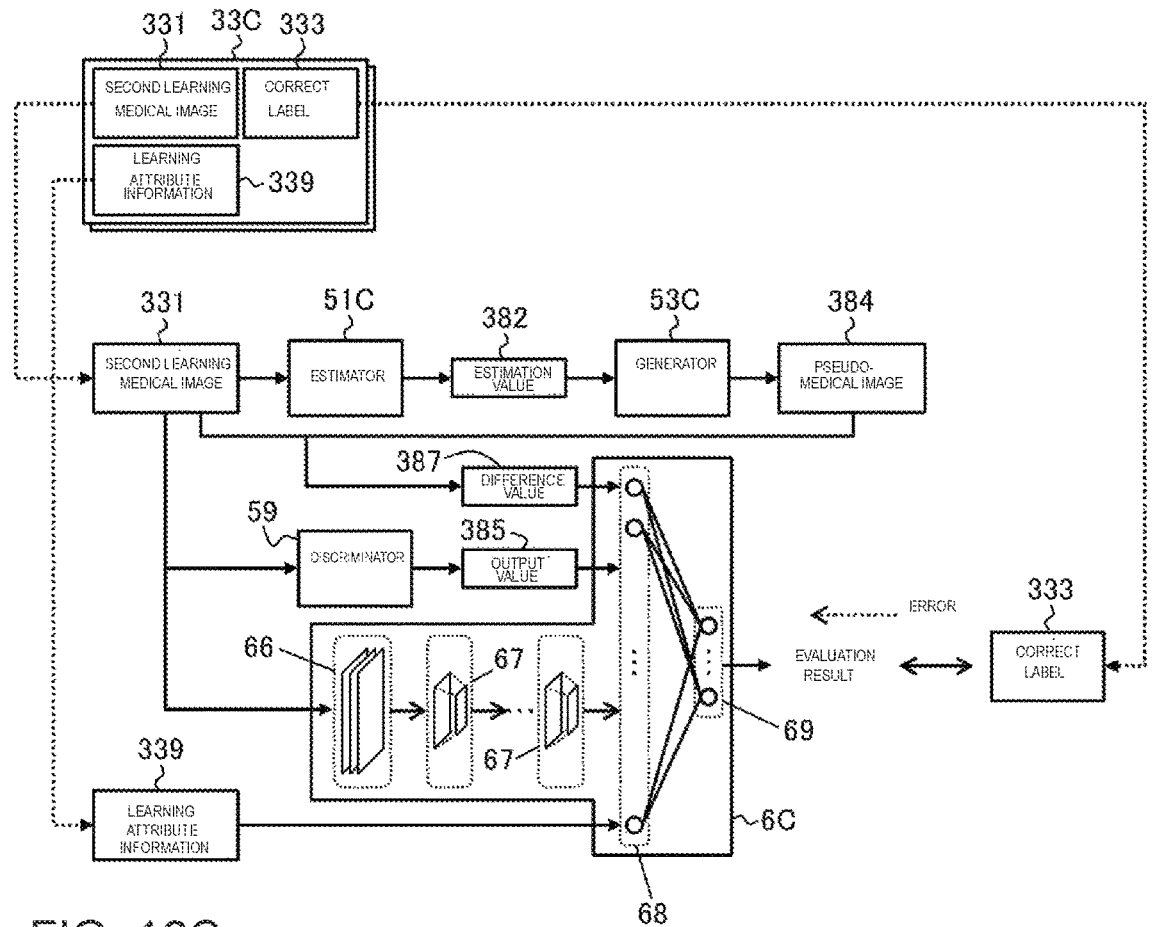
FIG. 16B schematically illustrates an example of a supervised learning process of a second classification model according to the modification.
Figure 16C:
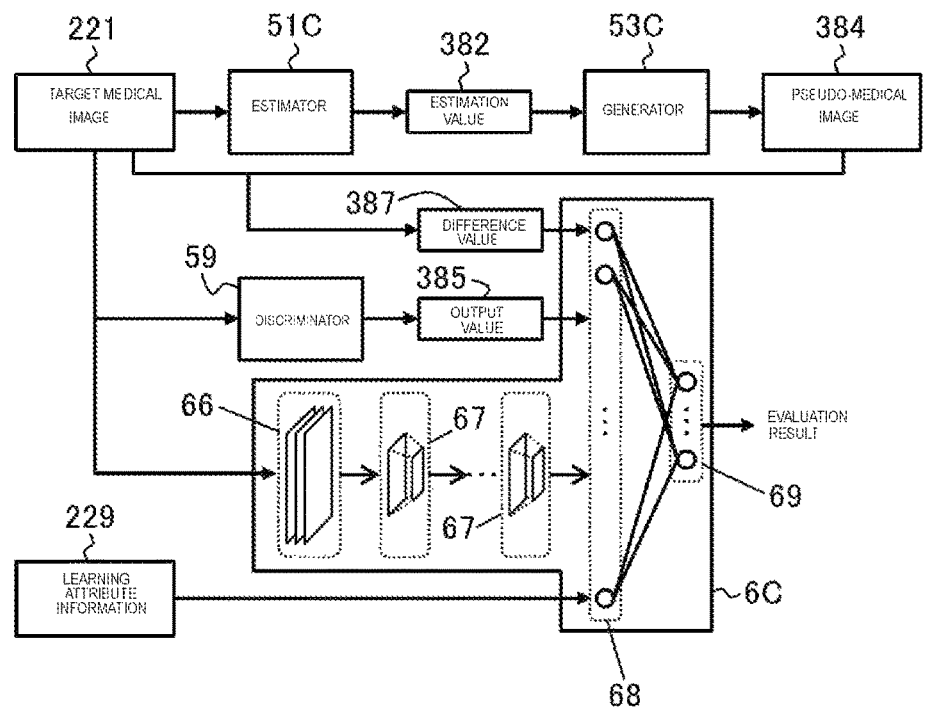
FIG. 16C schematically illustrates an example of a process of a diagnostic assistance apparatus according to the modification.

FIG. 16A schematically illustrates an example of an unsupervised learning process of a first classification model according to this modification. FIG. 16B schematically illustrates an example of an unsupervised learning process of a second classification model 6C according to this modification. FIG. 16C schematically illustrates an example of a process of the diagnostic assistance apparatus 2 according to this modification.

As illustrated in FIG. 16A, the first classification model according to this modification includes, similarly to the modification in FIG. 15 described above, a generator 53C and a discriminator 59. The generator 53C is configured to generate a pseudo-medical image 383 from a noise (latent variable) 381. The discriminator 59 is configured to accept an input of a medical image and identify the origin of the input medical image. The generator 53C may be configured in the same manner as the generator 53B, and the discriminator 59 may be configured in the same manner as the discriminator 57.

In step S112 described above, training the first classification model includes alternately repeating a first step of training the discriminator 59 to discriminate whether the generator 53C or the first learning medical images 31 is the origin of an input medical image and a second step of training the generator 53C to generate the pseudo-medical image 383 in the manner in which the pseudo-medical image 383 degrades the discrimination performance of the discriminator 59. The training steps may be the same as in the modification in FIG. 15 described above. In this modification, the classification result by the first classification model is made based on the difference (difference value) between an input medical image and a pseudo-medical image generated by the generator 53C, and the discrimination result of the input medical image by the discriminator 59.

As illustrated in FIG. 16B, the first classification model according to this modification further includes an estimator 51C configured to accept an input of a medical image and estimate an input value (noise) having been fed to the generator 53C to generate the input medical image by the generator 53C. The estimator 51C may be configured in the same manner as the estimator 51B. The estimator 51C may also be generated in the same manner as the estimator 51B. In this modification, the control unit 11 inputs the second learning medical image 331 of each learning data set 33C to the estimator 51C and performs an arithmetic operation of the estimator 51C. The learning data set 33C is the same as the learning data set 33A. By performing this arithmetic operation, the control unit 11 acquires from the estimator 51C an output value (an estimation value 382) corresponding to the result of estimating a noise corresponding to each second learning medical image 331. The control unit 11 subsequently inputs the estimation value 382 acquired by the estimator 51C to the trained generator 53C and performs an arithmetic operation of the trained generator 53C. By performing this arithmetic operation, the control unit 11 acquires from the trained generator 53c a pseudo-medical image 384 generated from the estimation value 382 of noise. The control unit 11 then calculates an error (a difference value 387) between the pseudo-medical image 384 generated and the corresponding second learning medical image 331. The control unit 11 also inputs the second learning medical image 331 of each learning data set 33C to the trained discriminator 59 and performs an arithmetic operation of the trained discriminator 59. By performing this arithmetic operation, the control unit 11 acquires from the trained discriminator 59 an output value 385 corresponding to a discrimination result of each second learning medical image. The control unit 11 tunes the operational parameters of the estimator 51C to decrease the sum of errors between the difference value 387 and the output value 385. As such, the control unit 11 trains the estimator 51C to, with respect to each learning data set 33C, minimize the difference between the second learning medical image 331 and the pseudo-medical image 384 and also minimize the error of the discrimination result on the second learning medical image 331 by the trained discriminator 59. As the result of this training process, it is possible to generate the trained estimator 51C capable of properly estimating an input from an output of the trained generator 53C.

A second classification model 6C according to this modification has a convolutional layer 66, pooling layers 67, and fully connected layers (68, 69). The convolutional layer 66, the pooling layers 67, and the fully connected layers (68, 69) may be configured in the same manner as the convolutional layer 61, the pooling layers 62, and the fully connected layers (63, 64) of the second classification model 6. In this modification, the difference value 387, the output value 385, and attribute information are inputted to the fully connected layer 68. This means that in this modification the fully connected layer 68 is an input layer for the difference value 387, the output value 385, and attribute information. The configuration of the second classification model 6C, however, is not necessarily limited to this example. Similarly to the above modification, the second classification model 6C may further include one or more layers arranged in parallel with the convolutional layer 66 and the pooling layers 67. In this case, at least any of the difference value 387, the output value 385, and attribute information may be inputted to a layer on the side closest to input.

In step S122, the control unit 11 calculates the difference value 387 and the output value 385 with respect to each learning data set 33C, similarly to the training process for the estimator 51C. The control unit 11 subsequently inputs the second learning medical image 331 of each learning data set 33C, the learning attribute information 339, the difference value 387, and the output value 385 to the corresponding input layers of the second classification model 6C and performs an arithmetic operation of the second classification model 6C. As a result, the control unit 11 acquires an output value corresponding to a classification result of each second learning medical image 331 by the second classification model 6C from the output layer. The control unit 11 then tunes the operational parameters of the second classification model 6C to decrease the sum of calculated errors. In this manner, the control unit 11 trains the second classification model 6C such that, with respect to each learning data set 33C, in response to inputs of the second learning medical image 331, the learning attribute information 339, the difference value 387, and the output value 385, when evaluating the degree of normality of a body part captured in the inputted second learning medical image 331, the evaluation result matches the correct label 333 corresponding to the second learning medical image 331. As a result, the trained second classification model 6C can be generated.

As illustrated in FIG. 16C, the control unit 21 of the diagnostic assistance apparatus 2 according to this modification, instead of steps S202 to S204, determines whether a body part of a target examinee captured in the acquired target medical image 221 is normal, by using the trained first classification model and the trained second classification model 6C. Specifically, the control unit 21 inputs the acquired target medical image 221 to the trained estimator 51C and performs the arithmetic operation of the trained estimator 51C. By performing this arithmetic operation, the control unit 21 acquires the estimation value 382 of noise from the trained estimator 51C. The control unit 21 inputs the estimation value 382 of noise to the trained generator 53C and performs the arithmetic operation of the trained generator 53C. By performing this arithmetic operation, the control unit 21 acquires from the trained generator 53c the pseudo-medical image 384 generated from the estimation value 382. The control unit 21 calculates the difference (the difference value 387) between the target medical image 221 and the pseudo-medical image 384. The control unit 21 also inputs the target medical image 221 to the trained discriminator 59 and performs the arithmetic operation of the trained discriminator 59. By performing this arithmetic operation, the control unit 21 acquires from the trained discriminator 59 an output value 385 corresponding to a discrimination result of the target medical image 221. Similarly to the above modification, the control unit 21 acquires the target attribute information 229 indicating attributes of the target examinee as appropriate. The control unit 21 inputs the target medical image 221, the target attribute information 229, the difference value 387, and the output value 385 to the corresponding input layers of the trained second classification model 6C and performs the arithmetic operation of the trained second classification model 6C. By performing this arithmetic operation, the control unit 21 can acquire an output value corresponding to a result of determining whether the body part of the target examinee captured in the target medical image 221 is normal, from the output layer (the fully connected layer 69) of the trained second classification model 6C.

Similarly to the embodiment, this modification can provide the first classification model trained by unsupervised learning and the second classification model trained by supervised learning. This can improve accuracy of classifying medical images with relatively low costs. Furthermore, in this modification, the operations to calculating the difference value 387 and the output value 385 can be performed in a common manner between the training process for the estimator 51C and the training process for the second classification model 6C. Hence, the training process for the estimator 51C and the training process for the second classification model 6C can be performed simultaneously. This can improve efficiency of machine learning processing.

In this modification, the discrimination result of the input medical image by the discriminator 59 may be omitted from the evaluation result by the first classification model. In this case, the discriminator 59 may be used only to train the generator 53B and may be excluded from the configuration of the first classification model. Further, attribute information may be omitted from the inputs to the second classification model 6C. In this case, the learning attribute information 339 may be excluded from each learning data set 33C. The operations relating to the target attribute information 229 may be excluded from the procedure of the diagnostic assistance apparatus 2. Moreover, the difference value 387 and the output value 385 may be inputted to the second classification model 6C after summation.

4.6

In the embodiment, the diagnostic assistance system 100 is formed by the model generation apparatus 1 and the diagnostic assistance apparatus 2 that are connected through a network. The configuration of the diagnostic assistance system 100, however, is not necessarily limited to this example, and the configuration can be changed as appropriate to the embodiment.

Figure 17:
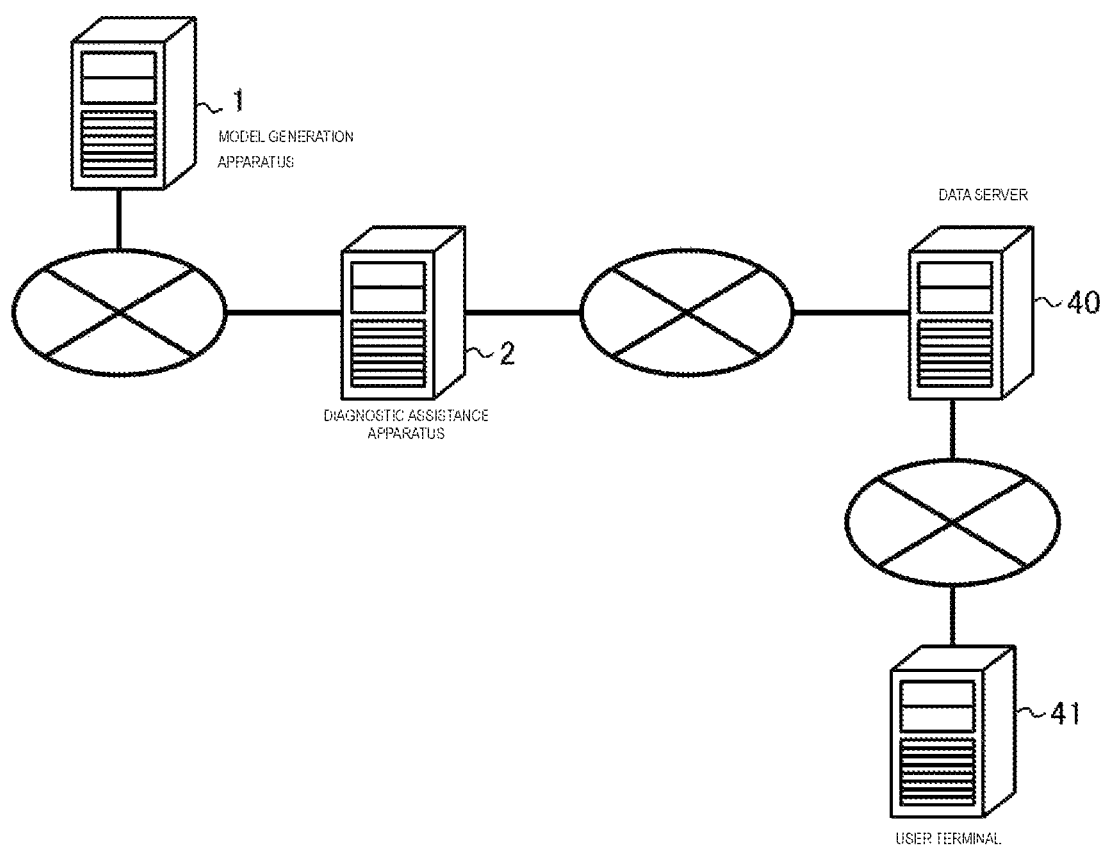
FIG. 17 schematically illustrates a configuration of a diagnostic system according to a modification.

FIG. 17 schematically illustrates an example of a system configuration according to this modification. A system according to this modification includes, as well as the diagnostic assistance system 100 according to the embodiment, a data server 40 and a user terminal 41. The data server 40 and the user terminal 41 may be configured to have processor and memory resources as appropriate, similarly to, for example, the model generation apparatus 1. The data server 40 may be implemented by, for example, a general-purpose server or NAS. The user terminal 41 may be implemented by, for example, a general-purpose PC, a tablet terminal, or a mobile phone such as a smartphone.

In this modification, the target medical image 221 and the result information indicating a determination result of the target medical image 221 by the diagnostic assistance apparatus 2 are provided for the data server 40 in a given method. The data server 40 collects the target medical image 221 and the result information. Similarly to the embodiment, the result information may be associated or combined with the target medical image 221. In this modification, the user such as a medical doctor can access the data server 40 by using the user terminal 41 and view the target medical image 221 and the result information. As in this modification, individual computers may be prepared for these purposes; one computer is used to collect the target medical image 221 and the result information, and the other to view the target medical image 221 and the result information. In this modification, the user may directly access the diagnostic assistance apparatus 2 by using the user terminal 41 to view the target medical image 221 and the result information.

1 model generation apparatus, 11 control unit, 12 storage unit, 13 communication interface, 14 input device, output device, 16 drive, 91 storage medium, 81 model generation program, 110 first acquisition unit, 111 first learning unit, 112 second acquisition unit, 113 second learning unit, 114 third acquisition unit, 115 determination unit, 116 tuning unit, 117 storage processing unit, 118 primary data acquisition unit, 119 enlargement processing unit, 121 first learning result data, 123 second learning result data, 125 tuning result data, 2 diagnostic assistance apparatus, 21 control unit, storage unit, 23 communication interface, 24 input device, 25 output device, 26 drive, 92 storage medium, 82 diagnostic assistance program, 211 data acquisition unit, 212 first model computation unit, 213 second model computation unit, 214 determination unit, 215 output unit, 221 target medical image, 225 target decoded image, 251 text indication, 252 outer frame, 255 box, 256 emphasized area, 257 heat map, 31 first learning medical image, 33 learning data set, 331 second learning medical image, 333 correct label, 35 tuning data set, 351 third learning medical image, 353 correct label, 390 primary medical image, 395 new medical image, 5 first classification model, 51 encoder, 511 input layer, 512 intermediate (hidden) layer, 513 output layer, 53 decoder, 531 input layer, 532 intermediate (hidden) layer, 533 output layer, one-class classifier, 551 input layer, 552 intermediate (hidden) layer, 553 output layer, 6 second classification model, 61 convolutional layer, 62 pooling layer, 63, 64 fully connected layer, 7 connector, 71 input layer, 72 output layer

The invention claimed is:
1. A diagnostic assistance apparatus comprising:
a data acquisition unit configured to acquire a target medical image of a body part of a target examinee;
at least one processor comprising:
a first classification model trained, by unsupervised learning using a plurality of first learning medical images of normal body parts, to provide an evaluation of a degree of normality of the body part in the acquired target medical image by one-class classification; and
a second classification model trained, by supervised learning using a plurality of learning data sets, each learning data set comprising a combination of a second learning medical image and a correct label indicating whether the body part captured in the second learning medical image is normal, to provide the evaluation of the degree of normality of the body part captured in the acquired target medical image, the second learning medical images of the plurality of learning data sets comprising a normal medical image capturing a normal body part and an abnormal medical image capturing an abnormal body part,
the at least one processor being configured to:
by feeding the acquired target medical image to the trained first classification model and performing a first operation of the trained first classification model, acquire as a first result the degree of normality evaluated by the one-class classification on the body part of the target examinee captured in the target medical image;
by feeding the acquired target medical image to the trained second classification model and performing a second operation of the trained second classification model, acquire as a second result the degree of normality evaluated on the body part of the target examinee captured in the target medical image; and in accordance with the first result and the second result, provide a determination of whether the body part of the target examinee captured in the target medical image is normal; and an output device configured to output the determination.

2. The diagnostic assistance apparatus according to claim 1, wherein:

the first result and the second result indicate the degree of normality of the body part by a numerical value, the at least one processor comprises a connector including a first parameter that determines a first priority level of the first result and a second parameter that determines a second priority level of the second result, the at least one processor is configured to provide the determination by:

feeding the acquired first result and the acquired second result to the connector, weighting the first result and the second result by using the first parameter and the second parameter, providing a connection between the weighted first result and the weighted second result, comparing the numerical value acquired by the connection to a threshold, and determining whether the body part of the target examinee is normal.

3. The diagnostic assistance apparatus according to claim 2, wherein the first parameter and the second parameter are tuned to optimize accuracy of the determination on a plurality of third learning medical images, wherein body parts captured in the plurality of third learning medical images have been determined to be normal or non-normal.

4. The diagnostic assistance apparatus according to claim 2, wherein the first parameter, the second parameter, and/or the threshold is specified by an input by an operator.

5. The diagnostic assistance apparatus according to claim 1, wherein:

the first classification model includes an encoder that is configured to provide a conversion of the acquired target medical image into a target feature, and a decoder that is configured to decode the acquired target medical image from the target feature, and the unsupervised learning includes training the encoder and the decoder such that, when each first learning medical image is fed to the encoder, a decoded image responsively generated by the decoder matches the first learning medical image.

6. The diagnostic assistance apparatus according to claim 5, wherein:

the first classification model comprises a one-class classifier that is trained by the unsupervised learning to provide the evaluation by the one-class classification in accordance with the target feature acquired by the encoder, and the first operation comprises, by feeding the target feature acquired by the conversion to the trained one-class classifier, acquiring the first result from the trained one-class classifier.

7. The diagnostic assistance apparatus according to claim 6, wherein the one-class classifier is implemented by a neural network.

8. The diagnostic assistance apparatus according to claim 5, wherein:

the first operation comprises, when the body part of the target examinee is determined to be non-normal:

providing, by feeding the acquired target medical image to the trained encoder, the conversion of the target medical image into the target feature, generating, by feeding the target feature acquired by the conversion to the trained decoder, a target decoded image from the target feature, determining a difference between the target medical image and the generated target decoded image, and specifying, in the target medical image, a related area by which the body part of the target examinee is determined to be non-normal, in accordance with the difference, and the output of a result of the determination includes an output of information indicating the related area specified.

9. The diagnostic assistance apparatus according to claim 1, wherein:

the plurality of learning data sets each further comprise learning attribute information, the second classification model is trained, by the supervised learning additionally using the learning attribute information, to provide the evaluation of the degree of normality of the body part captured in the acquired target medical image with reference to fed attribute information, the data acquisition unit is further configured to additionally acquire target attribute information indicating an attribute of the target examinee, and the at least one processor is further configured to acquire the second result by additionally feeding the acquired target attribute information to the trained second classification model, and performing the second arithmetic operation of the trained second classification model.

10. The diagnostic assistance apparatus according to claim 1, wherein the second classification model is implemented by a convolutional neural network.

11. The diagnostic assistance apparatus according to claim 1, wherein the output comprises associating result information indicating a result of the determination with the target medical image.

12. The diagnostic assistance apparatus according to claim 11, wherein the result information is implemented by a Digital Imaging and Communications in Medicine (DICOM) tag.

13. The diagnostic assistance apparatus according to claim 1, wherein the output comprises combining information indicating a result of the determination with the target medical image.

14. A model generation apparatus comprising:

a first acquisition unit configured to acquire a plurality of first learning medical images of normal body parts;

a second acquisition unit configured to acquire a plurality of learning data sets, each learning data set comprising a combination of second learning medical images and a correct label indicating whether the body part captured in the second learning medical image is normal, the second learning medical images of the plurality of learning data sets comprising a normal medical image of a normal body part and an abnormal medical image of an abnormal body part;

a third acquisition unit configured to acquire a plurality of third learning medical images, wherein body parts captured in the plurality of third learning medical images have been determined to be normal or non-normal; and at least one processor configured to:
perform unsupervised learning of a first classification model by using the plurality of first learning medical images acquired, the first classification model being configured to accept an input medical image and provide an evaluation of a degree of normality of a body part captured in the input medical image by one-class classification, the unsupervised learning comprising training the first classification model such that: when the input medical image belongs to a class of the plurality of first learning medical images, the body part captured in the input medical image is evaluated as normal; and when the input medical image does not belong to the class of the plurality of first learning medical images, the body part captured in the input medical image is evaluated as non-normal;
perform supervised learning of a second classification model by using the plurality of learning data sets acquired, the second classification model being configured to accept the input medical image and provide the evaluation of a degree of normality of the body part captured in the input medical image, the supervised learning including training the second classification model such that, with respect to each learning data set, in response to an input of one of the second learning medical images, when providing the evaluation of the degree of normality on the body part captured in the input second learning medical image, a result of the evaluation matches the correct label corresponding to the input second learning medical image;
by using the trained first classification model and the trained second classification model, provide a determination of whether the body part captured in each third learning medical image acquired is normal;
by feeding each third learning medical image to the trained first classification model, acquire as a first result the degree of normality evaluated on the body part captured in the third learning medical image by one-class classification;
by feeding each third learning medical image to the trained second classification model, acquire as a second result the degree of normality evaluated on the body part captured in the third learning medical image, the first result and the second result being configured to indicate the degree of normality of the body part by a numerical value,
the at least one processor comprising a connector including a first parameter that determines a first priority level of the first result and a second parameter that determines a second priority level of the second result, and being further configured to:
by feeding the acquired first result and the acquired second result to the connector, weight the first result and the second result by using the first parameter and the second parameter;
provide a connection between the weighted first result and the weighted second result;
compare the numerical value acquired by the connection to a threshold,
provide the determination of whether the body part captured in each third learning medical image is normal; and
optimize accuracy of the determination on each third learning medical image by tuning the first parameter and the second parameter.

15. The model generation apparatus according to claim 14, wherein
the plurality of third learning medical images comprises one or more limit samples, and
the at least one processor is further configured to tune the first parameter and the second parameter to avoid making the determination incorrect on the one or more limit samples.

16. The model generation apparatus according to claim 14, the at least one processor being further configured to:
by subjecting a primary medical image capturing the body part to enlargement processing, generate at least a portion of a collection of the plurality of first learning medical images and the second learning medical images of the plurality of learning data sets.

17. The model generation apparatus according to claim 16, wherein the enlargement processing is constituted by parallel translation, rotation, swiveling, flipping or flopping, cropping, contrast change, enlargement, reduction, or any combination thereof, performed on the primary medical image.

18. A model generation apparatus comprising:
a first acquisition unit configured to acquire a plurality of first learning medical images capturing normal body parts;
a second acquisition unit configured to acquire a plurality of learning data sets, each learning data set comprising a combination of second learning medical images and a correct label indicating whether the body part captured in the second learning medical image is normal, the second learning medical image of the plurality of learning data sets comprising a normal medical image of a normal body part and an abnormal medical image of an abnormal body part; and
at least one processor configured to:
perform unsupervised learning of a first classification model by using the plurality of first learning medical images acquired, the first classification model being configured to accept an input medical image and provide an evaluation of a degree of normality of a body part captured in the input medical image by one-class classification, the unsupervised learning including training the first classification model such that: when the input medical image belongs to a class of the plurality of first learning medical images, the body part captured in the input medical image is evaluated as normal; and when the input medical image does not belong to the class of the plurality of first learning medical images, the body part captured in the input medical image is evaluated as non-normal; and
perform supervised learning of a second classification model by using the plurality of learning data sets acquired and the trained first classification model, the second classification model being configured to accept the input medical image and an input of a result of the evaluation on the medical image by the first classification model and provide the evaluation of the degree of normality of the body part captured in the input medical image, the supervised learning including training the second classification model such that, with respect to each learning data set, in response to an input of the second learning medical image and an input of a result of the evaluation on the second learning medical image by the first classification model, when providing the evaluation of the degree of normality on the body part captured in the input second learning medical image, the result of the evaluation matches the correct label corresponding to the second learning medical image.

19. The model generation apparatus according to claim 18, wherein:
the first classification model comprises:
a generator configured to generate a pseudo-medical image, and
a discriminator configured to accept the input medical image and identify an origin of the input medical image,
the training of the first classification model includes alternately repeating:
a first step of training the discriminator to identify whether the generator or the plurality of first learning medical images is the origin of the input medical image, and
a second step of training the generator to generate the pseudo-medical image that degrades discrimination performance of the discriminator, and the result of the evaluation by the first classification model is made based on a difference between the input medical image and the pseudo-medical image generated by the generator.

20. The model generation apparatus according to claim 19, wherein
the first classification model further comprises an estimator configured to accept the input medical image and estimate an input value fed to the generator to generate the input medical image by the generator, and
the at least one processor is further configured to further train the estimator to, with respect to each learning data set, minimize a difference between the second learning medical image and the pseudo-medical image generated by the trained generator from an estimation value estimated by the estimator from the second learning medical image.

* * * * *

UNITED STATES PATENT AND TRADEMARK OFFICE
CERTIFICATE OF CORRECTION

| | | |
|---|---|---|
| PATENT NO. | : 12,333,790 B2 | Page 1 of 1 |
| APPLICATION NO. | : 17/821850 | |
| DATED | : June 17, 2025 | |
| INVENTOR(S) | : Kouji Take et al. | |

It is certified that error appears in the above-identified patent and that said Letters Patent is hereby corrected as shown below:

In the Specification

Column 25, Line 5, "control unit (CPU)" should be --control unit 21 (CPU)--

Column 56, Line 3, "output device," should be --15 output device,--

Column 56, Line 11, "storage unit," should be --22 storage unit,--

Column 56, Line 27, "one-class classifier," should be --55 one-class classifier,--

Signed and Sealed this
Nineteenth Day of August, 2025

Coke Morgan Stewart
*Acting Director of the United States Patent and Trademark Office*